(12) United States Patent
Leahy et al.

(10) Patent No.: US 7,973,061 B2
(45) Date of Patent: Jul. 5, 2011

(54) ANAPLASTIC LYMPHOMA KINASE MODULATORS AND METHODS OF USE

(75) Inventors: James William Leahy, San Leandro, CA (US); Gary Lee Lewis, San Francisco, CA (US); John M. Nuss, Danville, CA (US); Brain Hugh Ridgway, Belmont, CA (US); Joan C. Sangalang, Mountain View, CA (US)

(73) Assignee: Exelixis, Inc., South San Francisco, CA (US)

( * ) Notice: Subject to any disclaimer, the term of this patent is extended or adjusted under 35 U.S.C. 154(b) by 504 days.

(21) Appl. No.: 10/598,911

(22) PCT Filed: Mar. 31, 2005

(86) PCT No.: PCT/US2005/010969
§ 371 (c)(1),
(2), (4) Date: Jun. 7, 2007

(87) PCT Pub. No.: WO2005/097765
PCT Pub. Date: Oct. 20, 2005

(65) Prior Publication Data
US 2009/0186905 A1    Jul. 23, 2009

Related U.S. Application Data

(60) Provisional application No. 60/558,800, filed on Mar. 31, 2004.

(51) Int. Cl.
A61K 31/41 (2006.01)
A61K 31/415 (2006.01)
C07D 249/00 (2006.01)
C07D 257/04 (2006.01)

(52) U.S. Cl. ........ 514/359; 514/383; 514/403; 548/190; 548/195; 548/255; 548/262.2; 548/300.1; 549/79

(58) Field of Classification Search .................. 548/190, 548/195
See application file for complete search history.

(56) References Cited

U.S. PATENT DOCUMENTS 5,229,386 A * 7/1993 Takasugi et al. ........... 514/236.8
6,673,927 B2   1/2004 Gordon et al.

FOREIGN PATENT DOCUMENTS

JP    2001-163802 A   6/2001

OTHER PUBLICATIONS

Patani, et al., Chem. Rev., 1996, 96, pp. 3147-3176.*
Debono et al., J.O.C., 1992, 57, pp. 5200-5208.*
Hoekstra et al., Bio. Med. Chem. Lett., 1998, 8, pp. 1649-1654.*
Debono/Hoekstra et al., JOC, 1992, 57(19), 5200-5208.*
Debono, M., "The Structures of A10255B, -G, and -J: New Thiopeptide Antibodies Produced by Streptomyces Gardneri," J. Org. Chem. Jun. 1992, vol. 57, pp. 5200-5208.
Zhou, H., "Chemical and Enzymatic Synthesis of Fluorinated-Dehydroalanine-Containing Peptides", May 2003, vol. 4, pp. 1206-1215.
International Search Report for PCT/US05/10969, Dated Aug. 19, 2005.

* cited by examiner

*Primary Examiner* — Susannah Chung
(74) *Attorney, Agent, or Firm* — McDonnell Boehnen Hulbert & Berghoff LLP

(57) ABSTRACT

The present invention relates to compounds of the Formula I, wherein L, X, Y, Z, $R^1$, $R^2$, $R^3$ and $R^4$ are defined herein. The invention also provides methods of using the compounds for inhibition of kinases, more specifically ALK kinases. The invention provides compounds for modulating protein kinase enzymatic activity for modulating cellular activities such as proliferation, differentiation, programmed cell death, migration and chemoinvasion. Compounds of the invention inhibit, regulate and/or modulate kinase receptor signal transduction pathways related to the changes in cellular activities as mentioned above, and the invention includes compositions which contain these compounds, and methods of using them to treat kinase-dependent diseases and conditions; (Formula I).

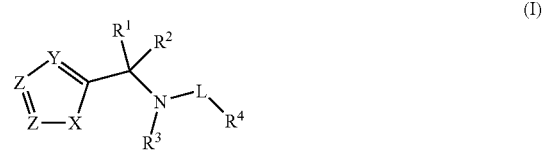

(I)

31 Claims, No Drawings

ANAPLASTIC LYMPHOMA KINASE MODULATORS AND METHODS OF USE

REFERENCE TO RELATED APPLICATIONS

This application claims priority to U.S. provisional patent application 60/558,800 filed Mar. 31, 2004. The contents of the prior application are hereby incorporated in their entirety.

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to thiazole compounds which inhibit, regulate and/or modulate Anaplastic Lymphoma Kinase (ALK) signal transduction pathways related to the changes in cellular activities as mentioned above, compositions which contain these compounds, and methods of using them to treat kinase, and more specifically, ALK-dependent diseases and conditions.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity on cell differentiation and proliferation are staggering; i.e., virtually all aspects of cell life in one way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6):334-339, 1994, which is hereby incorporated by reference.

The non-receptor type of tyrosine kinases is also comprised of numerous families, including Src, Frk, Btk, Csk, Abl, Zap70, Fes/Fps, Fak, Jak, Ack, and LIMK. Each of these families is then further sub-divided into varying subfamilies. For example, the Src family is one of the largest and includes Src, Yes, Fyn, Lyn, Lck, Blk, Hck, Fgr, and Yrk. The Src subfamily of kinases has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth, associated with cancer. In addition to cancer, altered kinase signaling is implicated in numerous other pathological diseases. These include, but are not limited to: immunological disorders such as rheumatoid arthritis, graft-host diseases, multiple sclerosis, psoriasis; cardiovascular diseases such as atherosclerosis, myocardio-infarction, ischemia, stroke and restenosis; other inflammatory and degenerative diseases such as interbowel diseases, osteoarthritis, macular degeneration, diabetic retinopathy. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stromal cancers (GIST). Gleevec is a c-Kit and Abl kinase inhibitor.

Modulation (particularly inhibition) of cell proliferation and apoptosis, two key cellular processes needed for tumor grown and survival (Matter, A., Drug Disc. Technol. 2001 6, 1005-1024), is an attractive goal for development of small-molecule drugs. Anti-proliferative and pro-apoptotic therapy represents a potentially important approach for the treatment of solid tumors and other disease associated with dysregulated cell growth, including ischemic coronary artery disease, diabetic retinopathy, psoriasis and rheumatoid arthritis.

One particularly attractive target for small-molecule modulation, with respect to antiproliferative and proapoptotic activity is Anaplastic Lymphoma Kinase (ALK). ALK is a novel receptor tyrosine kinase (RTK) belonging to the insulin receptor subfamily. ALK is present in tumors as a result of a (2:5)(p23'q35) chromosomal translocation, which produces fusion proteins between ALK and other proteins such as nucleophosmin (NPM). The immunocytochemical detection of the NPM-ALK fusion protein (and proteins encoded by other ALK fusion genes) has allowed the definition of a tumor classification as "ALK-positive lymphoma." Eight variant ALK fusion proteins have been detected to date and all contain ALK kinase activity.

Activation of ALK occurs either by binding of the endogenous ALK mitogenic ligand, pleiotrophin, or by self-aggregation of the ALK fusion proteins, which causes autophosphorylation resulting in an increase of receptor dependent signaling. ALK activation causes increased cell proliferation and apoptosis via activation of the PKC, MAPK and PIP3K pathways.

ALK fusion proteins or full length ALK proteins have been detected not only in ALK-positive lymphomas but also in B-cell lymphoma, neuroblastoma and inflammatory myofibroblastic tumors. Recent analysis shows that ALK expression is a marker for a lymphoma subtype with a good prognosis and there are reports of a five-year survival of approximately 80% for ALK-positive lymphomas, compared to 15-45% for ALK-negative lymphomas of anaplastic large cell morphology. (See Morris, et al., Brit. J. Hematol. (2001) 113, 275-295; Stein, et al., Blood (2000) 96, 3681-3695; Drexler, et al. Leukemia (2000) 14, 1533-1559). Thus modulation of ALK is desirable as a means to treat certain cancers and cancer-related disease.

Accordingly, the identification of small-molecule compounds that specifically inhibit, regulate and/or modulate the signal transduction of kinases, particularly ALK, is desirable as a means to treat or prevent disease states associated with abnormal cell proliferation and apoptosis, and is an object of this invention.

SUMMARY OF THE INVENTION

In one aspect, the present invention provides compounds for modulating the activity of ALK kinases and methods of treating diseases mediated by the activity of ALK utilizing the compounds and pharmaceutical compositions thereof. Diseases mediated by ALK activity include, but are not limited to, diseases characterized in part by migration, invasion, proliferation and other biological activities associated with invasive cell growth.

In another aspect, the invention provides methods of screening for modulators of ALK activity. The methods comprise combining a composition of the invention, typically ALK, and at least one candidate agent and determining the effect of the candidate agent on the ALK activity.

In yet another aspect, the invention also provides pharmaceutical kits comprising one or more containers filled with one or more of the ingredients of pharmaceutical compounds and/or compositions of the present invention, including, ALK enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable carriers and excipients.

In yet another aspect, the invention also provides methods of making a compound of the invention and, optionally, pharmaceutically acceptable carriers and excipients.

These and other features and advantages of the present invention will be described in more detail below with reference to the associated drawings.

DETAILED DESCRIPTION OF THE INVENTION

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as artheroscrosis, myocardioinfarction, ischemia, stroke and restenosis; other inflammatory and degenerative diseases such as interbowel diseases, osteoarthritus, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally", but proliferation and migration enhancement may be desired. Alternatively, reduction in "normal" cell proliferation and/or migration rate may be desired.

The present invention comprises a compound for modulating ALK activity according to Formula I,

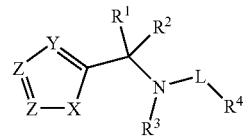

I or a pharmaceutically acceptable salt, hydrate, or prodrug thereof, wherein, each of $R^1$ and $R^2$ is independently selected from —H, halogen, trihalomethyl, —CN, —NO$_2$, —NH$_2$, —OR$^7$, —NR$^7$R$^7$, —S(O)$_{0-2}$R$^7$, —SO$_2$NR$^7$R$^7$, —CO$_2$R$^7$, —C(O)NR$^7$R$^7$, —N(R$^7$)SO$_2$R$^7$, —N(R$^7$)C(O)R$^7$, —N(R$^7$)CO$_2$R$^7$, —C(O)R$^7$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl; or combined, $R^1$ and $R^2$ are oxo;

$R^3$ is selected from —H, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

$R^4$ is selected from —H, —N(R$^5$)R$^6$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

X is selected from —O—, —N(R$^a$)—, and —S(O)$_{0-2}$—,

Y is =C(R$^b$)— or =N—;

one of Z is =C(C(=O)W)—, while the other Z is =C(R$^c$)— or =N—;

W is —OR$^7$ or —N(R$^5$)R$^6$;

L is selected from —C(=O)—, absent, —SO$_2$—, and —C(=S)—;

$R^5$ is —H or R$^6$;

$R^6$ is selected from optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl; or $R^5$ and $R^6$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P;

$R^7$ is —H or R$^8$;

$R^8$ is selected from optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

$R^7$ and $R^8$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P; and each of $R^a$, $R^b$, and $R^c$ is independently selected from —H, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl.

In one example, the compound is according to paragraph [0024], wherein one of Z is —C(=O)W, while the other Z is =C($R^c$)—.

In another example, the compound is according to paragraph [0025], wherein X is —S(O)$_{0-2}$— or —O—.

In another example, the compound is according to paragraph [0026], wherein X is —S— or —O—.

In another example, the compound is according to paragraph [0027], wherein W is —N($R^5$)$R^6$.

In another example, the compound is according to paragraph [0028], wherein Y is =N—.

In another example, the compound is according to paragraph [0029], wherein L is —C(=O)—.

In another example, the compound is according to paragraph [0030], wherein $R^1$ is —H.

In another example, the compound is according to paragraph [0031], wherein $R^2$ is —H.

In another example, the compound is according to paragraph [0032], wherein $R^4$ is —H.

In another example, the compound is according to paragraph [0033], wherein $R^4$ is optionally substituted $C_{1-6}$alkyl.

In another example, the compound is according to paragraph [0034], wherein $R^4$ is $C_{1-6}$alkyl substituted phenoxy.

In another example, the compound is according to paragraph [0033], wherein $R^4$ is N($R^5$)$R^6$.

In another example, the compound is according to paragraph [0036], wherein $R^6$ is optionally substituted aryl.

In another example, the compound is according to paragraph [0036], wherein $R^6$ is optionally substituted aryl $C_{1-6}$alkyl.

In another example, the compound is according to paragraph [0033], wherein $R^4$ is optionally substituted aryl In another example, the compound is according to paragraph [0033], wherein $R^4$ is optionally substituted aryl $C_{1-6}$alkyl.

In another example, the compound is according to paragraph [0033], wherein $R^4$ is optionally substituted heterocyclyl.

In another example, the compound is according to paragraph [0033], wherein $R^4$ is optionally substituted heterocyclyl $C_{1-6}$alkyl.

In another example, the compound is according to paragraph [0028], wherein $R^5$ is —H.

In another example, the compound is according to paragraph [0028], wherein $R^6$ is optionally substituted $C_{1-6}$alkyl.

In another example, the compound is according to paragraph [0028], wherein $R^6$ is optionally substituted aryl.

In another example, the compound is according to paragraph [0028], wherein $R^6$ is optionally substituted aryl $C_{1-6}$alkyl.

In another example, the compound is according to paragraph [0028], wherein $R^6$ is optionally substituted heterocyclyl.

In another example, the compound is according to paragraph [0028], wherein $R^6$ is optionally substituted heterocyclyl $C_{1-6}$alkyl.

In another example, the compound is according to paragraph [0028], wherein $R^5$ and $R^6$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P.

In another example, the compound is according to paragraph [0025], wherein $R^c$ is —H.

The present invention further comprises a compound for modulating ALK activity according to Formula II,

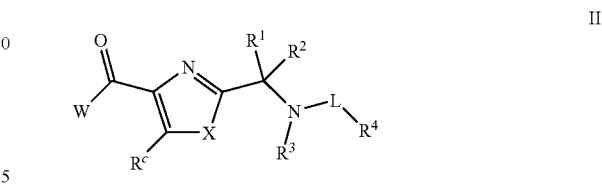

or a pharmaceutically acceptable salt, hydrate, or prodrug thereof, wherein, each of $R^1$ and $R^2$ is independently selected from —H, halogen, trihalomethyl, —CN, —NO$_2$, —NH$_2$, —OR$^7$, —NR$^7$R$^8$, —S(O)$_{0-2}$R$^7$, —SO$_2$NR$^7$R$^7$, —CO$_2$R$^7$, —C(O)NR$^7$R$^7$, —N(R$^7$)SO$_2$R$^7$, —N(R$^7$)C(O)R$^7$, —N(R$^7$)CO$_2$R$^7$, —C(O)R$^7$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl; or combined, $R^1$ and $R^2$ are oxo;

$R^3$ is selected from —H, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

$R^4$ is selected from —H, —N($R^5$)$R^6$, optionally substituted $C_{1-6}$alkyl, optionally substituted aryl, optionally substituted aryl $C_{1-6}$alkyl, optionally substituted heterocyclyl, and optionally substituted heterocyclyl $C_{1-16}$alkyl;

X is selected from —O—, —N($R^a$)—, and —S(O)$_{0-2}$—;

W is —OR$^7$ or —N($R^5$)$R^6$;

L is selected from —C(=O)—, absent, —SO$_2$—, and —C(=S)—;

$R^5$ is —H or $R^6$;

$R^6$ is selected from optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl; or $R^5$ and $R^6$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P;

$R^7$ is —H or $R^8$;

$R^8$ is selected from optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

$R^7$ and $R^8$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P; and each of $R^a$ and $R^c$ is independently selected from —H, optionally substituted $C_{1-6}$alkyl, optionally substituted aryl, optionally substituted aryl $C_{1-16}$alkyl, optionally substituted heterocyclyl, and optionally substituted heterocyclyl $C_{1-6}$alkyl.

In one example, the compound is according to paragraph [0051], wherein W is —N($R^5$)$R^6$.

In another example, the compound is according to paragraph [0052], wherein X is —S(O)$_{0-2}$— or —O—.

In another example, the compound is according to paragraph [0053], wherein X is —S— or —O—.

In another example, the compound is according to paragraph [0054], wherein L is —C(═O)—.

In another example, the compound is according to paragraph [0055], wherein $R^1$ is —H.

In another example, the compound is according to paragraph [0056], wherein $R^2$ is —H.

In another example, the compound is according to paragraph [0057], wherein $R^4$ is —H.

In another example, the compound is according to paragraph [0058], wherein $R^4$ is optionally substituted $C_{1-6}$alkyl.

In another example, the compound is according to paragraph [0059], wherein $R^4$ is $C_{1-6}$alkyl substituted phenoxy.

In another example, the compound is according to paragraph [0058], wherein $R^4$ is $N(R^5)R^6$.

In another example, the compound is according to paragraph [0061], wherein $R^6$ is optionally substituted aryl.

In another example, the compound is according to paragraph [0061], wherein $R^6$ is optionally substituted aryl $C_{1-6}$alkyl.

In another example, the compound is according to paragraph [0058], wherein $R^4$ is optionally substituted aryl.

In another example, the compound is according to paragraph [0058], wherein $R^4$ is optionally substituted aryl $C_{1-6}$alkyl.

In another example, the compound is according to paragraph [0058], wherein $R^4$ is optionally substituted heterocyclyl.

In another example, the compound is according to paragraph [0058], wherein $R^4$ is optionally substituted heterocyclyl $C_{1-6}$alkyl.

In another example, the compound is according to paragraph [0052], wherein $R^5$ is —H.

In another example, the compound is according to paragraph [0052], wherein $R^6$ is optionally substituted $C_{1-6}$alkyl.

In another example, the compound is according to paragraph [0052], wherein $R^6$ is optionally substituted aryl.

In another example, the compound is according to paragraph [0052], wherein $R^6$ is optionally substituted aryl $C_{1-6}$alkyl.

In another example, the compound is according to paragraph [0052], wherein $R^6$ is optionally substituted heterocyclyl.

In another example, the compound is according to paragraph [0052], wherein $R^6$ is optionally substituted heterocyclyl $C_{1-6}$alkyl.

In another example, the compound is according to paragraph [0052], wherein $R^5$ and $R^6$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P.

In another example, the compound is according to paragraph [0051], wherein $R^c$ is —H.

The present invention further comprises a compound for modulating ALK activity according to Formula III,

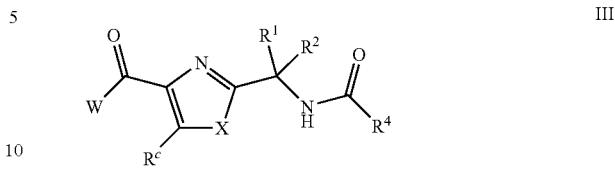

or a pharmaceutically acceptable salt, hydrate, or prodrug thereof, wherein,
each of $R^1$ and $R^2$ is independently selected from —H, halogen, trihalomethyl, —CN, —NO$_2$, —NH$_2$, —OR$^7$, —NR$^7$R$^8$, —S(O)$_{0-2}$R$^7$, —SO$_2$NR$^7$R$^7$, —CO$_2$R$^7$, —C(O)NR$^7$R$^7$, —N(R$^7$)SO$_2$R$^7$, —N(R$^7$)C(O)R$^7$, —N(R$^7$)CO$_2$R$^7$, —C(O)R$^7$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl; or
combined, $R^1$ and $R^2$ are oxo;
$R^4$ is selected from —H, —N(R$^5$)R$^6$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;
X is selected from —O—, —N(R$^a$)—, and —S(O)$_{0-2}$—,
W is —OR$^7$ or —N(R$^5$)R$^6$;
$R^5$ is —H or $R^6$;
$R^6$ is selected from optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl; or
$R^5$ and $R^6$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P;
$R^7$ is —H or $R^8$;
$R^8$ is selected from optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;
$R^7$ and $R^8$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P; and
each of $R^a$ and $R^c$ is independently selected from —H, optionally substituted $C_{1-6}$alkyl, optionally substituted aryl, optionally substituted aryl $C_{1-16}$alkyl, optionally substituted heterocyclyl, and optionally substituted heterocyclyl $C_{1-6}$alkyl.

In one example, the compound is according to paragraph [0076], wherein W is —N(R$^5$)R$^6$.

In another example, the compound is according to paragraph [0077], wherein X is —S(O)$_{0-2}$— or —O—.

In another example, the compound is according to paragraph [0078], wherein X is —S— or —O—.

In another example, the compound is according to paragraph [0079], wherein $R^1$ is —H.

In another example, the compound is according to paragraph [0080], wherein $R^2$ is —H.

In another example, the compound is according to paragraph [0081], wherein $R^4$ is optionally substituted $C_{1-6}$alkyl.

In another example, the compound is according to paragraph [0082], wherein $R^4$ is $C_{1-6}$alkyl substituted phenoxy.

In another example, the compound is according to paragraph [0081], wherein $R^4$ is $N(R^5)R^6$.

In another example, the compound is according to paragraph [0084], wherein $R^6$ is optionally substituted aryl.

In another example, the compound is according to paragraph [0084], wherein $R^6$ is optionally substituted aryl $C_{1-6}$alkyl.

In another example, the compound is according to paragraph [0081], wherein $R^4$ is optionally substituted aryl In another example, the compound is according to paragraph [0081], wherein $R^4$ is optionally substituted aryl $C_{1-6}$alkyl.

In another example, the compound is according to paragraph [0081], wherein $R^4$ is optionally substituted heterocyclyl.

In another example, the compound is according to paragraph [0081], wherein $R^4$ is optionally substituted heterocyclyl $C_{1-6}$alkyl.

In another example, the compound is according to paragraph [0077], wherein $R^5$ is —H.

In another example, the compound is according to paragraph [0077], wherein $R^6$ is optionally substituted $C_{1-6}$alkyl.

In another example, the compound is according to paragraph [0077], wherein $R^6$ is optionally substituted aryl.

In another example, the compound is according to paragraph [0077], wherein $R^6$ is optionally substituted aryl $C_{1-6}$alkyl.

In another example, the compound is according to paragraph [0077], wherein $R^6$ is optionally substituted heterocyclyl.

In another example, the compound is according to paragraph [0077], wherein $R^6$ is optionally substituted heterocyclyl $C_{1-6}$alkyl.

In another example, the compound is according to paragraph [0077], wherein $R^5$ and $R^6$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P.

In another example, the compound is according to paragraph [0076], wherein $R^c$ is —H.

In another example, the compound is according to paragraph [0024], selected from Table 1:

Lengthy table referenced here

US07973061-20110705-T00001

Please refer to the end of the specification for access instructions.

Another aspect of the invention is a pharmaceutical composition comprising a compound according to any of the preceding embodiments thereof and a pharmaceutically acceptable carrier.

Another aspect of the invention is a metabolite of the compound or the pharmaceutical composition according to any of the preceding embodiments thereof.

Another aspect of the invention is a method of modulating the in vivo activity of a kinase, the method comprising administering to a subject an effective amount of either the compound or the pharmaceutical composition according to any of the preceding embodiments thereof.

Another aspect of the invention is the method according to the preceding paragraph, wherein the kinase is ALK.

Another aspect of the invention is the method according to the preceding paragraph, wherein modulating the in vivo activity of the kinase comprises inhibition of said kinase.

Another aspect of the invention is a method of treating diseases or disorders associated with uncontrolled, abnormal, and/or unwanted cellular activities, the method comprising administering, to a mammal in need thereof, a therapeutically effective amount of either the compound or the pharmaceutical composition as described in any of the preceding embodiments thereof.

Another aspect of the invention is a method of screening for modulator of ALK, the method comprising combining either the compound according to any of the preceding embodiments thereof and at least one candidate agent and determining the effect of the candidate agent on the activity of ALK.

Another aspect of the invention is a method of inhibiting proliferative activity in a cell, the method comprising administering an effective amount of either the compound or the pharmaceutical composition according to any of the preceding embodiments thereof to a cell or a plurality of cells.

Another aspect of the invention is a method of making the compounds or pharmaceutical compositions according to any of the preceding embodiments thereof.

DEFINITIONS

As used in the present specification, the following words and phrases are generally intended to have the meanings as set forth below, except to the extent that the context in which they are used indicates otherwise or they are expressly defined to mean something different.

The symbol "-"means a single bond, "="means a double bond, "≡"means a triple bond. The symbol "⁀⁀⁀" refers to a group on a double-bond as occupying either position on the terminus of a double bond to which the symbol is attached; that is, the geometry, E- or Z-, of the double bond is ambiguous. When a group is depicted removed from its parent formula, the "∼" symbol will be used at the end of the bond which was theoretically cleaved in order to separate the group from its parent structural formula.

If a group "R" is depicted as "floating" on a ring system, as for example in the formula:

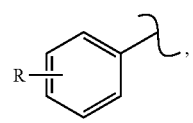

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

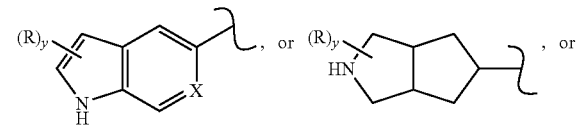

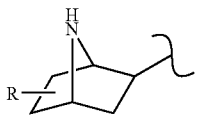

then, unless otherwise defined, a substituent "R" may reside on any atom of the fused ring system, assuming replacement of a depicted (for example the —NH— in the formula above), implied (for example as in the formula above, where the hydrogens are not shown but understood to be present), or expressly defined hydrogen (for example where in the formula above, "X" equals —CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When there are more than one such depicted "floating" groups, as for example in the formulae:

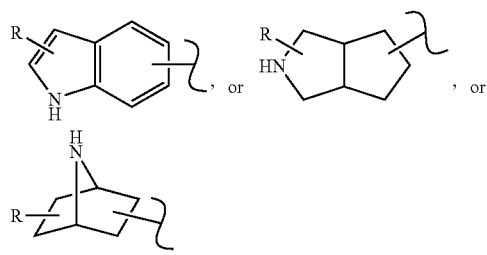

where there are two groups, namely, the "R" and the bond indicating attachment to a parent structure; then, unless otherwise defined, the "floating" groups may reside on any atoms of the ring system, again assuming each replaces a depicted, implied, or expressly defined hydrogen on the ring.

When a group "R" is depicted as existing on a ring system containing saturated carbons, as for example in the formula:

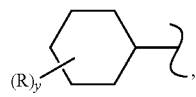

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

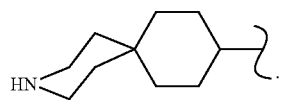

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-yne radicals; and for example, "propyl" or "$C_3$ alkyl" each include n-propyl, propenyl, and isopropyl.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —OCH$_2$CH$_2$OCH$_3$, and glycol ethers such as polyethyleneglycol and —O(CH$_2$CH$_2$O)$_x$CH$_3$, where x is an integer of between about two and about twenty, in another example, between about two and about ten, and in a further example between about two and about five. Another exemplary substituted alkoxy group is hydroxyalkoxy or —OCH$_2$(CH$_2$)$_y$OH, where y is for example an integer of between about one and about ten, in another example y is an integer of between about one and about four. Yet another exemplary substituted alkoxy group is arylalkoxy or heteroarylalkoxy, in these groups the alkyl portion of the alkoxy is substituted with an aryl or heteroaryl, the aryl or heteroaryl is preferably optionally substituted.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —NH$_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring radical. A phenylene, thus may have more than two groups attached, but is defined by the minimum of two groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as C$_{1-6}$ arylalkyl.

"Aryloxy" refers to a residue in which an aryl moiety is attached to a parent structure via an intervening oxygen, depicted in formula as —O—. Examples include phenyloxy, and naphthyloxy. "Substituted aryloxy" refers to an aryloxy, where the aryl portion of the aryloxy is substituted with the group or groups identified as substituents.

"Exo-alkenyl" refers to a double bond that emanates from an annular carbon, and is not within the ring system, for example the double bond depicted in the formula below.

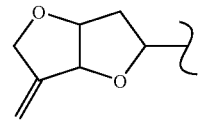

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S-(sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic.

"Heteroaryloxy" refers to a residue in which a heteroaryl moiety is attached to a parent structure via an intervening oxygen, depicted in formula as —O—. Examples include pyridyloxy, and pyrazinyloxy. "Substituted heteroaryloxy" refers to a heteroaryloxy, where the heteroaryl portion of the heteroaryloxy is substituted with the group or groups identified as substituents.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted aryl$C_{1-8}$ alkyl," optional substitution may occur on both the "$C_{1-8}$ alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitution are listed below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

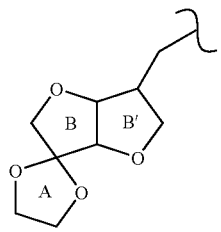

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl), optionally substituted aryl (for example, 4-hydroxyphenyl), optionally substituted arylalkyl (for example, 1-phenyl-ethyl), optionally substituted heterocyclylalkyl (for example, 1-pyridin-3-yl-ethyl), optionally substituted heterocyclyl (for example, 5-chloro-pyridin-3-yl or 1-methyl-piperidin-4-yl), optionally substituted alkoxy, alkylenedioxy (for example methylenedioxy), optionally substituted amino (for example, alkylamino and dialkylamino), optionally substituted amidino, optionally substituted aryloxy (for example, phenoxy), optionally substituted arylalkyloxy (for example, benzyloxy), carboxy (—CO$_2$H), carboalkoxy (that is, acyloxy or —OC(=O)R), carboxyalkyl (that is, esters or —CO$_2$R), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S(O$_2$)—H, —S(O$_2$)-(optionally substituted alkyl), —S(O$_2$)-optionally substituted aryl), —S(O$_2$)-(optionally substituted heterocyclyl), —S(O$_2$)-(optionally substituted alkoxy), —S(O$_2$)-optionally substituted aryloxy), and —S(O$_2$)-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Compounds were named using the nomenclature engine published by ACD/Labs of Toronto Canada—ACD/Name Batch 7.00 Release, Product v.7.10, Build 15 Sep. 2003.

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —OCH$_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—OCH$_2$-" is meant to mean not only "—OCH$_2$-" as drawn, but also "—CH$_2$O—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example ALK receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, ALK protein may be done in a number of ways. In one example, the candidate agent (the compound of the invention) is labeled, for example, with a fluorescent or radioactive moiety and binding determined directly. For example, thus may be done by attaching all or a portion of the ALK protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, ALK protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to ALK.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to ALK, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to ALK protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to ALK and thus is capable of binding to, and potentially modulating, the activity of the ALK. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to ALK with a higher affinity. Thus, if the candidate agent is labeled, the presence of the label on the support, coupled with a lack of competitor binding, may indicate the candidate agent is capable of binding to ALK.

It may be of value to identify the binding site of ALK. This can be done in a variety of ways. In one embodiment, once ALK has been identified as binding to the candidate agent, the ALK is fragmented or modified and the assays repeated to identify the necessary components for binding.

Modulation is tested by screening for candidate agents capable of modulating the activity of ALK comprising the steps of combining a candidate agent with ALK, as above, and determining an alteration in the biological activity of the ALK. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native ALK, but cannot bind to modified ALK.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

One of ordinary skill in the art would understand that certain crystallized, protein-ligand complexes, in particular ALK-ligand complexes, and their corresponding x-ray structure coordinates can be used to reveal new structural information useful for understanding the biological activity of ALK kinase's as described herein. As well, the key structural features of the aforementioned proteins, particularly, the shape of the ligand binding site, are useful in methods for designing or identifying selective modulators of ALK kinase's and in solving the structures of other proteins with similar features. Ligands of such complexes may include compounds of the invention as described herein.

As well, one of ordinary skill in the art would appreciate that such suitable x-ray quality crystals can be used as part of a method of identifying a candidate agent capable of binding to and modulating the activity of ALK kinases. Such methods may be characterized by the following aspects: a) introducing into a suitable computer program, information defining a ligand binding domain of a ALK kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for ALK kinase modulation, and determining whether said candidate agent modulates ALK kinase activity in the assay. Such methods may also include administering the candidate agent, determined to modulate ALK kinase activity, to a mammal suffering from a condition treatable by ALK kinase modulation, such as those described above.

Also, one skilled in the art would appreciate that compounds of the invention can be used in a method of evaluating the ability of a test agent to associate with a molecule or molecular complex comprising a ligand binding domain of a ALK kinase. Such a method may be characterized by the following aspects: a) creating a computer model of a ALK kinase binding pocket using structure coordinates obtained from suitable x-ray quality crystals of the ALK kinase, b) employing computational algorithms to perform a fitting operation between the test agent and the computer model of the binding pocket, and c) analyzing the results of the fitting operation to quantify the association between the test agent and the computer model of the binding pocket.

ABBREVIATIONS AND THEIR DEFINITIONS

The following abbreviations and terms have the indicated meanings throughout:
Ac=acetyl
ATP=adenosine triphosphate
BNB=4-bromomethyl-3-nitrobenzoic acid
Boc=t-butyloxy carbonyl
br=broad
Bu=butyl
C=degrees Celsius
c-=cyclo
CBZ=carbobenzoxy=benzyloxycarbonyl
d=doublet
dd=doublet of doublet
dt=doublet of triplet
DBU=diazabicyclo[5.4.0]undec-7-ere
DCM=dichloromethane=methylene chloride=$CH_2Cl_2$
DCE=dichloroethylene
DEAD=diethyl azodicarboxylate DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
EI=Electron Impact ionization
Et=ethyl
Fmoc=9-fluorenylmethoxycarbonyl
g=gram(s)
GC=gas chromatography
h or hr=hour(s)
HATU=0-(7-Azabenzotriazol-1-yl)-1,1,3,3-tetramethyluronium hexafluorophosphate
HMDS=hexamethyldisilazane
HOAc=acetic acid
HOBt=hydroxybenzotriazole
HPLC=high pressure liquid chromatography
L=liter(s)
M=molar or molarity
m=multiplet
Me=methyl
mesyl=methanesulfonyl
mg=milligram(s)
MHz=megahertz (frequency)
Min=minute(s)
mL=milliliter(s)
mM=millimolar
mmol=millimole(s)
mol=mole(s)
MS=mass spectral analysis
MTBE=methyl t-butyl ether
N=normal or normality
NBS=N-bromosuccinimide
NCS=N-chlorosuccinimide
nM=nanomolar
NMO=N-methylmorpholine oxide
NMR=nuclear magnetic resonance spectroscopy
PEG=polyethylene glycol
pEY=poly-glutamine, tyrosine
Ph=phenyl
PhOH=phenol
PfP=pentafluorophenol
PfPy=pentafluoropyridine
PPTS=pyridinium p-toluenesulfonate
Py=pyridine
PyBroP=bromo-tris-pyrrolidino-phosphonium hexafluorophosphate
q=quartet
RT=room temperature
Sat'd=saturated
s=singlet
s-=secondary
t-=tertiary
t or tr=triplet
TBDMS=t-butyldimethylsilyl
TES=triethylsilane
TFA=trifluoroacetic acid
THF=tetrahydrofuran
TMOF=trimethyl orthoformate
TMS=trimethylsilyl
tosyl=p-toluenesulfonyl
Trt=triphenylmethyl
uL=microliter(s)
uM=micromole(s) or micromolar Synthesis of Compounds The synthetic schemes below depict general synthetic routes for exemplary compounds of the invention and are not intended to be limiting. Specific examples are described subsequently to this general synthetic description. With the descriptions of general routes and the specific examples thereafter, one of ordinary skill in the art would be able to make compounds of the invention as described.

Schemes 1-3 show exemplary general synthetic strategies for making compounds according to Formulas I, II and III of the invention. In relation to the schemes, some substituents (e.g. $R^1$ through $R^7$) are not necessarily described as reactive partners in the synthetic reactions available to make compounds of the invention. This is done purely for simplification of description of synthesis in general. Such substituents may be appended to the scaffold of depicted formulae at any time during synthesis or may pre-exist on intermediates or starting materials used to make compounds of the invention, as would be understood by one of ordinary skill in the art. More specific examples are presented below to more fully describe the invention. One of ordinary skill in the art would appreciate that other compounds according to the schematic formulae can be made in analogous fashion, and that commercially available starting materials may be used in similar synthetic schemes in some cases to make compounds of the invention.

Scheme 1 depicts synthesis of compounds of the invention starting from appropriately functionalized α-amino amides. Amide 1 has a protecting group, P, on it's α-amine functionality. Protecting group P can be for example, a BOC-protecting group. In other examples, P can be a group that does not allow a free hydrogen on the α-amino nitrogen. Amide 1 can be converted to thioamide 2, for example using Lawessen's reagent. Both 1 and 2 are used to make exemplary compounds of the invention.

For example, compounds 1 and 2 are reacted with a 3-bromo pyruvate (e.g. bromo ethyl pyruvate), to make the corresponding oxazole 3 and thiazole 4, respectively. As depicted, protecting group P can be such that the aforementioned ring formation process does not remove P. In other embodiments, for example where P is BOC and no measures are taken to quench in situ acid formation, P may be removed to give the corresponding free-amino derivatives. The sulfur atom of 4 can be further oxidized to make analogous sulfoxide and sulfone compounds of the invention.

Schemes 1-3 describe synthesis via deprotection (removal of P) and derivitization of the amino-moiety of the compounds, followed by derivitization of the carboxy-moiety (—$OR^7$) of the compounds. One of ordinary skill in the art would understand that compounds of the invention can also be made via first derivatizing the carboxy-moiety followed by derivatization of the amino-moiety.

Also, Schemes 1-3 describe the synthesis of either oxazoles or thiazoles; however the invention also encompasses geometric isomers for example, isoxazoles. In some instances (as described in more detail in the examples below, commercially available starting materials (e.g. 5-(Boc-aminomethyl)isoxazole-3-carbozylic acid) were used to make such ring structures. Additionally, description in Schemes 2 and 3 only involves oxazole 3; however, syntheses using 4 or other 5-membered heterocycles of the invention are analogous as would be understood by one of ordinary skill in the art. Excellent resources for synthesis of five-membered heterocycles is described, for example, in "Handbook of Heterocyclic Chemistry," $2^{nd}$ Ed., by Alan R. Katritzky, and "Heterocyclic Chemistry." $3^{rd}$ Ed., by Thomas L. Gilchrist, both of which are incorporated by reference herein for all purposes.

Scheme 1

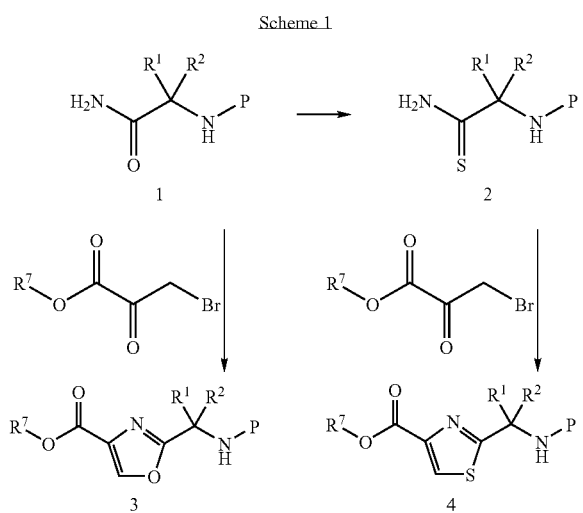

Referring to Scheme 2, protecting group P is removed (for example a BOC group is removed via appropriate TFA treatment) and the free-amino group is derivatized, to afforded compounds of the invention. In one example, the amino group is acylated to make amides 6. In another example, the amino group is acylated to make ureas 7. In one example, the amino group is reacted with an isothiocyanate to make thioureas 8. Typically, but not necessarily, the agent used to derivatize the amino group (for example any of the aforementioned acylating agent, isocyanate or isothiocyanate, whether commercially available or not) are appropriately functionalized so that further derivitization of the corresponding amide, urea or thiurea is not needed. However, the invention is not limited in this way. Further manipulation of the aforementioned groups also affords compounds of the invention. This further manipulation is performed previous to doing the chemistry as described in relation to Scheme 3, after doing the chemistry as described in relation to Scheme 3, or at another point in the synthetic sequence as appropriate, as would be understood by one of ordinary skill in the art.

Scheme 3 shows that compounds 6, 7 and 8 are further derivatized via conversion of the ester function to, for example, the correspond amides 9, 10 and 11, respectively. In a typical example, the ester is saponified followed by acidification to give the corresponding acid, or acidic hydrolysis of the ester is performed to give the free acid. The free acid may be converted, for example, to the corresponding acyl halide and combined with a primary or secondary amine, or alternatively the free acid is coupled to an amine via an amide forming reagent, for example HATU. Compounds 9, 10 and 11 can also be further derivatized to afford compounds of the invention.

Scheme 3

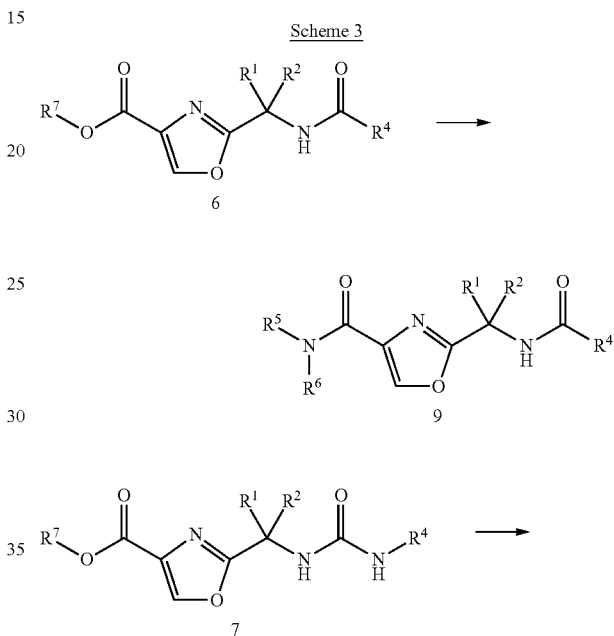

Scheme 2

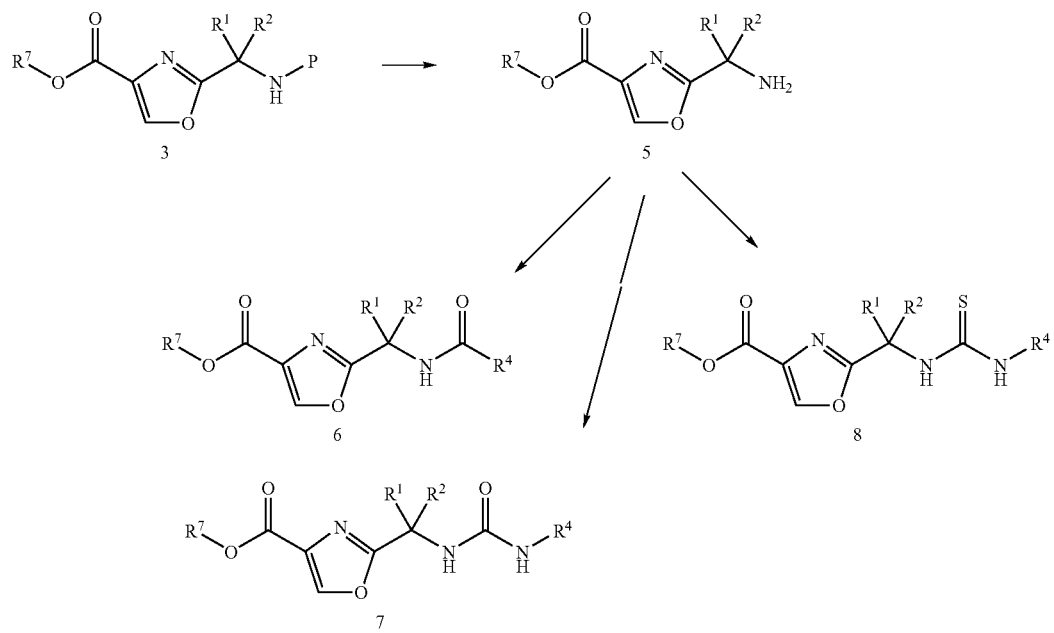

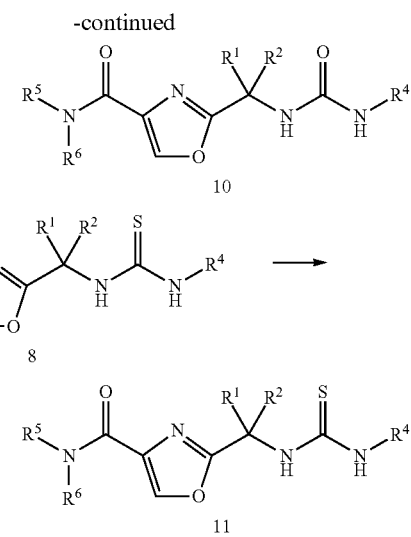

One of ordinary skill in the art would recognize that the descriptions associated with Schemes 1-3 are generalizations, and that there are other combinations of steps and approaches that can be used to make compounds of the invention. The examples that follow provide much more detailed descriptions of making exemplary compounds of the invention.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, but not necessarily, each example set out below describes a multi-step synthesis as outlined above.

Example 1

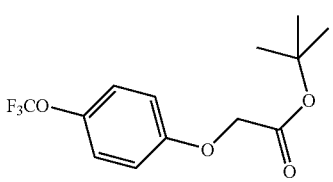

(4-Trifluoromethoxyphenoxy)-acetic acid tert-butyl ester: tert-Butyl bromoacetate was added to a stirring suspension of potassium carbonate (14.6 g, 106 mmol), 4-(trifluoromethoxy)phenol (15.7 g, 88 mmol) and DMF (50 mL). The reaction mixture was stirred for 12 hours. The mixture was diluted with EtOAc and water. The layers were separated and the aqueous layer was extracted with 3×EtOAc. The combined organic layers were washed with 5% aqueous lithium chloride and brine, dried over sodium sulfate, filtered, and reduced in vacuo to afford the title compound as a colorless oil: 1H NMR (400 MHz, d6-DMSO): 7.27 (d, 2H), 6.98 (d, 2H), 4.68 (s, 2H), 1.42 (s, 9H).

Example 2

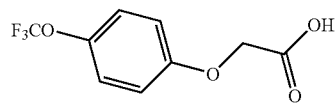

(4-Trifluoromethoxyphenoxy)-acetic acid: TFA (80 mL) was added to (4-trifluoromethoxyphenoxy)-acetic acid tert-butyl ester (25.8 g, 88 mmol). The mixture was stirred for three hours. The TFA was removed in vacuo affording the title compound as a white solid: MS (ESI-LCMS) for C9H6F3O4: 235 (M-H—).

Example 3

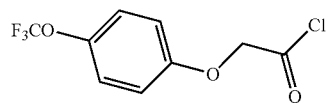

(4-Trifluoromethoxyphenoxy)-acetyl chloride: (4-Trifluoromethoxyphenoxy)-acetic acid (20.7 g, 88 mmol) was dissolved in thionyl chloride (100 mL). DMF (3 drops) was added to the solution. The solution was stirred for 14 hours. The thionyl chloride was removed in vacuo. The resulting oil was dissolved in dichloromethane, filtered through sodium sulfate and concentrate in vacuo to afford the title compound as a paste-like solid (21.8 g, 97% from the phenol): MS (EI-GCMS) for C9H6ClF3O3: 254 (M+).

Example 4

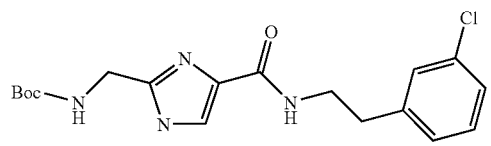

{4-[2-(3-Chlorophenyl)ethylcarbamoyl]thiazol-2-ylmethyl}carbamic acid tert-butyl ester: 2-(Boc-aminomethyl)thiazole-4-carboxylic acid (0.5 g, 1.9 mmol) and HATU (0.81 g, 2.1 mmol) were weighed into a flask. DMF (7 mL) and DIEA (0.68 mL, 3.9 mmol) were added. The mixture was stirred for 10 minutes. 2-(3-Chlorophenyl)ethylamine (0.3 g, 1.9 mmol) was added and reaction mixture was stirred for 12 hours. The mixture was diluted EtOAc and water. The layers were separated and the aqueous layer was extracted with 3×EtOAc. The combined organic layers were washed with 5% aqueous lithium chloride and brine, dried over sodium sulfate, filtered, and concentrated in vacuo. The material was purified by filtration through a plug of silica gel with 1:1 EtOAc:hexane to afford the title compound (0.73 g, 95%): $^1$H NMR (400 MHz, d6-DMSO): 8.42 (t, 1H), 8.10 (s, 1H), 7.85 (t, 1H), 7.27 (m, 3H), 7.16 (m, 1H), 4.38 (d, 2H), 3.46 (q, 2H), 2.82 (t, 2H), 1.39 (s, 9H); MS (ESI-LCMS) for C14H14ClN3O3S: 340 (MH-tBu+).

Example 5

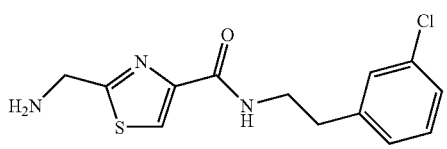

2-Aminomethyl-thiazole-4-carboxylic acid [2-(3-chlorophenyl)ethyl]amide: To a solution of {4-[2-(3-Chlorophenyl)ethylcarbamoyl]thiazol-2-ylmethyl}carbamic acid tert-butyl ester (0.73 g, 1.8 mmol) in methanol (10 mL) was added HCl in dioxane (4M solution, 10 mL). The mixture stirred for 12 hours. The methanol and dioxane were removed in vacuo and the resulting solid was vigorously mixed with 0.1 N NaOH and methylene chloride. The layers were separated and the aqueous layer was extracted with methylene chloride. The combined organic layers were washed with brine, dried over sodium sulfate, filtered, and concentrated in vacuo to afford the title compound as a solid. 1H NMR (400 MHz, d6-DMSO): 8.39 (br s, 1H), 8.08 (s, 1H) 7.25 (m, 4H), 4.00 (s, 2H), 3.48 (m, 2H), 2.84 (t, 2H), 2.41 (br s, 2H); MS (ESI-LCMS) for C13H14ClN3OS: 296 (MH+).

Example 6

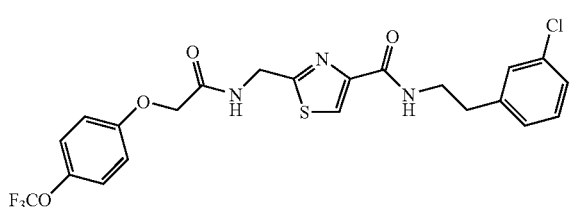

2-{[2-(4-Trifluoromethoxyphenoxy)-acetylamino]-methyl}thiazole-4-carboxylic acid [2-(3-chlorophenyl)-ethyl]amide: 2-Aminomethyl-thiazole-4-carboxylic acid [2-(3-chlorophenyl)ethyl]amide (0.54 g, 1.8 mmol) was dissolved in methylene chloride (15 mL). (4-Trifluoromethoxyphenoxy)-acetyl chloride (0.47 g, 1.8 mmol) was added followed by pyridine (0.3 mL, 4 mmol) and DMAP (0.02 g, 0.1 mmol). The mixture was stirred for 12 hours. Saturated, aqueous NH4Cl was added and the mixture was extracted with methylene chloride ×3. The combined organic extracts were washed with 1N HCl, saturated, aqueous NaHCO3, brine, dried over sodium sulfate, filtered and concentrated in vacuo. The material was purified by recrystallization from ethanol/diethyl ether to afford the title compound (0.65 g, 68% from the Boc protected amine): ¹H NMR (400 MHz, d6-DMSO): 9.08 (t, 1H), 8.40 (t, 1H), 8.10 (s, 1H), 7.27 (m, 5H), 7.17 (d, 1H), 7.06 (d, 2H), 4.65 (s, 2H), 4.62 (d, 2H), 3.48 (m, 2H), 2.84 (t, 2H); MS (ESI-LCMS) for C22H20ClF3N3O4S: 514 (MH+).

Example 7

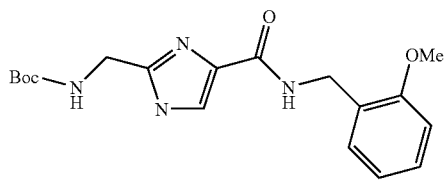

[4-(2-Methoxybenzylcarbamoyl)-thiazol-2-ylmethyl]-carbamic acid tert-butyl ester: Using an analogous synthetic procedure and substituting with alternative reagents (vide supra), the title compound was prepared (84%): ¹H NMR (400 MHz, d6-DMSO): 8.60 (t, 1H), 8.15 (s, 1H), 7.86 (t, 1H), 7.21 (m, 1H), 7.10 (d, 1H), 6.97 (d, 1H), 6.86 (m, 1H), 4.40 (m, 4H), 3.80 (s, 3H), 1.39 (s, 9H); MS (ESI-LCMS) for C14H16N3O4S: 322 (MH-tBu+).

Example 8

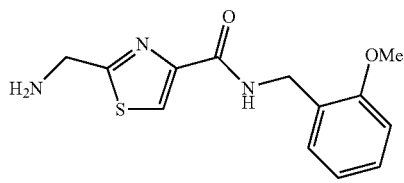

2-Aminomethyl-thiazole-4-carboxylic acid 2-methoxy-benxylamide: Using an analogous synthetic procedure (vide supra), the title compound was prepared (88%): ¹H NMR (400 MHz, d6-DMSO): 8.56 (t, 1H), 8.10 (s, 1H), 7.21 (t, 1H), 7.09 (d, 1H), 6.96 (d, 1H), 6.86 (t, 1H), 4.39 (d, 2H), 4.01 (s, 2H), 3.81 (s, 3H), 2.40 (br s, 2H); MS (ESI-LCMS) for C13H16N3O2S: 278 (MH+).

Example 9

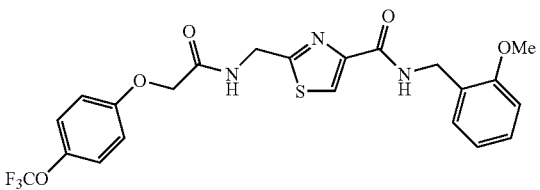

2-{2-(4-Trifluoromethoxy-phenoxy)-acetylamino]-methyl}-thiazole-4-carboxylic acid 2-methoxy-benzylamide: Using an analogous synthetic procedure (vide supra), the title compound was prepared (42% over two steps): ¹H NMR (400 MHz, d6-DMSO): 9.10 (t, 1H), 8.59 (t, 1H), 8.16 (s, 1H), 7.31 (d, 2H), 7.21 (m, 1H), 7.10 (m, 1H), 7.06 (d, 2H), 6.96 (d, 1H), 6.87 (t, 1H), 4.64 (m, 4H), 4.41 (d, 2H), 3.81 (s, 3H); MS (ESI-LCMS) for C22H21F3N3O5S: 496 (MH+).

Example 10

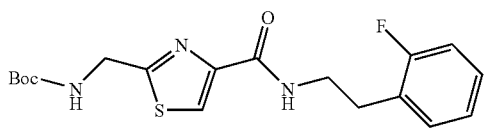

{4-[2-(2-Fluorophenyl)-ethylcarbamoyl]-thiazol-2-ylmethyl}carbamic acid tert-butyl ester: Using an analogous synthetic procedure and substituting with alternative reagents (vide supra), the title compound was prepared (91%): $^1$H NMR (400 MHz, $d_6$-DMSO): 8.46 (t, 1H), 8.09 (s, 1H), 7.85 (t, 1H), 7.25 (m, 2H), 7.11 (m, 2H), 4.38 (d, 2H), 3.46 (q, 2H), 2.85 (t, 2H), 1.39 (s, 9H); MS (ESI-LCMS) for $C_{14}H_{15}FN_3O_3S$: 324 (MH-tBu$^+$).

Example 11

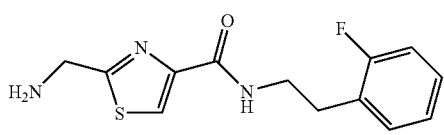

2-Aminomethyl-thiazole-4-carbocylic acid [2-(2-fluorophenyl)-ethyl]amide: Using an analogous synthetic procedure (vide supra), the title compound was prepared (81%): $^1$H NMR (400 MHz, $d_6$-DMSO): 8.41 (t, 1H), 8.05 (s, 1H), 7.25 (m, 2H), 7.11 (m 2H), 3.98 (s, 2H), 3.47 (q, 2H), 2.86 (t, 2H), 2.37 (br s, 2H); MS (ESI-LCMS) for $C_{13}H_{15}FN_3OS$: 280 (MH$^+$).

Example 12

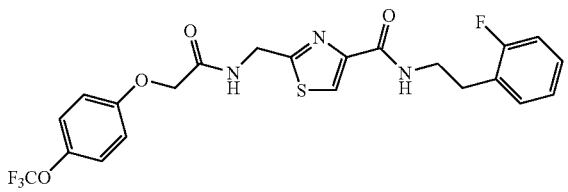

2-{[2-(4-Trifluoromethoxy-phenoxy)-acetylamino]-methyl}-thiazole-4-carboxylic acid [2-(2-fluoro-phenyl)-ethyl]-amide: Using an analogous synthetic procedure (vide supra), the title compound was prepared (72% over two steps): $^1$H NMR (400 MHz, $d_6$-DMSO): 9.08 (t, 1H), 8.45 (t, 1H), 8.10 (s, 1H), 7.26 (M, 4H), 7.09 (m, 4H), 4.65 (s, 2H), 4.61 (d, 2H), 3.47 (m, 2H), 2.86 (t, 2H); MS (ESI-LCMS) for $C_{22}H_{20}F_4N_3O_4S$: 498 (MH$^+$).

Example 13

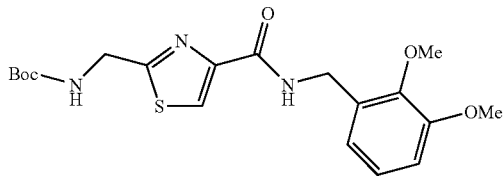

[4-(2,3-Dimethoxy-benzylcarbamoyl)-thiazol-2-ylmethyl]-carbamic acid tert-butyl ester: Using an analogous synthetic procedure and substituting with alternative reagents (vide supra), the title compound was prepared (82%): $^1$H NMR (400 MHz, $d_6$-DMSO): 8.64 (t, 1H), 8.15 (s, 1H), 7.85 (t, 1H), 6.95 (m, 2H), 6.78 (d, 1H), 4.44 (d, 2H), 4.40 (d, 2H), 3.77 (s, 3H), 3.74 (s, 3H), 1.39 (s, 9H); MS (ESI-LCMS) for $C_{15}H_{18}N_3O_5S$: 352 (MH-tBu$^+$).

Example 14

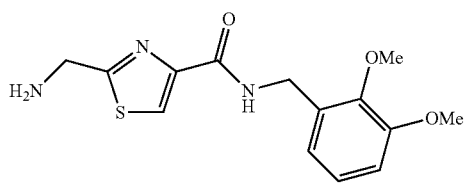

2-Aminomethyl-thiazole-4-carboxylic acid 2,3-dimethoxy-benzylamide: Using an analogous synthetic procedure (vide supra), the title compound was prepared (48% over two steps): $^1$H NMR (400 MHz, $d_6$-DMSO): 8.60 (t, 1H), 8.10 (s, 1H), 6.97 (m, 1H), 6.91 (dd, 1H), 6.78 (d, 1H), 4.44 (d, 2H), 4.01 (s, 2H), 3.78 (s, 3H), 3.75 (s, 3H); MS (ESI-LCMS) for $C_{14}H_{18}N_3O_3S$: 308 (MH$^+$).

Example 15

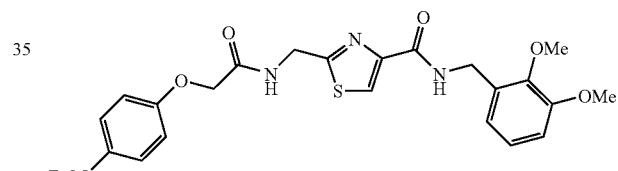

2-{[2-(4-Trifluoromethoxy-phenoxy)-acetylamino]-methyl}-thiazole-4-carboxylic acid 2,3-dimethoxy-benzylamide: Using an analogous synthetic procedure (vide supra), the title compound was prepared (70% over two steps): $^1$H NMR (400 MHz, $d_6$-DMSO): 9.09 (t, 1H), 8.63 (t, 1H), 8.15 (s, 1H), 7.31 (d, 2H), 7.06 (d, 2H), 6.95 (m, 2H), 6.78 (m, 1H), 4.64 (s, 2H), 4.63 (d, 2H), 4.45 (d, 2H), 3.78 (s, 3H), 3.75 (s, 3H); MS (ESI-LCMS) for $C_{23}H_{23}F_3N_3O_6S$: 526 (MH$^+$).

Example 16

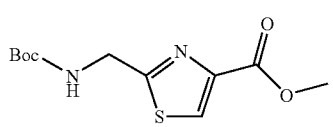

2-(tert-Butoxycarbonylamino-methyl)-thiazole-4-carboxylic acid methyl ester: 2-(Boc-aminomethyl)thiazole-4-carboxylic acid (0.5 g, 1.9 mmol) was dissolved in a benzene: methanol mixture (4:1, 7 mL) and (trimethylsilyl) diazomethane (2 M in hexane, 3.0 mL) was added dropwise. The reaction mixture was stirred for 12 hours. The reaction mixture was concentrated in vacuo to afford the product as a solid (0.42 g, 80%): ¹H NMR (400 MHz, d₆-DMSO): 8.42 (s, 1H), 7.84 (t, 1H), 4.37 (d, 2H), 3.80 (s, 3H), 1.39 (s, 9H); MS (ESI-LCMS) for C₆H₉N₂O₂S: 173 (MH-Boc⁺).

Example 17

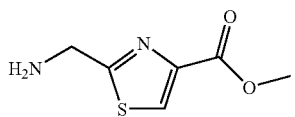

2-Aminomethyl-thiazole-4-carboxylic acid methyl ester: 2-(tert-Butoxycarbonylamino-methyl)-thiazole-4-carboxylic acid methyl ester (1.1 g, 3.9 mmol) was dissolved in methanol (15 mL). HCl in dioxane (4 M, 5 mL) was added. The mixture was stirred for 12 hours. The mixture was concentrated in vacuo, re-dissolved in methanol, and stirred with Bio-RAD AG 1-X8 resin (4 g, 20-50 mesh, hydroxide form, pre-washed with methanol and air dried) for 35 min. The mixture was filtered and the filtrate was concentrated in vacuo to afford the title compound (0.48 g, 73% over two steps): ¹H NMR (400 MHz, d₆-DMSO): 8.38 (s, 1H), 3.97 (s, 2H), 3.80 (s, 3H).

Example 18

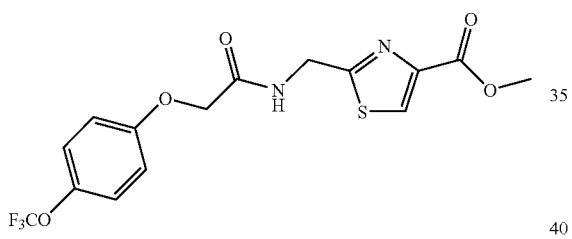

2-{[2-(4-Trifluoromethoxy-phenoxy)-acetylamino]-methyl}-thiazole-4-carboxylic acid methyl ester: Using an analogous synthetic procedure (vide supra), the title compound was prepared (64%): ¹H NMR (400 MHz, d₆-DMSO): 9.10 (t, 1H), 8.43 (s, 1H), 7.30 (d, 2H), 7.05 (d, 2H), 4.63 (s, 2H), 4.61 (d, 2H), 3.81 (s, 3H); MS (ESI-LCMS) for C₁₅H₁₄F₃N₂O₅S: 391 (MH⁺).

Example 19

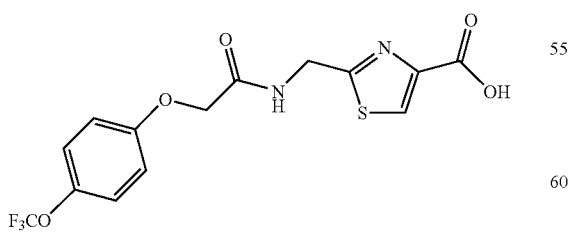

2-{[2-(4-Trifluoromethoxy-phenoxy)-acetylamino]-methyl}-thiazole-4-carboxylic acid: 2-{[2-(4-Trifluoromethoxy-phenoxy)-acetylamino]-methyl}-thiazole-4-carboxylic acid methyl ester (8.6 g, 22 mmol) was mixed with methanol (110 mL). NaOH (1.3 g, 33 mmol) was dissolved in water (110 mL) and added to the methanol solution. The reaction mixture was stirred for 12 hours. The mixture became homogenous after three hours. The methanol was removed in vacuo and the resulting slurry was acidified with 1 N HCl. The resulting slurry was extracted with EtOAc ×3. The combined organic extracts were dried over sodium sulfate, filtered, and concentrated in vacuo. The resulting solid was recrystallized from methanol to afford the title compound (7.1 g, 86%). ¹H NMR (400 MHz, d₆-DMSO): 9.08 (t, 1H), 8.33 (s, 1H), 7.31 (d, 2H), 7.06 (d, 2H), 4.63 (s, 2H), 4.61 (d, 2H); MS (ESI-LCMS) for C₁₄H₁₂F₃N₂O₅S: 377 (MH⁺).

Example 20

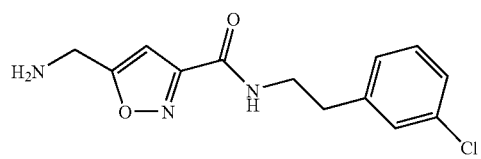

5-Aminomethyl-isoxazole-3-carboxylic acid [2-(3-chloro-phenyl)-ethyl]-amide: Using an analogous, two-step, synthetic procedure (vide supra), the title compound was prepared from 5-(Boc-aminomethyl)isoxazole-3-carbozylic acid: ¹H NMR (400 MHz, d₆-DMSO): 8.77 (t, 1H), 7.26 (m, 4H), 6.55 (s, 1H), 3.81 (s, 2H), 3.66 (d, 2H), 3.46 (q, 2H), 2.83 (t, 2H); MS (ESI-LCMS) for C₁₃H₁₅ClN₃O₂: 280 (MH⁺).

Example 21

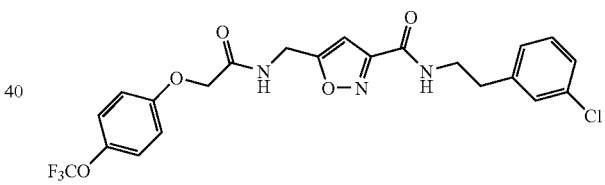

5-{[2-(4-Trifluoromethoxy-phenoxy)-acetylamino]-methyl}-isoxazole-3-carboxylic acid [2-(3-chloro-phenyl)-ethyl]-amide: Using an analogous synthetic procedure (vide supra), the title compound was prepared (39%, over 3 steps): ¹H NMR (400 MHz, d₆-DMSO): 8.85 (t, 1H), 8.81 (t, 1H), 7.27 (m, 5H), 7.16 (m, 1H), 7.05 (d, 2H), 6.56 (s, 1H), 4.61 (s, 2H), 4.50 (d, 2H), 3.46 (q, 2H), 2.83 (t, 2H); MS (ESI-LCMS) for C₂₂H₂₀ClF₃N₃O₅: 498 (MH⁺).

Example 22

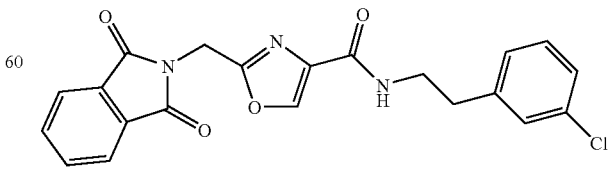

2-(1,3-Dioxo-1,3-dihydro-isoindol-2-ylmethyl)-oxazole-4-carboxylic acid [2-(3-chloro-phenyl)-ethyl]-amide: Using an analogous synthetic procedure (vide supra), the title compound was prepared from 2-(1,3-dioxo-1,3-dihydro-isoindol-2-ylmethyl)-oxazole-4-carboxylic acid: MS (ESI-LCMS) for $C_{21}H_{17}ClN_3O_4$: 410 (MH$^+$).

Example 23

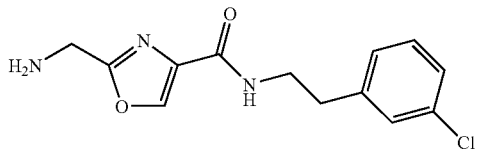

2-Aminomethyl-oxazole-4-carboxylic acid [2-(3-chlorophenyl)-ethyl]-amide: 2-(1,3-Dioxo-1,3-dihydro-isoindol-2-ylmethyl)-oxazole-4-carboxylic acid [2-(3-chloro-phenyl)-ethyl]-amide (0.75 g, 1.8 mmol) was dissolved in ethanol (5 mL). Hydrazine monohydrate (0.44 mL, 9.2 mmol) was added. The mixture was stirred for 12 hours. A white precipitate formed during the course of the reaction. The mixture was filtered and the solid was washed with methanol. The filtrate was reduced in vacuo to afford the title compound: $^1$H NMR (400 MHz, d$_6$-DMSO): 8.46 (s, 1H), 8.27 (t, 1H), 7.27 (m, 3H), 7.16 (m, 1H), 3.78 (s, 2H), 3.45 (m, 2H), 2.82 (t, 2H); MS (ESI-LCMS) for $C_{13}H_{14}ClN_3O_2$: 280 (MH$^+$).

Example 24

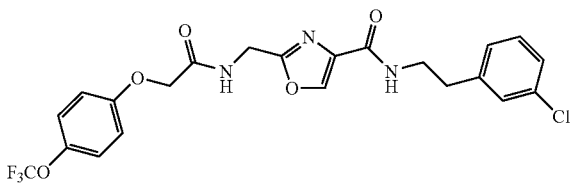

2-{[2-(4-Trifluoromethoxy-phenoxy)-acetylamino]-methyl}-oxazole-4-carboxylic acid [2-(3-chloro-phenyl)-ethyl]-amide: Using an analogous synthetic procedure (vide supra), the title compound was prepared (33%, over 3 steps): $^1$H NMR (400 MHz, d$_6$-DMSO): 8.86 (t, 1H), 8.50 (t, 1H), 8.29 (t, 1H), 7.26 (m, 5H), 7.15 (m, 1H), 7.05 (d, 2H), 4.59 (s, 2H), 4.47 (d, 2H), 3.45 (q, 2H), 2.82 (t, 2H); MS (ESI-LCMS) for $C_{22}H_{19}ClF_3N_3O_5$: 498 (MH$^+$).

Example 25

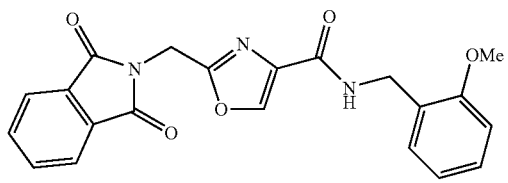

2-(1,3-Dioxo-1,3-dihydro-isoindol-2-ylmethyl)-oxazole-4-carboxylic acid 2-methoxy-benzylamide: Using an analogous synthetic procedure (vide supra), the title compound was prepared: MS (ESI-LCMS) for $C_{21}H_{18}N_3O_5$: 392 (MH$^+$).

Example 26

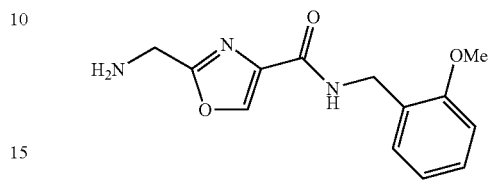

2-Aminomethyl-oxazole-4-carboxylic acid 2-methoxy-benzylamide: Using an analogous synthetic procedure (vide supra), the title compound was prepared: $^1$H NMR (400 MHz, d$_6$-DMSO): 8.51 (s, 1H), 8.46 (t, 1H), 7.21 (t, 1H), 7.08 (d, 1H), 6.96 (d, 1H), 6.87 (t, 1H), 4.37 (d, 2H), 3.81 (s, 3H), 3.80 (s, 2H); MS (ESI-LCMS) for $C_{13}H_{16}N_3O_3$: 262 (MH$^+$).

Example 27

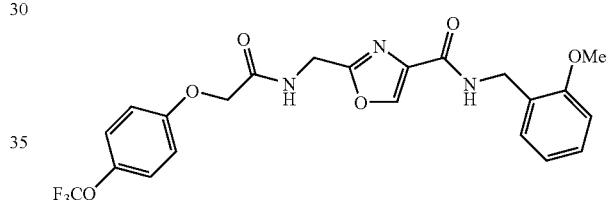

2-{[2-(4-Trifluoromethoxy-phenoxy)-acetylamino]-methyl}-oxazole-4-carboxylic acid 2-methoxy-benzylamide: Using an analogous synthetic procedure (vide supra), the title compound was prepared (44%, over 3 steps): $^1$H NMR (400 MHz, d$_6$-DMSO): 8.88 (t, 1H), 8.56 (s, 1H), 8.49 (t, 1H), 7.30 (d, 2H), 7.21 (m, 1H), 7.07 (m, 3H), 6.96 (d, 1H), 6.86 (m, 1H), 4.60 (s, 2H), 4.50 (d, 2H), 4.37 (d, 2H), 3.80 (s, 3H); MS (ESI-LCMS) for $C_{22}H_{21}F_3N_3O_6$: 480 (MH$^+$).

Example 28

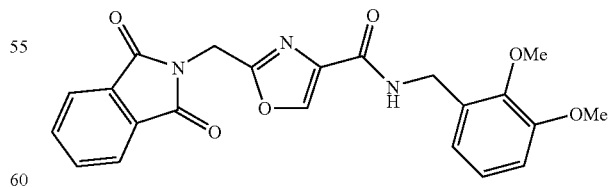

2-(1,3-Dioxo-1,3-dihydro-isoindol-2-ylmethyl)-oxazole-4-carboxylic acid 2,3-dimethoxy-benzylamide: Using an analogous synthetic procedure (vide supra), the title compound was prepared: MS (ESI-LCMS) for $C_{22}H_{20}N_3O_6$: 422 (MH$^+$).

Example 29

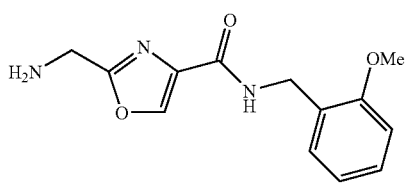

2-Aminomethyl-oxazole-4-carboxylic acid 2-methoxy-benzylamide: Using an analogous synthetic procedure (vide supra), the title compound was prepared: $^1$H NMR (400 MHz, $d_6$-DMSO): 8.51 (t, 1H), 8.50 (s, 1H), 6.98 (m, 1H), 6.92 (dd, 1H), 6.77 (dd, 1H), 4.42 (d, 2H), 3.79 (s, 2H), 3.78 (s, 3H), 3.74 (s, 3H); MS (ESI-LCMS) for $C_{14}H_{18}N_3O_4$: 292 (MH$^+$).

Example 30

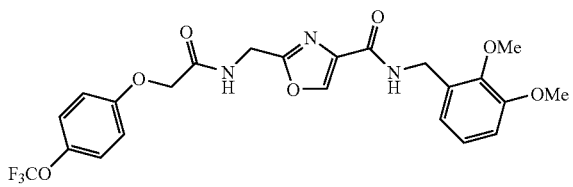

2-{[2-(4-Trifluoromethoxy-phenoxy)-acetylamino]-methyl}-oxazole-4-carboxylic acid 2,3-dimethoxy-benzylamide: Using an analogous synthetic procedure (vide supra), the title compound was prepared (49%, over 3 steps): $^1$H NMR (400 MHz, $d_6$-DMSO): 8.88 (t, 1H), 8.55 (m, 2H), 7.30 (m, 2H), 7.05 (d, 2H), 6.98 (m, 1H), 6.92 (m, 1H), 6.76 (m, 1H), 4.60 (s, 2H), 4.49 (d, 2H), 4.42 (d, 2H), 3.78 (s, 3H), 3.74 (s, 3H); MS (ESI-LCMS) for $C_{23}H_{23}F_3N_3O_7$: 510 (MH$^+$).

Example 31

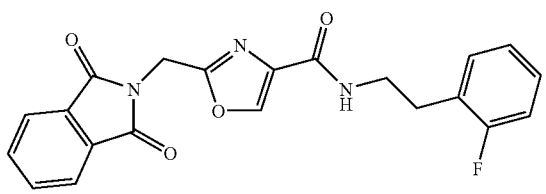

2-(1,3-Dioxo-1,3-dihydro-isoindol-2-ylmethyl)-oxazole-4-carboxylic acid [2-(2-fluoro-phenyl)-ethyl]-amide: Using an analogous synthetic procedure (vide supra), the title compound was prepared: MS (ESI-LCMS) for $C_{21}H_{17}FN_3O_4$: 394 (MH$^+$).

Example 32

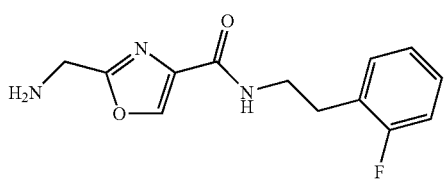

2-Aminomethyl-oxazole-4-carboxylic acid [2-(2-fluoro-phenyl)-ethyl]-amide: Using an analogous synthetic procedure (vide supra), the title compound was prepared: $^1$H NMR (400 MHz, $d_6$-DMSO): 8.45 (s, 1H), 8.31 (t, 1H), 7.25 (m, 2H), 7.11 (m, 2H), 3.78 (s, 2H), 3.44 (q, 2H), 2.84 (t, 2H).

Example 33

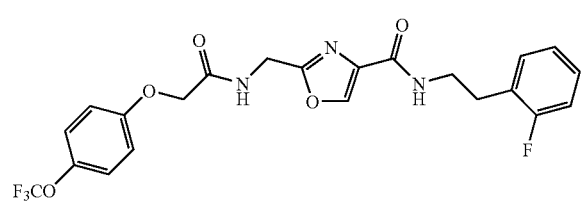

2-{[2-(4-Trifluoromethoxy-phenoxy)-acetylamino]-methyl}-oxazole-4-carboxylic acid [2-(2-fluoro-phenyl)-ethyl]-amide: Using an analogous synthetic procedure (vide supra), the title compound was prepared (47%, over 3 steps): $^1$H NMR (400 MHz, $d_6$-DMSO): 8.87 (t, 1H), 8.49 (s, 1H), 8.33 (t, 1H), 7.26 (m, 4H), 7.09 (m, 4H), 4.60 (s, 2H), 4.47 (d, 2H), 3.44 (q, 2H), 2.84 (t, 2H); MS (ESI-LCMS) for $C_{22}H_{20}F_4N_3O_5$: 482 (MH$^+$).

Example 34

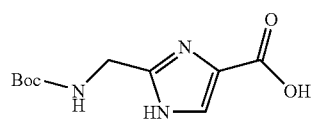

2-(tert-Butoxycarbonylamino-methyl)-1H-imidazole-4-carboxylic acid: Di-tert-butylpyrocarbonate (2.7 mL, 11.8 mmol) was added to a stirring solution of 2-(aminomethyl)imidazole-4-carboxylic acid (1.0 g, 5.9 mmol) and DIEA (2.2 mL, 12 mmol) in dioxane (20 mL). The reaction mixture was allowed to stir for 48 hours. The dioxane was removed in vacuo and the resulting residue was dissolved in methylene chloride, washed with 1 N HCl and saturated sodium bicarbonate, dried over sodium sulfate, filtered, and concentrated in vacuo. The crude material was dissolved in methanol (20 mL). NaOH (2.4 g, 59 mmol) was dissolved in water (20 mL) and added to the methanolic solution. The reaction mixture was heated and allowed to stir for 12 hours. The methanol was removed in vacuo and the aqueous solution was acidified with 1 N HCl and extracted with EtOAc ×3. The combined organic extracts were dried over sodium sulfate, filtered, and concentrated in vacuo to afford the title compound (1.3 g, 91%): $^1$H NMR (400 MHz, $d_6$-DMSO): 7.32 (s, 1H), 6.91 (br s, 1H), 4.09 (d, 2H), 1.38 (s, 9H); MS (ESI-LCMS) for $C_{10}H_{16}N_3O_4$: 242 (MH$^+$).

Example 35

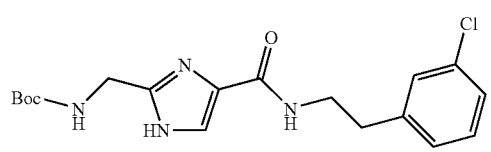

{4-[2-(3-Chloro-phenyl)-ethylcarbamoyl]-1H-imidazol-2-ylmethyl}-carbamic acid tert-butyl ester: Using an analogous synthetic procedure (vide supra), the title compound was prepared (39%): MS (ESI-LCMS) for $C_{18}H_{24}ClN_4O_3$: 379 (MH+).

Example 36

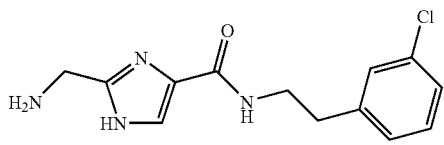

2-Aminomethyl-1H-imidazole-4-carboxylic acid [2-(3-chloro-phenyl)-ethyl]-amide: Using an analogous synthetic procedure (vide supra), the title compound was prepared: MS (ESI-LCMS) for $C_{13}H_{16}ClN_4O$: 279 (MH+).

Example 37

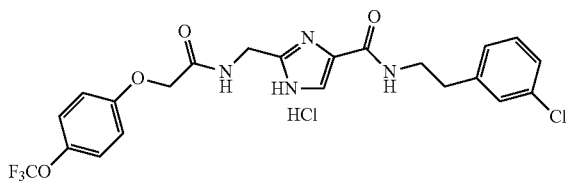

2-{[2-(4-Trifluoromethoxy-phenoxy)-acetylamino]-methyl}-1H-imidazole-4-carboxylic acid [2-(3-chloro-phenyl)-ethyl]-amide Hydrochloride: Using an analogous synthetic procedure (vide supra), the title compound was prepared. The material was purified by HPLC, basified and then treated with HCl in dioxane to afford the HCl salt: $^1$H NMR (400 MHz, $d_6$-DMSO): 8.81 (br s, 1H), 7.89 (br s, 1H), 7.30 (m, 6H), 7.20 (m, 1H), 7.09 (d, 2H), 4.61 (s, 2H), 4.55 (d, 2H), 3.69 (m, 2H), 2.84 (t, 2H); MS (ESI-LCMS) for $C_{22}H_{21}ClF_3N_4O_4$: 497 (MH+).

Example 38

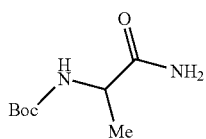

(1-Carbamoyl-ethyl)-carbamic acid tert-butyl ester: DL-N-Boc-alanine (5.0 g, 26.4 mmol), di-tert-butylpyrocarbonate (7.9 mL, 34 mmol), and ammonium bicarbonate (2.5 g, 32 mmol) were stirred together in acetonitrile (101 mL). Pyridine (1.3 mL, 16 mmol) was added. The mixture stirred for 12 hours. Water was added and then the acetonitrile was removed in vacuo. The resulting slurry was filtered. The solid was collected, dissolved in methylene chloride and methanol (90:10), dried over sodium sulfate, filtered, and concentrated in vacuo to afford the title compound (2.7 g, 55%): $^1$H NMR (400 MHz, $d_6$-DMSO): 7.20 (br s, 1H), 6.90 (br s, 1H), 6.77 (d, 1H), 3.86 (quintet, 1H), 1.37 (s, 9H), 1.15 (d, 3H).

Example 39

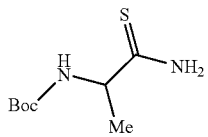

(1-Thiocarbamoyl-ethyl)-carbamic acid tert-butyl ester: (1-Carbamoyl-ethyl)-carbamic acid tert-butyl ester (8.0 g, 42 mmol) was dissolved in methylene chloride (85 mL), Lawessen's reagent was added (11.0 g, 27.mmol2). The mixture was stirred for 3 days. Water was added and the layers were separated. The aqueous layer was extracted with methylene chloride ×3. The combined organic layers were dried over sodium sulfate, filtered, and concentrated in vacuo. The resulting solid was filtered through a plug of silica using 1:3 EtOAc:hexane. The title compound was obtained as a mixture with trace amounts of Lawessen's reagent and used without further purification: $^1$H NMR (400 MHz, $d_6$-DMSO): 9.54 (br s, 1H), 9.07 (br s, 1H), 6.83 (d, 1H), 4.23 (quintet, 1H), 1.37 (s, 9H), 1.23 (d, 3H); MS (ESI-LCMS) for $C_8H_{17}N_2O_2S$: 205 (MH+).

Example 40

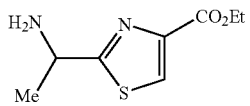

2-(1-Amino-ethyl)-thiazole-4-carboxylic acid ethyl ester: (1-Thiocarbamoyl-ethyl)-carbamic acid tert-butyl ester (8.7 g, 42.5 mmol) and ethyl bromopyruvate (90% Tech., 9.21 g, 42.5 mmol) were heated at reflux in ethanol (200 mL) for 12 hours. The ethanol was removed in vacuo and the residue was purified by flash chromatography (5:95 MeOH:$CH_2Cl_2$) to afford the title compound (1.24 g, 15% over two steps): $^1$H NMR (400 MHz, $d_6$-DMSO): 8.37 (s, 1H), 4.28 (qd, 2H), 4.24 (q, 1H), 2.60 (br s, 2H), 1.37 (d, 3H), 1.29 (t, 3H); MS (ESI-LCMS) for $C_8H_{13}N_2O_2S$: 201 (MH+).

Example 41

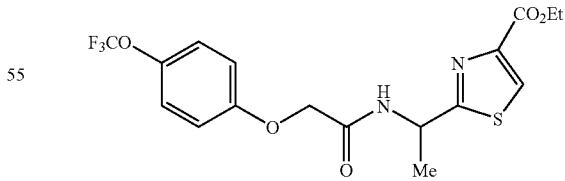

2-{1-[2-(4-Trifluoromethoxy-phenoxy)-acetylamino]-ethyl}-thiazole-4-carboxylic acid ethyl ester: Using an analogous synthetic procedure (vide supra), the title compound was prepared (78%): $^1$H NMR (400 MHz, $d_6$-DMSO): 9.02 (d, 1H), 8.43 (s, 1H), 7.32 (d, 2H), 7.06 (d, 2H), 5.28 (quintet, 1H), 4.64 (d, 2H), 4.30 (q, 2H), 1.56 (d, 3H), 1.30 (t, 3H); MS (ESI-LCMS) for $C_{17}H_{18}F_3N_2O_5S$: 419 (MH+).

Example 42

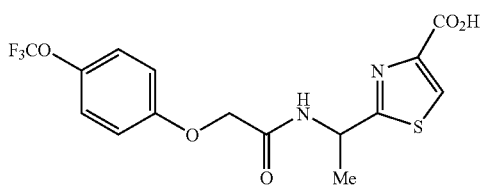

2-{1-[2-(4-Trifluoromethoxy-phenoxy)-acetylamino]-ethyl}-thiazole-4-carboxylic acid: Using an analogous synthetic procedure (vide supra), the title compound was prepared: MS (ESI-LCMS) for $C_{15}H_{12}F_3N_2O_5S$: 389 (M-H—).

Example 43

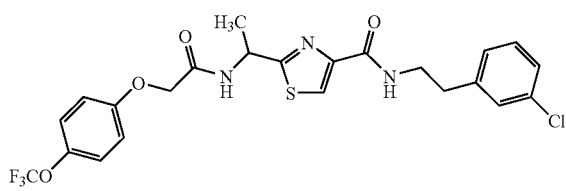

2-{1-[2-(4-Trifluoromethoxy-phenoxy)-acetylamino]-ethyl}-thiazole-4-carboxylic acid [2-(3-chloro-phenyl)-ethyl]-amide: Using an analogous synthetic procedure (vide supra), the title compound was prepared (52% over two steps): $^1$H NMR (400 MHz, $d_6$-DMSO): 9.00 (d, 1H), 8.36 (t, 1H), 8.12 (s, 1H), 7.32 (m, 4H), 7.26 (m, 1H), 7.20 (m, 1H), 7.06 (d, 2H), 5.27 (quintet, 1H), 4.64 (s, 2H), 3.49 (q, 2H), 2.85 (t, 2H), 1.58 (d, 3H); MS (ESI-LCMS) for $C_{23}H_{22}ClF_3N_3O_4S$: 528 (MH$^+$).

Example 44

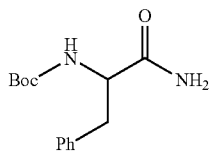

(1-Carbamoyl-2-phenyl-ethyl)-carbamic acid tert-butyl ester: Using an analogous synthetic procedure (vide supra), the title compound was prepared (67%): $^1$H NMR (400 MHz, $d_6$-DMSO): 7.36 (br s, 1H), 7.24 (m, 5H), 7.17 (br s, 1H), 6.80 (d, 1H), 4.06 (m, 1H), 2.94 (dd, 1H), 2.71 (dd, 1H), 1.42 (s, 9H).

Example 45

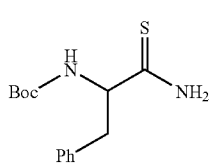

(2-Phenyl-1-thiocarbamoyl-ethyl)-carbamic acid tert-butyl ester: Using an analogous synthetic procedure (vide supra), the title compound was prepared: MS (ESI-LCMS) for $C_{10}H_{13}N_2O_2S$: 225 (MH-tBu$^+$).

Example 46

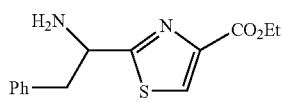

2-(1-Amino-2-phenyl-ethyl)-thiazole-4-carboxylic acid ethyl ester: Using an analogous synthetic procedure (vide supra), the title compound was prepared: MS (ESI-LCMS) for $C_{14}H_{17}N_2O_2S$: 277 (MH$^+$).

Example 47

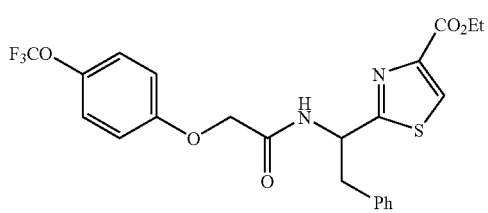

2-{2-Phenyl-1-[2-(4-trifluoromethoxy-phenoxy)-acetylamino]-ethyl}-thiazole-4-carboxylic acid ethyl ester: Using an analogous synthetic procedure (vide supra), the title compound was prepared (5% over 3 steps): $^1$H NMR (400 MHz, $d_6$-DMSO): 9.04 (d, 1H), 8.44 (s, 1H), 7.24 (m, 7H), 6.87 (d, 2H), 5.40 (m, 1H), 4.50 (s, 2H), 4.31 (q, 2H), 3.36 (dd, 1H), 3.18 (dd, 1H), 1.31 (t, 3H); MS (ESI-LCMS) for $C_{23}H_{22}F_3N_2O_5S$: 495 (MH$^+$).

Example 48

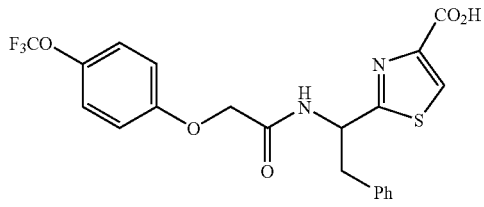

2-{2-Phenyl-1-[2-(4-trifluoromethoxy-phenoxy)-acetylamino]-ethyl}-thiazole-4-carboxylic acid: Using an analogous synthetic procedure (vide supra), the title compound was prepared: MS (ESI-LCMS) for $C_{21}H_{18}F_3N_2O_5S$: 467 (MH$^+$).

Example 49

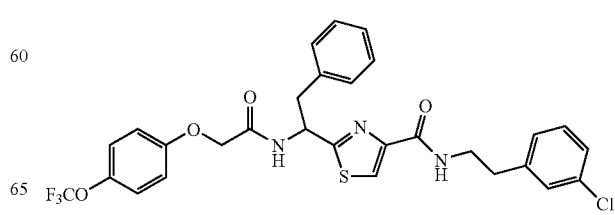

2-{2-Phenyl-1-[2-(4-trifluoromethoxy-phenoxy)-acetylamino]-ethyl}-thiazole-4-carboxylic acid [2-(3-chlorophenyl)-ethyl]-amide: Using an analogous synthetic procedure (vide supra), the title compound was prepared: $^1$H NMR (400 MHz, d$_6$-DMSO): 8.98 (d, 1H), 8.38 (t, 1H), 8.14 (s, 1H), 7.25 (m, 1H), 6.88 (d, 2H), 5.40 (m, 1H), 4.51 (s, 2H), 3.49 (m, 3H), 3.17 (dd, 1H), 2.86 (t, 2H); MS (ESI-LCMS) for C$_{29}$H$_{26}$ClF$_3$N$_3$O$_4$S: 604 (MH$^+$).

Example 50

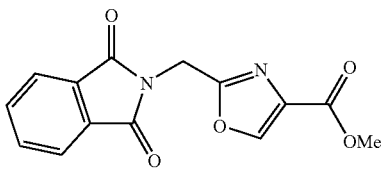

2-(1,3-Dioxo-1,3-dihydro-isoindol-2-ylmethyl)-oxazole-4-carboxylic acid methyl ester: Using an analogous synthetic procedure (vide supra), the title compound was prepared: $^1$H NMR (400 MHz, d$_6$-DMSO): 8.86 (s, 1H), 7.96 (m, 2H), 7.91 (m, 2H), 4.99 (s, 2H), 3.77 (s, 3H); MS (ESI-LCMS) for C$_{14}$H$_{11}$N$_2$O$_5$: 287 (MH$^+$).

Example 51

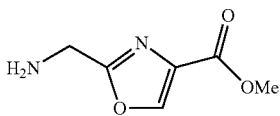

2-Aminomethyl-oxazole-4-carboxylic acid methyl ester: Using an analogous synthetic procedure (vide supra), the title compound was prepared. Title compound was obtained as a mixture and used without further purification: $^1$H NMR (400 MHz, d$_6$-DMSO): 9.42 (br s, 2H), 8.46 (s, 1H), 3.79 (d, 2H), 3.77 (s, 3H).

Example 52

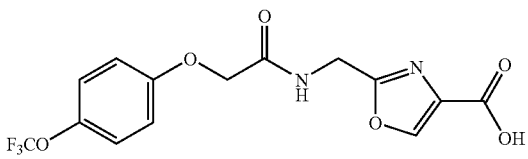

2-{[2-(4-Trifluoromethoxy-phenoxy)-acetylamino]-methyl}-oxazole-4-carboxylic acid: Using an analogous synthetic procedure (vide supra), the title compound was prepared (19% over 4 steps): $^1$H NMR (400 MHz, d$_6$-DMSO): 8.91 (t, 1H), 8.70 (s, 1H), 7.33 (d, 2H), 7.08 (d, 2H), 4.62 (s, 2H), 4.49 (d, 2H); MS (ESI-LCMS) for C$_{14}$H$_{12}$F$_3$N$_2$O$_6$: 361 (MH$^+$).

Example 53

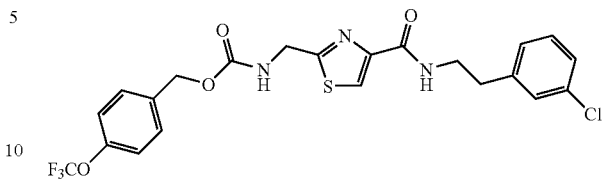

{4-[2-(3-Chloro-phenyl)-ethylcarbamoyl]-thiazol-2-ylmethyl}-carbamic acid 4-trifluoromethoxy-benzyl ester: 4-Nitrophenylchloroformate (0.1 g, 0.5 mmol) was added to a stirring solution of 4-(trifluoromethoxy)benzyl alcohol (0.09 g, 0.5 mmol), pyridine (0.07 mL, 0.9 mmol), and methylene chloride (2 mL). DMAP (6 mg) was added and the mixture was stirred for 12 hours. The mixture was diluted with saturated ammonium chloride and extracted 3× with methylene chloride. The combined organic layers were washed with 0.5 N NaHSO$_4$ and brine, dried over sodium sulfate, filtered, and concentrated in vacuo. The crude material was purified by flash chromatography (EtOAc/hexane). The 4-nitrophenyl-carbamate was mixed with 2-aminomethyl-thiazole-4-carboxylic acid [2-(3-chlorophenyl)ethyl]amide hydrochloride (0.14 g, 0.4 mmol) and DIEA (0.2 mL) in DMF (5 mL). The mixture was stirred for 12 hours. The mixture was diluted EtOAc and water. The layers were separated and the aqueous layer was extracted with 3×EtOAc. The combined organic layers were washed with 5% aqueous lithium chloride and brine, dried over sodium sulfate, filtered, and concentrated in vacuo. The material was purified by flash chromatography (EtOAc/hexane) to afford the title compound (0.11 g, 50%): $^1$H NMR (400 MHz, d$_6$-DMSO): 8.42 (t, 1H), 8.30 (t, 1H), 8.11 (s, 1H), 7.48 (d, 2H), 7.36 (d, 2H), 7.27 (m, 3H), 7.17 (d, 1H), 5.11 (s, 2H), 4.49 (d, 2H), 3.48 (m, 2H), 2.84 (t, 2H); MS (ESI-LCMS) for C$_{22}$H$_{20}$ClF$_3$N$_3$O$_4$S: 514 (MH$^+$).

Example 54

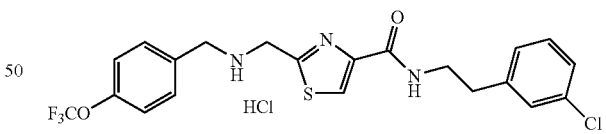

2-[(4-Trifluoromethoxy-benzylamino)-methyl]-thiazole-4-carboxylic acid [2-(3-chloro-phenyl)-ethyl]-amide hydrochloride: 2-Aminomethyl-thiazole-4-carboxylic acid [2-(3-chlorophenyl)ethyl]amide hydrochloride (0.10 g, 0.3 mmol) and 4-(trifluoromethoxy)benzyl amine (0.06 g, 0.3 mmol) were mixed with sodium cyanoborohydride (1 M in THF, 0.6 mL), ethanol (5 mL), and a catalytic amount of acetic acid (2 drops). The mixture was heated at reflux for 24 hours. The mixture was concentrated in vacuo, diluted with water and extracted with methylene chloride. The combined organic layers were washed with sodium carbonate and brine, dried over sodium sulfate, filtered, and concentrated in vacuo. The crude amine was purified by flash chromatography (EtOAc/ hexane), treated with HCl in dioxane, and concentrated in vacuo to afford the title compound: $^1$H NMR (400 MHz, d$_6$-DMSO): 9.83 (br s, 2H), 8.43 (t, 1H), 8.32 (s, 1H), 7.66 (d, 2H), 7.44 (d, 2H), 7.25 (m, 4H), 4.58 (s, 2H), 4.37 (s, 2H), 3.53 (m, 2H), 2.86 (t, 2H); MS (ESI-LCMS) for C$_{21}$H$_{20}$ClF$_3$N$_3$O$_2$S: 470 (MH$^+$).

Example 55

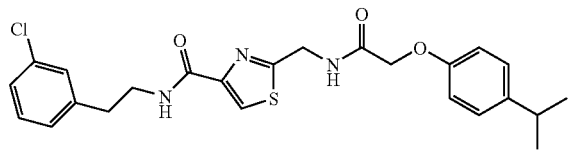

2-{[2-(4-Isopropyl-phenoxy)-acetylamino]-methyl}-thiazole-4-carboxylic acid [2-(3-chloro-phenyl)-ethyl]-amide: 2-Aminomethyl-thiazole-4-carboxylic acid [2-(3-chloro-phenyl)-ethyl]-amide (50 mg, 0.17 mmol) was dissolved in DMF (1 mL). EDC (38 mg, 0.2 mmol) and HOBt (27 mg, 0.2 mmol) where added and the mixture was stirred at ambient temperature for 10 minutes. (4-Isopropyl-phenoxy)-acetic acid (33 mg, 0.17 mmol) was added. The reaction mixture was stirred at ambient temperature for 18 hours. DI water was added and the mixture was extracted with ethyl acetate ×3. The combined organic layers were washed with 1 N hydrochloric acid ×2, 2 N sodium hydroxide ×2, 1 N sodium bicarbonate ×2, DI water ×2 and brine ×1, dried over sodium sulfate, filtered and concentrated in vacuo to give a yellow oil. The oil was purified by column chromatography using silica (1:1 Ethyl acetate:Hexanes) to give the title compound as a semi-solid (16.8 mg, 21%). $^1$H NMR (400 MHz, d$_6$-DMSO): 9.02 (t, 1H), 8.41 (t, 1H), 8.11 (s, 1H), 7.27 (m, 3H), 7.16 (m, 3H), 6.88 (d, 2H), 4.61 (d, 2H), 4.56 (s, 2H), 3.48 (q, 2H), 2.83 (m, 3H), 1.17 (d, 6H); MS (ESI-LCMS) for C$_{24}$H$_{27}$ClN$_3$O$_3$S: 472 (MH$^+$).

Example 56

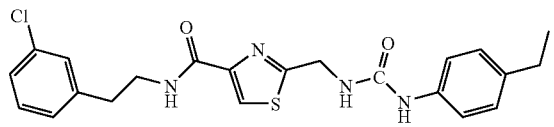

2-[3-(4-Ethyl-phenyl)-ureidomethyl]-thiazole-4-carboxylic acid [2-(3-chloro-phenyl)-ethyl]-amide: 2-Aminomethyl-thiazole-4-carboxylic acid [2-(3-chloro-phenyl)-ethyl]-amide (50 mg, 0.17 mmol) was dissolved in DMF (1 mL). 4-Ethyl phenylisocyanate (0.05 mL, 0.34 mmol) was added and the reaction mixture stirred at ambient temperature for 20 hours. The crude product was concentrated in vacuo. The product was purified by column chromatography (silica, 5% MeOH in DCM) to give a white solid (33.4 mg, 44%). $^1$H NMR (400 MHz, CD$_3$OD): 8.07 (s, 1H), 7.26 (m, 4H), 7.19 (m, 2H), 7.11 (m, 2H), 4.66 (s, 2H), 3.60 (t, 2H), 2.90 (t, 2H), 2.58 (q, 2H), 1.20 (t, 3H); MS (ESI-LCMS) for C$_{22}$H$_{24}$ClN$_4$O$_2$S: 443 (MH$^+$).

Using an analogous synthetic procedure (vide supra), the following compounds were prepared:

2-[3-(4-Isopropyl-phenyl)-ureidomethyl]-thiazole-4-carboxylic acid [2-(3-chloro-phenyl)-ethyl]-amide: Procedure used analogous to that for Example 56; obtained product as white solid (27.5 mg, 38%). $^1$H NMR (400 MHz, d$_6$-DMSO): 8.75 (s, 1H), 8.42 (t, 1H), 8.08 (s, 1H), 7.27 (m, 5H), 7.18 (m, 1H), 7.09 (d, 2H), 6.94 (t, 1H), 4.56 (d, 2H), 3.48 (q, 2H), 2.82 (m, 3H), 1.16 (d, 6H); MS (ESI-LCMS) for C$_{23}$H$_{26}$ClN$_4$O$_2$S: 457 (MH$^+$).

2-{[2-(4-Isopropyl-phenyl)-acetylamino]-methyl}-thiazole-4-carboxylic acid [2-(3-chloro-phenyl)-ethyl]-amide: white solid (35.6 mg, 46%) $^1$H NMR (400 MHz, d$_6$-DMSO): 8.98 (t, 1H), 8.44 (t, 1H), 8.12 (s, 1H), 7.29 (m, 3H), 7.19 (m, 5H), 4.55 (d, 2H), 3.49 (m, 4H), 2.85 (m, 3H), 1.18 (d, 6H); MS (ESI-LCMS) for C$_{24}$H$_{27}$ClN$_3$O$_2$S: 456 (MH$^+$).

N-{4-[2-(3-Chloro-phenyl)-ethylcarbamoyl]-thiazol-2-ylmethyl}-2-(4-fluoro-phenoxy)-nicotinamide: white solid (41.1 mg, 47%) $^1$H NMR (400 MHz, d$_6$-DMSO): 9.37 (t, 1H), 8.45 (t, 1H) 8.21 (m, 2H), 8.14 (s, 1H), 7.29 (m, 8H), 7.19 (m, 1H), 4.82 (d, 2H), 3.49 (q, 2H), 2.85 (t, 2H); MS (ESI-LCMS) for C$_{25}$H$_{21}$ClN$_4$O$_3$S: 511 (MH$^+$).

2-[3-(4-Ethyl-phenyl)-ureidomethyl]-thiazole-4-carboxylic acid [2-(2-fluoro-phenyl)-ethyl]-amide: white solid (31.9 mg, 42%). $^1$H NMR (400 MHz, CD$_3$OD): 8.06 (s, 1H), 7.24 (m, 4H), 7.07 (m, 4H), 4.66 (s, 2H), 3.62 (t, 2H), 2.97 (t, 2H), 2.59 (q, 2H), 1.21 (t, 3H); MS (ESI-LCMS) for C$_{22}$H$_{24}$FN$_4$O$_2$S: 427 (MH$^+$).

2-[3-(4-Ethoxy-phenyl)-ureidomethyl]-thiazole-4-carboxylic acid [2-(3-chloro-phenyl)-ethyl]-amide: white solid (34.2 mg, 44%) $^1$H NMR (400 MHz, d$_6$-DMSO): 8.64 (s, 1H), 8.42 (t, 1H), 8.08 (s, 1H), 7.27 (m, 5H), 7.17 (m, 1H), 6.90 (t, 1H), 6.79 (m, 2H), 4.55 (d, 2H), 3.94 (q, 2H), 3.48 (q, 2H), 2.84 (t, 2H), 1.29 (t, 3H); MS (ESI-LCMS) for C$_{22}$H$_{24}$ClN$_4$O$_3$S: 459 (MH$^+$).

Example 57

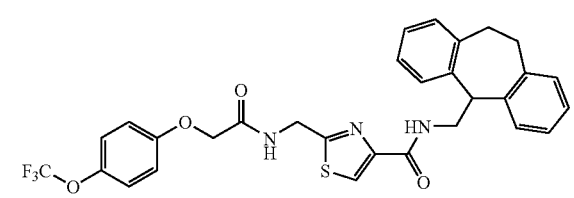

2-{[2-(4-Trifluoromethoxy-phenoxy)-acetylamino]-methyl}-thiazole-4-carboxylic acid (10,11-dihydro-5H-dibenzo [a,d]cyclohepten-5-ylmethyl)-amide: The corresponding carboxylic acid (50 mg, 0.13 mmol) was dissolved in DMF (2 mL). Triethylamine (0.04 mL, 0.26 mmol) was added. The mixture was cooled to 0° C. and isobutylchloroformate (0.02 mL, 0.13 mmol) was added. The mixture was stirred at 0° C. for 90 minutes. The mixture was allowed to return to ambient temperature and the amine (29 mg, 0.13 mmol) was added. The reaction mixture was stirred at ambient temperature for 18 hours. Ammonium chloride was removed by filtration. The reaction mixture was diluted with water and extracted with ethyl acetate ×3. The combined organic layers were washed with 1 N sodium bicarbonate ×2, 1 N hydrochloric acid ×2 and brine ×2, dried over sodium sulfate, filtered and concentrated in vacuo to give a white solid. The product was further purified by column chromatography (silica, 3:1 Ethyl acetate: Hexanes) to give a yellow solid (19.4 mg, 20%). $^1$H NMR (400 MHz, CD$_3$OD): 8.01 (s, 1H), 7.22 (t, 4H), 7.10 (m, 8H), 4.71 (s, 2H), 4.63 (s, 2H), 4.39 (t, 1H), 3.96 (d, 2H), 3.44 (m, 2H), 2.99 (m, 2H); MS (ESI-LCMS) for C$_{30}$H$_{27}$F$_3$N$_3$O$_4$S: 582 (MH$^+$).

Additional examples of compounds that were made according to the methods and procedures described above are set forth in Table 1. Each of these compounds are further aspects of this invention.

Assays

Kinase assays were performed by measurement of incorporation of γ-$^{33}$P ATP into immobilized myelin basic protein (MBP). High binding white 384 well plates (Greiner) were coated with MBP (Sigma #M-1891) by incubation of 60 ul/well of 20 μg/ml MBP in Tris-buffered saline (TBS; 50 mM Tris pH 8.0, 138 mM NaCl, 2.7 mM KCl) for 24 hours at 4° C. Plates were washed 3× with 100 μl TBS. Kinase reactions were carried out in a total volume of 34 μl in kinase buffer (5 mM Hepes pH 7.6, 15 mM NaCl, 0.01% bovine gamma globulin (Sigma #1-5506), 10 mM MgCl$_2$, 1 mM DTT, 0.02% TritonX-100). Compound dilutions were performed in DMSO and added to assay wells to a final DMSO concentration of 1%. Each data point was measured in duplicate, and at least two duplicate assays were performed for each individual compound determination. Enzyme was added to final concentrations of 10 nM or 20 nM, for example. A mixture of unlabeled ATP and γ-$^{33}$P ATP was added to start the reaction (2×10$^6$ cpm of γ-$^{33}$P ATP per well (3000 Ci/mmole) and either 10 μM or 30 μM unlabeled ATP, typically. The reactions were carried out for 1 hour at room temperature with shaking. Plates were washed 7× with TBS, followed by the addition of 50 μl/well scintillation fluid (Wallac). Plates were read using a Wallac Trilux counter. This is only one format of such assays, various other formats are possible, as known to one of ordinary skill in the art.

The above assay procedure can be used to determine the IC$_{50}$ for inhibition and/or the inhibition constant, K$_i$. The IC$_{50}$ is defined as the concentration of compound required to reduce the enzyme activity by 50% under the conditions of the assay. Exemplary compositions have IC$_{50}$'s of, for example, less than about 1100 M, less than about 10 μM, less than about 1 μM, and further for example having IC$_{50}$'s of less than about 100 nM, and still further, for example, less than about 10 nM. The K$_i$ for a compound may be determined from the IC$_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to equation (1) below; where V is the observed rate, V$_{max}$ is the rate of the free enzyme, I$_0$ is the inhibitor concentration, E$_0$ is the enzyme concentration, and K$_d$ is the dissociation constant of the enzyme-inhibitor complex.

$$V = V_{max}E_0\left[1 - \frac{(E_0 + I_0 + K_d) - \sqrt{(E_0 + I_0 + K_d)^2 - 4E_0 I_0}}{2E_0}\right] \quad \text{Equation (1)}$$

Kinase Specific Assays:

Kinase activity and compound inhibition are investigated using one or more of the three assay formats described below. The ATP concentrations for each assay are selected to be close to the Michaelis-Menten constant (K$_M$) for each individual kinase. Dose-response experiments are performed at 10 different inhibitor concentrations in a 384-well plate format. The data are fitted to four-parameter equation (2) below; where Y is the observed signal, X is the inhibitor concentration, Min is the background signal in the absence of enzyme (0% enzyme activity), Max is the signal in the absence of inhibitor (100% enzyme activity), IC$_{50}$ is the inhibitor concentration at 50% enzyme inhibition and H represents the empirical Hill's slope to measure the cooperativity. Typically H is close to unity.

$$Y = Min + (Max - Min)/(1 + (X/IC_{50})^H) \quad \text{Equation (2)}$$

Luciferase-Coupled Chemiluminescent Kinase Assay

ALK biochemical activity was assessed using a Luciferase-Coupled Chemiluminescent Kinase assay (LCCA) format in which kinase activity was measured as the percent ATP remaining following the kinase reaction. ATP remaining after the kinase reaction was detected by luciferase-luciferin-coupled chemiluminescence. The reaction was initiated by mixing test compounds, 1 μM ATP, 4 μM poly-AEKY and 12 nM ALK (baculovirus expressed human ALK kinase domain F1098-K1410) in a 20 μL assay buffer (20 mM Tris-HCL pH7.5, 10 mM MgCl$_2$, 0.02% Triton X-100, 100 mM DTT, 2 mM MnCl$_2$). The mixture was incubated at ambient temperature for 2 hours after which 20 μL luciferase-luciferin mix was added and the chemiluminescent signal read using a Wallac Victor$^2$ reader. The luciferase-luciferin mix consists of 50 mM HEPES, pH 7.8, 8.5 μg/mL oxalic acid (pH 7.8), 5 (or 50) mM DTT, 0.4% Triton X-100, 0.25 mg/mL coenzyme A, 63 μM AMP, 28 μg/mL luciferin and 40,000 units of light/mL luciferase. Consumption of ATP by ALK can be quantified and utilized as a measure of inhibition of ALK activity by compounds described herein. By employing serial dilutions of compounds to be tested, the ability of test compounds to inhibit ALK activity can be determined. IC$_{50}$ values can also be obtained from these data, as shown in Table 2.

Example 59

The following are examples of representative pharmaceutical dosage forms for the compounds of the invention:

| Injectable Suspension (I.M.) | mg/mL |
|---|---|
| Compound of the invention | 10 |
| Methylcellulose | 5.0 |
| Tween 80 | 0.5 |
| Benzyl alcohol | 9.0 |
| Benzalkonium chloride | 1.0 |

| Tablet | mg/tablet |
|---|---|
| Compound of the invention | 25 |
| Microcrystalline Cellulose | 415 |
| Povidone | 14.0 |
| Pregelatinized Starch | 43.5 |
| Magnesium Stearate | 2.5 |
| Total = | 500 mg |

| Capsule | mg/capsule |
|---|---|
| Compound of the invention | 25 |
| Lactose Powder | 573.5 |
| Magnesium Stearate | 1.5 |
| Total = | 600 mg |

| Aerosol | Per canister |
|---|---|
| Compound of the invention | 24 mg |
| Lecithin, NF Liq. Conc. | 1.2 mg |
| Trichlorofluoromethane, NF | 4.025 g |
| Dichlorodifluoromethane, NF | 12.15 g |

Structure Activity Relationships

Table 2 shows structure activity relationship data for selected compounds of the invention. Inhibition is indicated as IC$_{50}$ with the following key: A=IC$_{50}$ less than 50 nM, B=IC$_{50}$ greater than 50 nM, but less than 500 nM, C=IC$_{50}$ greater than 500 nM, but less than 2000 nM, and D=IC$_{50}$ equal to, or greater than 2,000 nM.

TABLE 2

| Entry | Name | ALK IC$_{50}$ |
|---|---|---|
| 1 | N-[2-(3-chlorophenyl)ethyl]-2-(1-{[({4-[(trifluoromethyl)oxy]phenyl}oxy)acetyl]amino}ethyl)-1,3-thiazole-4-carboxamide | A |
| 2 | N-[2-(3-chlorophenyl)ethyl]-2-({[({4-[(trifluoromethyl)oxy]phenyl}oxy)acetyl]amino}methyl)-1,3-thiazole-4-carboxamide | A |
| 3 | N-{[4-(1,3-dihydro-2H-isoindol-2-ylcarbonyl)-1,3-thiazol-2-yl]methyl}-2-({4-[(trifluoromethyl)oxy]phenyl}oxy)acetamide | A |
| 4 | N-(10,11-dihydro-5H-dibenzo[a,d]cyclohepten-5-ylmethyl)-2-({[({4-[(trifluoromethyl)oxy]phenyl}oxy)acetyl]amino}methyl)-1,3-thiazole-4-carboxamide | A |
| 5 | N-[2-(2-fluorophenyl)ethyl]-2-({[({4-[(trifluoromethyl)oxy]phenyl}oxy)acetyl]amino}methyl)-1,3-thiazole-4-carboxamide | A |
| 6 | N-[(2R)-2-phenylpropyl]-2-({[({4-[(trifluoromethyl)oxy]phenyl}oxy)acetyl]amino}methyl)-1,3-thiazole-4-carboxamide | A |
| 7 | N-(2-phenylpropyl)-2-({[({4-[(trifluoromethyl)oxy]phenyl}oxy)acetyl]amino}methyl)-1,3-thiazole-4-carboxamide | A |
| 8 | N-[2-(3-chlorophenyl)ethyl]-2-[({[(4-ethylphenyl)amino]carbonyl}amino)methyl]-1,3-thiazole-4-carboxamide | A |
| 9 | N-{2-[4-(methyloxy)phenyl]ethyl}-2-({[({4-[(trifluoromethyl)oxy]phenyl}oxy)acetyl]amino}methyl)-1,3-thiazole-4-carboxamide | A |
| 10 | N-[2-(4-ethylphenyl)ethyl]-2-({[({4-[(trifluoromethyl)oxy]phenyl}oxy)acetyl]amino}methyl)-1,3-thiazole-4-carboxamide | A |
| 11 | N-{[2,3-bis(methyloxy)phenyl]methyl}-2-({[({4-[(trifluoromethyl)oxy]phenyl}oxy)acetyl]amino}methyl)-1,3-thiazole-4-carboxamide | A |
| 12 | 2-({[({4-[(trifluoromethyl)oxy]phenyl}oxy)acetyl]amino}methyl)-N-[(1S,2S,3S,5R)-2,6,6-trimethylbicyclo[3.1.1]hept-3-yl]-1,3-thiazole-4-carboxamide | A |
| 13 | N-{2-[4-(aminosulfonyl)phenyl]ethyl}-2-({[({4-[(trifluoromethyl)oxy]phenyl}oxy)acetyl]amino}methyl)-1,3-thiazole-4-carboxamide | A |
| 14 | N-[2-(3-fluorophenyl)ethyl]-2-({[({4-[(trifluoromethyl)oxy]phenyl}oxy)acetyl]amino}methyl)-1,3-thiazole-4-carboxamide | A |
| 15 | N-[2-(2-methylphenyl)ethyl]-2-({[({4-[(trifluoromethyl)oxy]phenyl}oxy)acetyl]amino}methyl)-1,3-thiazole-4-carboxamide | A |
| 16 | N-[2-(3-chlorophenyl)ethyl]-2-[({[(4-iodophenyl)oxy]acetyl}amino)methyl]-1,3-thiazole-4-carboxamide | A |
| 17 | N-{[2-(methyloxy)phenyl]methyl}-2-({[({4-[(trifluoromethyl)oxy]phenyl}oxy)acetyl]amino}methyl)-1,3-thiazole-4-carboxamide | A |
| 18 | N-(2,2-diphenylethyl)-2-({[({4-[(trifluoromethyl)oxy]phenyl}oxy)acetyl]amino}methyl)-1,3-thiazole-4-carboxamide | A |
| 19 | N-[2-(2-thienyl)ethyl]-2-({[({4-[(trifluoromethyl)oxy]phenyl}oxy)acetyl]amino}methyl)-1,3-thiazole-4-carboxamide | A |
| 20 | N-{2-[3-(ethyloxy)-4-(methyloxy)phenyl]ethyl}-2-({[({4-[(trifluoromethyl)oxy]phenyl}oxy)acetyl]amino}methyl)-1,3-thiazole-4-carboxamide | A |
| 21 | N-[2-(3-methylphenyl)ethyl]-2-({[({4-[(trifluoromethyl)oxy]phenyl}oxy)acetyl]amino}methyl)-1,3-thiazole-4-carboxamide | A |
| 22 | 2-{[({[4-(1,1-dimethylethyl)phenyl]oxy}acetyl)amino]methyl}-N-{[2-(methyloxy)phenyl]methyl}-1,3-thiazole-4-carboxamide | A |
| 23 | N-tricyclo[3.3.1.1~3,7~]dec-1-yl-2-({[({4-[(trifluoromethyl)oxy]phenyl}oxy)acetyl]amino}methyl)-1,3-thiazole-4-carboxamide | A |
| 24 | N-[2-(4-fluorophenyl)ethyl]-2-({[({4-[(trifluoromethyl)oxy]phenyl}oxy)acetyl]amino}methyl)-1,3-thiazole-4-carboxamide | A |
| 25 | N-[2-(3-chlorophenyl)ethyl]-2-{[({[(4-(1-methylethyl)phenyl]amino}carbonyl)amino]methyl}-1,3-thiazole-4-carboxamide | A |
| 26 | N-[(2S)-2-phenylpropyl]-2-({[({4-[(trifluoromethyl)oxy]phenyl}oxy)acetyl]amino}methyl)-1,3-thiazole-4-carboxamide | A |

TABLE 2-continued

| Entry | Name | ALK IC$_{50}$ |
|---|---|---|
| 27 | N-[2-(2-fluorophenyl)ethyl]-2-{[({[4-(1-methylethyl)phenyl]amino}carbonyl)amino]methyl}-1,3-thiazole-4-carboxamide | A |
| 28 | N-{2-[3-(ethyloxy)phenyl]ethyl}-2-({[({4-[(trifluoromethyl)oxy]phenyl}oxy)acetyl]amino}methyl)-1,3-thiazole-4-carboxamide | B |
| 29 | 2-{[({[4-(1-methylethyl)phenyl]amino}carbonyl)amino]methyl}-N-{[2-(methyloxy)phenyl]methyl}-1,3-thiazole-4-carboxamide | B |
| 30 | N-{2-[3,5-bis(methyloxy)phenyl]ethyl}-2-({[({4-[(trifluoromethyl)oxy]phenyl}oxy)acetyl]amino}methyl)-1,3-thiazole-4-carboxamide | B |
| 31 | N-[2-(3-chlorophenyl)ethyl]-2-({[({4-[(trifluoromethyl)oxy]phenyl}oxy)acetyl]amino}methyl)-1,3-oxazole-4-carboxamide | B |
| 32 | N-[(2-chlorophenyl)methyl]-2-({[({4-[(trifluoromethyl)oxy]phenyl}oxy)acetyl]amino}methyl)-1,3-thiazole-4-carboxamide | B |
| 33 | N-[2-(2,5-dimethylphenyl)ethyl]-2-({[({4-[(trifluoromethyl)oxy]phenyl}oxy)acetyl]amino}methyl)-1,3-thiazole-4-carboxamide | B |
| 34 | N-({2-[(difluoromethyl)oxy]phenyl}methyl)-2-({[({4-[(trifluoromethyl)oxy]phenyl}oxy)acetyl]amino}methyl)-1,3-thiazole-4-carboxamide | B |
| 35 | N-(2-cyclohex-1-en-1-ylethyl)-2-({[({4-[(trifluoromethyl)oxy]phenyl}oxy)acetyl]amino}methyl)-1,3-thiazole-4-carboxamide | B |
| 36 | N-[2-(4-methylphenyl)ethyl]-2-({[({4-[(trifluoromethyl)oxy]phenyl}oxy)acetyl]amino}methyl)-1,3-thiazole-4-carboxamide | B |
| 37 | N-[3-(butyloxy)propyl]-2-({[({4-[(trifluoromethyl)oxy]phenyl}oxy)acetyl]amino}methyl)-1,3-thiazole-4-carboxamide | B |
| 38 | N-(10,11-dihydro-5H-dibenzo[a,d]cyclohepten-5-ylmethyl)-2-({[({4-[(trifluoromethyl)oxy]phenyl}oxy)acetyl]amino}methyl)-1,3-oxazole-4-carboxamide | B |
| 39 | N-[(5-chloro-2-methylphenyl)methyl]-2-({[({4-[(trifluoromethyl)oxy]phenyl}oxy)acetyl]amino}methyl)-1,3-thiazole-4-carboxamide | B |
| 40 | N-{2-[3-(methyloxy)phenyl]ethyl}-2-({[({4-[(trifluoromethyl)oxy]phenyl}oxy)acetyl]amino}methyl)-1,3-thiazole-4-carboxamide | B |
| 41 | N-{[2-(methylthio)phenyl]methyl}-2-({[({4-[(trifluoromethyl)oxy]phenyl}oxy)acetyl]amino}methyl)-1,3-thiazole-4-carboxamide | B |
| 42 | N-{2-[3,4-bis(methyloxy)phenyl]ethyl}-2-({[({4-[(trifluoromethyl)oxy]phenyl}oxy)acetyl]amino}methyl)-1,3-thiazole-4-carboxamide | B |
| 43 | N-{2-[4-(ethyloxy)-3-(methyloxy)phenyl]ethyl}-2-({[({4-[(trifluoromethyl)oxy]phenyl}oxy)acetyl]amino}methyl)-1,3-thiazole-4-carboxamide | B |
| 44 | N-[2-(3,4-dichlorophenyl)ethyl]-2-({[({4-[(trifluoromethyl)oxy]phenyl}oxy)acetyl]amino}methyl)-1,3-thiazole-4-carboxamide | B |
| 45 | N-[2-(1H-indol-3-yl)ethyl]-2-({[({4-[(trifluoromethyl)oxy]phenyl}oxy)acetyl]amino}methyl)-1,3-thiazole-4-carboxamide | B |
| 46 | N-[(2,3-dimethylphenyl)methyl]-2-({[({4-[(trifluoromethyl)oxy]phenyl}oxy)acetyl]amino}methyl)-1,3-thiazole-4-carboxamide | B |
| 47 | N-[(5-fluoro-2-methylphenyl)methyl]-2-({[({4-[(trifluoromethyl)oxy]phenyl}oxy)acetyl]amino}methyl)-1,3-thiazole-4-carboxamide | B |
| 48 | N-(2-pyridin-4-ylethyl)-2-({[({4-[(trifluoromethyl)oxy]phenyl}oxy)acetyl]amino}methyl)-1,3-thiazole-4-carboxamide | B |
| 49 | N-[2-(2,4-dimethylphenyl)ethyl]-2-({[({4-[(trifluoromethyl)oxy]phenyl}oxy)acetyl]amino}methyl)-1,3-thiazole-4-carboxamide | B |
| 50 | N-[2-(3-chlorophenyl)ethyl]-2-[({[4-(1-methylethyl)phenyl]acetyl}amino)methyl]-1,3-thiazole-4-carboxamide | B |
| 51 | N-(2-pyridin-3-ylethyl)-2-({[({4-[(trifluoromethyl)oxy]phenyl}oxy)acetyl]amino}methyl)-1,3-thiazole-4-carboxamide | B |
| 52 | 2-({[({4-[(trifluoromethyl)oxy]phenyl}oxy)acetyl]amino}methyl)-N-{2-[3-(trifluoromethyl)phenyl]ethyl}-1,3-thiazole-4-carboxamide | B |

TABLE 2-continued

| Entry | Name | ALK IC$_{50}$ |
|---|---|---|
| 53 | N-{2-[2,3-bis(methyloxy)phenyl]ethyl}-2-({[({4-[(trifluoromethyl)oxy]phenyl}oxy)acetyl]amino}methyl)-1,3-thiazole-4-carboxamide | B |
| 54 | N-(2-amino-2-oxo-1-phenylethyl)-2-({[({4-[(trifluoromethyl)oxy]phenyl}oxy)acetyl]amino}methyl)-1,3-thiazole-4-carboxamide | B |
| 55 | N-[2-(2-fluorophenyl)ethyl]-2-{[({[4-(1-methylethyl)phenyl]oxy}acetyl)amino]methyl}-1,3-thiazole-4-carboxamide | B |
| 56 | N-[2-(3,4-dimethylphenyl)ethyl]-2-({[({4-[(trifluoromethyl)oxy]phenyl}oxy)acetyl]amino}methyl)-1,3-thiazole-4-carboxamide | B |
| 57 | N-({2-[(trifluoromethyl)oxy]phenyl}methyl)-2-({[({4-[(trifluoromethyl)oxy]phenyl}oxy)acetyl]amino}methyl)-1,3-thiazole-4-carboxamide | B |
| 58 | N-{[2-(ethyloxy)phenyl]methyl}-2-({[({4-[(trifluoromethyl)oxy]phenyl}oxy)acetyl]amino}methyl)-1,3-thiazole-4-carboxamide | B |
| 59 | N-[2-(2-fluorophenyl)ethyl]-2-[({[(4-iodophenyl)oxy]acetyl}amino)methyl]-1,3-thiazole-4-carboxamide | B |
| 60 | N-{2-[2-(ethyloxy)phenyl]ethyl}-2-({[({4-[(trifluoromethyl)oxy]phenyl}oxy)acetyl]amino}methyl)-1,3-thiazole-4-carboxamide | B |
| 61 | N-[(2,5-difluorophenyl)methyl]-2-({[({4-[(trifluoromethyl)oxy]phenyl}oxy)acetyl]amino}methyl)-1,3-thiazole-4-carboxamide | B |
| 62 | N-{[4-({[2-(3-chlorophenyl)ethyl]amino}carbonyl)-1,3-thiazol-2-yl]methyl}-2-[(4-chlorophenyl)oxy]pyridine-3-carboxamide | B |
| 63 | 2-({[({4-[(trifluoromethyl)oxy]phenyl}oxy)acetyl]amino}methyl)-N-{[2-(trifluoromethyl)phenyl]methyl}-1,3-thiazole-4-carboxamide | B |
| 64 | N-[(2,4-dichlorophenyl)methyl]-2-({[({4-[(trifluoromethyl)oxy]phenyl}oxy)acetyl]amino}methyl)-1,3-thiazole-4-carboxamide | B |
| 65 | N-(1-phenylpropyl)-2-({[({4-[(trifluoromethyl)oxy]phenyl}oxy)acetyl]amino}methyl)-1,3-thiazole-4-carboxamide | B |
| 66 | N-[(4-{[4-(3,5-dichloropyridin-4-yl)piperazin-1-yl]carbonyl}-1,3-thiazol-2-yl)methyl]-2-({4-[(trifluoromethyl)oxy]phenyl}oxy)acetamide | B |
| 67 | N-[2-(3-chlorophenyl)ethyl]-2-{[({[4-(1,1-dimethylethyl)phenyl]oxy}acetyl)amino]methyl}-1,3-thiazole-4-carboxamide | B |
| 68 | N-{2-[4-(ethyloxy)phenyl]ethyl}-2-({[({4-[(trifluoromethyl)oxy]phenyl}oxy)acetyl]amino}methyl)-1,3-thiazole-4-carboxamide | B |
| 69 | N-[(3,5-dichlorophenyl)methyl]-2-({[({4-[(trifluoromethyl)oxy]phenyl}oxy)acetyl]amino}methyl)-1,3-thiazole-4-carboxamide | B |
| 70 | Nalpha-{[2-({[({4-[(trifluoromethyl)oxy]phenyl}oxy)acetyl]amino}methyl)-1,3-thiazol-4-yl]carbonyl}-D-phenylalaninamide | B |
| 71 | N-{2-[(furan-2-ylmethyl)thio]ethyl}-2-({[({4-[(trifluoromethyl)oxy]phenyl}oxy)acetyl]amino}methyl)-1,3-thiazole-4-carboxamide | B |
| 72 | N-[2-(3-chlorophenyl)ethyl]-2-{[({[4-(1-methylethyl)phenyl]oxy}acetyl)amino]methyl}-1,3-thiazole-4-carboxamide | B |
| 73 | N-{[4-chloro-3-(trifluoromethyl)phenyl]methyl}-2-({[({4-[(trifluoromethyl)oxy]phenyl}oxy)acetyl]amino}methyl)-1,3-thiazole-4-carboxamide | B |
| 74 | N-[3-(propyloxy)propyl]-2-({[({4-[(trifluoromethyl)oxy]phenyl}oxy)acetyl]amino}methyl)-1,3-thiazole-4-carboxamide | B |
| 75 | N-[(3,4-dichlorophenyl)methyl]-2-({[({4-[(trifluoromethyl)oxy]phenyl}oxy)acetyl]amino}methyl)-1,3-thiazole-4-carboxamide | B |
| 76 | N-cyclooctyl-2-({[({4-[(trifluoromethyl)oxy]phenyl}oxy)acetyl]amino}methyl)-1,3-thiazole-4-carboxamide | B |
| 77 | N-(2-pyridin-2-ylethyl)-2-({[({4-[(trifluoromethyl)oxy]phenyl}oxy)acetyl]amino}methyl)-1,3-thiazole-4-carboxamide | B |
| 78 | N-{[2,3-bis(methyloxy)phenyl]methyl}-2-{[({[4-(1-methylethyl)phenyl]amino}carbonyl)amino]methyl}-1,3-thiazole-4-carboxamide | B |
| 79 | N-[(1S)-1,2,3,4-tetrahydronaphthalen-1-yl]-2-({[({4-[(trifluoromethyl)oxy]phenyl}oxy)acetyl]amino}methyl)-1,3-thiazole-4-carboxamide | B |

TABLE 2-continued

| Entry | Name | ALK IC$_{50}$ |
|---|---|---|
| 80 | N-{2-[2-(methyloxy)phenyl]ethyl}-2-({[({4-[(trifluoromethyl)oxy]phenyl}oxy)acetyl]amino}methyl)-1,3-thiazole-4-carboxamide | B |
| 81 | N-(2-{[4-(methyloxy)phenyl]oxy}ethyl)-2-({[({4-[(trifluoromethyl)oxy]phenyl}oxy)acetyl]amino}methyl)-1,3-thiazole-4-carboxamide | B |
| 82 | 2-[({[(4-iodophenyl)oxy]acetyl}amino)methyl]-N-{[2-(methyloxy)phenyl]methyl}-1,3-thiazole-4-carboxamide | B |
| 83 | N-[2-(4-chlorophenyl)ethyl]-2-({[({4-[(trifluoromethyl)oxy]phenyl}oxy)acetyl]amino}methyl)-1,3-thiazole-4-carboxamide | B |
| 84 | N-[1-(phenylmethyl)piperidin-4-yl]-2-({[({4-[(trifluoromethyl)oxy]phenyl}oxy)acetyl]amino}methyl)-1,3-thiazole-4-carboxamide | B |
| 85 | N-(1-naphthalen-1-ylethyl)-2-({[({4-[(trifluoromethyl)oxy]phenyl}oxy)acetyl]amino}methyl)-1,3-thiazole-4-carboxamide | B |
| 86 | N-[1-(4-fluorophenyl)ethyl]-2-({[({4-[(trifluoromethyl)oxy]phenyl}oxy)acetyl]amino}methyl)-1,3-thiazole-4-carboxamide | B |
| 87 | N-(2-methylcyclohexyl)-2-({[({4-[(trifluoromethyl)oxy]phenyl}oxy)acetyl]amino}methyl)-1,3-thiazole-4-carboxamide | B |
| 88 | 2-({[({4-[(trifluoromethyl)oxy]phenyl}oxy)acetyl]amino}methyl)-N-[(1R,2R,3R,5S)-2,6,6-trimethylbicyclo[3.1.1]hept-3-yl]-1,3-thiazole-4-carboxamide | B |
| 89 | 2-({[({4-[(trifluoromethyl)oxy]phenyl}oxy)acetyl]amino}methyl)-N-[(1S,2S,3S,5R)-2,6,6-trimethylbicyclo[3.1.1]hept-3-yl]-1,3-oxazole-4-carboxamide | B |
| 90 | N-[2-(4-bromophenyl)ethyl]-2-({[({4-[(trifluoromethyl)oxy]phenyl}oxy)acetyl]amino}methyl)-1,3-thiazole-4-carboxamide | B |
| 91 | N-[(1S)-2-oxo-1-(phenylmethyl)-2-pyrrolidin-1-ylethyl]-2-({[({4-[(trifluoromethyl)oxy]phenyl}oxy)acetyl]amino}methyl)-1,3-thiazole-4-carboxamide | B |
| 92 | N-{2-[4-(aminosulfonyl)phenyl]ethyl}-2-({[({4-[(trifluoromethyl)oxy]phenyl}oxy)acetyl]amino}methyl)-1,3-oxazole-4-carboxamide | B |
| 93 | N-(2-{[(2,6-dichlorophenyl)methyl]thio}ethyl)-2-({[({4-[(trifluoromethyl)oxy]phenyl}oxy)acetyl]amino}methyl)-1,3-thiazole-4-carboxamide | B |
| 94 | N-(2-methylpropyl)-2-({[({4-[(trifluoromethyl)oxy]phenyl}oxy)acetyl]amino}methyl)-1,3-thiazole-4-carboxamide | B |
| 95 | N-[(1S)-1-cyclohexylethyl]-2-({[({4-[(trifluoromethyl)oxy]phenyl}oxy)acetyl]amino}methyl)-1,3-thiazole-4-carboxamide | B |
| 96 | N-{[4-(1,3,4,9-tetrahydro-2H-beta-carbolin-2-ylcarbonyl)-1,3-thiazol-2-yl]methyl}-2-({4-[(trifluoromethyl)oxy]phenyl}oxy)acetamide | B |
| 97 | N-{[2-chloro-5-(trifluoromethyl)phenyl]methyl}-2-({[({4-[(trifluoromethyl)oxy]phenyl}oxy)acetyl]amino}methyl)-1,3-thiazole-4-carboxamide | B |
| 98 | N-[(2-methylphenyl)methyl]-2-({[({4-[(trifluoromethyl)oxy]phenyl}oxy)acetyl]amino}methyl)-1,3-thiazole-4-carboxamide | B |
| 99 | N-(1-naphthalen-1-ylethyl)-2-({[({4-[(trifluoromethyl)oxy]phenyl}oxy)acetyl]amino}methyl)-1,3-oxazole-4-carboxamide | B |
| 100 | N-{3-[(2-ethylhexyl)oxy]propyl}-2-({[({4-[(trifluoromethyl)oxy]phenyl}oxy)acetyl]amino}methyl)-1,3-thiazole-4-carboxamide | B |
| 101 | 2-[({[(4-ethylphenyl)amino]carbonyl}amino)methyl]-N-[2-(2-fluorophenyl)ethyl]-1,3-thiazole-4-carboxamide | B |
| 102 | 2-({[({4-[(trifluoromethyl)oxy]phenyl}oxy)acetyl]amino}methyl)-N-[(1S)-1,2,2-trimethylpropyl]-1,3-thiazole-4-carboxamide | B |
| 103 | N-{(1S,2S)-2-[(phenylmethyl)oxy]cyclopentyl}-2-({[({4-[(trifluoromethyl)oxy]phenyl}oxy)acetyl]amino}methyl)-1,3-thiazole-4-carboxamide | B |
| 104 | N-[2-(2-chlorophenyl)ethyl]-2-({[({4-[(trifluoromethyl)oxy]phenyl}oxy)acetyl]amino}methyl)-1,3-thiazole-4-carboxamide | B |
| 105 | N-[(1R,2R,4S)-bicyclo[2.2.1]hept-2-yl]-2-({[({4-[(trifluoromethyl)oxy]phenyl}oxy)acetyl]amino}methyl)-1,3-thiazole-4-carboxamide | B |
| 106 | N-{[2,6-bis(methyloxy)phenyl]methyl}-2-({[({4-[(trifluoromethyl)oxy]phenyl}oxy)acetyl]amino}methyl)-1,3-thiazole-4-carboxamide | B |

TABLE 2-continued

| Entry | Name | ALK IC$_{50}$ |
|---|---|---|
| 107 | N-{3-[methyl(phenyl)amino]propyl}-2-({[({4-[(trifluoromethyl)oxy]phenyl}oxy)acetyl]amino}methyl)-1,3-thiazole-4-carboxamide | B |
| 108 | N-(1-phenylethyl)-2-({[({4-[(trifluoromethyl)oxy]phenyl}oxy)acetyl]amino}methyl)-1,3-thiazole-4-carboxamide | B |
| 109 | 2-[({[(4-bromophenyl)oxy]acetyl}amino)methyl]-N-[2-(3-chlorophenyl)ethyl]-1,3-thiazole-4-carboxamide | B |
| 110 | 2-[({[(4-ethylphenyl)amino]carbonyl}amino)methyl]-N-{2-(methyloxy)phenyl]methyl}-1,3-thiazole-4-carboxamide | B |
| 111 | N-[2-(3-chlorophenyl)ethyl]-2-[({[(4-ethylphenyl)oxy]acetyl}amino)methyl]-1,3-thiazole-4-carboxamide | B |
| 112 | N-{[2,5-bis(methyloxy)phenyl]methyl}-2-({[({4-[(trifluoromethyl)oxy]phenyl}oxy)acetyl]amino}methyl)-1,3-thiazole-4-carboxamide | B |
| 113 | N-hexyl-2-({[({4-[(trifluoromethyl)oxy]phenyl}oxy)acetyl]amino}methyl)-1,3-thiazole-4-carboxamide | B |
| 114 | N-[2-(2-fluorophenyl)ethyl]-2-[({[4-(1-methylethyl)phenyl]acetyl}amino)methyl]-1,3-thiazole-4-carboxamide | B |
| 115 | N-[(2,6-difluorophenyl)methyl]-2-({[({4-[(trifluoromethyl)oxy]phenyl}oxy)acetyl]amino}methyl)-1,3-thiazole-4-carboxamide | B |
| 116 | N-[(2,3-difluorophenyl)methyl]-2-({[({4-[(trifluoromethyl)oxy]phenyl}oxy)acetyl]amino}methyl)-1,3-thiazole-4-carboxamide | B |
| 117 | N-[2-(3-chlorophenyl)ethyl]-2-{[(naphthalen-2-ylacetyl)amino]methyl}-1,3-thiazole-4-carboxamide | B |
| 118 | 2-{[({[4-(1-methylethyl)phenyl]oxy}acetyl)amino]methyl}-N-{2-(methyloxy)phenyl]methyl}-1,3-thiazole-4-carboxamide | B |
| 119 | N-[(3-chlorophenyl)methyl]-2-({[({4-[(trifluoromethyl)oxy]phenyl}oxy)acetyl]amino}methyl)-1,3-thiazole-4-carboxamide | B |
| 120 | N-{[2,4-bis(methyloxy)phenyl]methyl}-2-({[({4-[(trifluoromethyl)oxy]phenyl}oxy)acetyl]amino}methyl)-1,3-thiazole-4-carboxamide | B |
| 121 | N-{[3,5-bis(methyloxy)phenyl]methyl}-2-({[({4-[(trifluoromethyl)oxy]phenyl}oxy)acetyl]amino}methyl)-1,3-thiazole-4-carboxamide | B |
| 122 | N-[2-(phenyloxy)ethyl]-2-({[({4-[(trifluoromethyl)oxy]phenyl}oxy)acetyl]amino}methyl)-1,3-thiazole-4-carboxamide | B |
| 123 | 1,1-dimethylethyl [5-({[2-({[({4-[(trifluoromethyl)oxy]phenyl}oxy)acetyl]amino}methyl)-1,3-thiazol-4-yl]carbonyl}amino)pentyl]carbamate | B |
| 124 | N-{2-[ethyl(3-methylphenyl)amino]ethyl}-2-({[({4-[(trifluoromethyl)oxy]phenyl}oxy)acetyl]amino}methyl)-1,3-thiazole-4-carboxamide | B |
| 125 | N-{[2,3-bis(methyloxy)phenyl]methyl}-2-{[({[4-(1-methylethyl)phenyl]oxy}acetyl)amino]methyl}-1,3-thiazole-4-carboxamide | B |
| 126 | N-[(3,5-difluorophenyl)methyl]-2-({[({4-[(trifluoromethyl)oxy]phenyl}oxy)acetyl]amino}methyl)-1,3-thiazole-4-carboxamide | B |
| 127 | N-[(3-fluorophenyl)methyl]-2-({[({4-[(trifluoromethyl)oxy]phenyl}oxy)acetyl]amino}methyl)-1,3-thiazole-4-carboxamide | B |
| 128 | N-[(2R)-2-phenylpropyl]-2-({[({4-[(trifluoromethyl)oxy]phenyl}oxy)acetyl]amino}methyl)-1,3-oxazole-4-carboxamide | B |
| 129 | 2-[(4-chlorophenyl)oxy]-N-{4-({[2-(2-fluorophenyl)ethyl]amino}carbonyl)-1,3-thiazol-2-yl]methyl}pyridine-3-carboxamide | B |
| 130 | N-{2-[({5-[(dimethylamino)methyl]furan-2-yl}methyl)thio]ethyl}-2-({[({4-[(trifluoromethyl)oxy]phenyl}oxy)acetyl]amino}methyl)-1,3-thiazole-4-carboxamide | B |
| 131 | N-[2-(3-chlorophenyl)ethyl]-2-(2-phenyl-1-{[({4-[(trifluoromethyl)oxy]phenyl}oxy)acetyl]amino}ethyl)-1,3-thiazole-4-carboxamide | B |
| 132 | N-(2-ethylbutyl)-2-({[({4-[(trifluoromethyl)oxy]phenyl}oxy)acetyl]amino}methyl)-1,3-thiazole-4-carboxamide | B |
| 133 | N-[(3-methyl-2-thienyl)methyl]-2-({[({4-[(trifluoromethyl)oxy]phenyl}oxy)acetyl]amino}methyl)-1,3-thiazole-4-carboxamide | B |

TABLE 2-continued

| Entry | Name | ALK IC$_{50}$ |
|---|---|---|
| 134 | N-{[2,3-bis(methyloxy)phenyl]methyl}-2-[({[(4-ethylphenyl)amino]carbonyl}amino)methyl]-1,3-thiazole-4-carboxamide | B |
| 135 | N-[(5-methyl-3-phenylisoxazol-4-yl)methyl]-2-({[({4-[(trifluoromethyl)oxy]phenyl}oxy)acetyl]amino}methyl)-1,3-thiazole-4-carboxamide | B |
| 136 | N-[2-(3-chlorophenyl)ethyl]-2-[({N-[(4-nitrophenyl)carbonyl]glycyl}amino)methyl]-1,3-thiazole-4-carboxamide | B |
| 137 | N-{2-[2,5-bis(methyloxy)phenyl]ethyl}-2-({[({4-[(trifluoromethyl)oxy]phenyl}oxy)acetyl]amino}methyl)-1,3-thiazole-4-carboxamide | B |
| 138 | N-(3-methylbutyl)-2-({[({4-[(trifluoromethyl)oxy]phenyl}oxy)acetyl]amino}methyl)-1,3-thiazole-4-carboxamide | B |
| 139 | N-{[4-(3,4-dihydroisoquinolin-2(1H)-ylcarbonyl)-1,3-thiazol-2-yl]methyl}-2-({4-[(trifluoromethyl)oxy]phenyl}oxy)acetamide | B |
| 140 | N-(4-methylcyclohexyl)-2-({[({4-[(trifluoromethyl)oxy]phenyl}oxy)acetyl]amino}methyl)-1,3-thiazole-4-carboxamide | B |
| 141 | N-{[4-({[2-(3-chlorophenyl)ethyl]amino}carbonyl)-1,3-thiazol-2-yl]methyl}-2-[(4-fluorophenyl)oxy]pyridine-3-carboxamide | B |
| 142 | 2-hydroxy-4-({[2-({[({4-[(trifluoromethyl)oxy]phenyl}oxy)acetyl]amino}methyl)-1,3-thiazol-4-yl]carbonyl}amino)benzoic acid | B |
| 143 | N-[2-(2-fluorophenyl)ethyl]-2-({[({4-[(trifluoromethyl)oxy]phenyl}oxy)acetyl]amino}methyl)-1,3-oxazole-4-carboxamide | B |
| 144 | N-({4-[({[2,3-bis(methyloxy)phenyl]methyl}amino)carbonyl]-1,3-thiazol-2-yl}methyl)-2-[(4-chlorophenyl)oxy]pyridine-3-carboxamide | B |
| 145 | N-(2-phenylethyl)-2-({[({4-[(trifluoromethyl)oxy]phenyl}oxy)acetyl]amino}methyl)-1,3-thiazole-4-carboxamide | B |
| 146 | N-[2-(ethylthio)ethyl]-2-({[({4-[(trifluoromethyl)oxy]phenyl}oxy)acetyl]amino}methyl)-1,3-thiazole-4-carboxamide | B |
| 147 | N-(1,1-diethylprop-2-yn-1-yl)-2-({[({4-[(trifluoromethyl)oxy]phenyl}oxy)acetyl]amino}methyl)-1,3-thiazole-4-carboxamide | B |
| 148 | N-[2-(3-fluorophenyl)ethyl]-2-({[({4-[(trifluoromethyl)oxy]phenyl}oxy)acetyl]amino}methyl)-1,3-oxazole-4-carboxamide | B |
| 149 | N-[3-(methylthio)propyl]-2-({[({4-[(trifluoromethyl)oxy]phenyl}oxy)acetyl]amino}methyl)-1,3-thiazole-4-carboxamide | B |
| 150 | N-[(4-chloro-2-methylphenyl)methyl]-2-({[({4-[(trifluoromethyl)oxy]phenyl}oxy)acetyl]amino}methyl)-1,3-thiazole-4-carboxamide | B |
| 151 | N-[2-(3-methylphenyl)ethyl]-2-({[({4-[(trifluoromethyl)oxy]phenyl}oxy)acetyl]amino}methyl)-1,3-oxazole-4-carboxamide | B |
| 152 | N-(1-methyl-3-phenylpropyl)-2-({[({4-[(trifluoromethyl)oxy]phenyl}oxy)acetyl]amino}methyl)-1,3-thiazole-4-carboxamide | B |
| 153 | N-[(1S)-1,2-dimethylpropyl]-2-({[({4-[(trifluoromethyl)oxy]phenyl}oxy)acetyl]amino}methyl)-1,3-thiazole-4-carboxamide | B |
| 154 | N-{[3-(methyloxy)phenyl]methyl}-2-({[({4-[(trifluoromethyl)oxy]phenyl}oxy)acetyl]amino}methyl)-1,3-thiazole-4-carboxamide | B |
| 155 | N-{2-[3,4-bis(methyloxy)phenyl]ethyl}-2-({[({4-[(trifluoromethyl)oxy]phenyl}oxy)acetyl]amino}methyl)-1,3-oxazole-4-carboxamide | B |
| 156 | 2-({[({4-[(trifluoromethyl)oxy]phenyl}oxy)acetyl]amino}methyl)-N-{[3-(trifluoromethyl)phenyl]methyl}-1,3-thiazole-4-carboxamide | B |
| 157 | N-[(3-iodophenyl)methyl]-2-({[({4-[(trifluoromethyl)oxy]phenyl}oxy)acetyl]amino}methyl)-1,3-thiazole-4-carboxamide | B |
| 158 | N-{[2-fluoro-3-(trifluoromethyl)phenyl]methyl}-2-({[({4-[(trifluoromethyl)oxy]phenyl}oxy)acetyl]amino}methyl)-1,3-thiazole-4-carboxamide | B |
| 159 | N-[2-(2-thienyl)ethyl]-2-({[({4-[(trifluoromethyl)oxy]phenyl}oxy)acetyl]amino}methyl)-1,3-oxazole-4-carboxamide | B |
| 160 | N-[2-(2,4-dichlorophenyl)ethyl]-2-({[({4-[(trifluoromethyl)oxy]phenyl}oxy)acetyl]amino}methyl)-1,3-thiazole-4-carboxamide | B |

TABLE 2-continued

| Entry | Name | ALK IC$_{50}$ |
|---|---|---|
| 161 | N-[2-(3-chlorophenyl)ethyl]-2-[({[(3-chlorophenyl)oxy]acetyl}amino)methyl]-1,3-thiazole-4-carboxamide | B |
| 162 | N-[(1S)-1-(4-methylphenyl)ethyl]-2-({[({4-[(trifluoromethyl)oxy]phenyl}oxy)acetyl]amino}methyl)-1,3-thiazole-4-carboxamide | B |
| 163 | N-{[2-chloro-6-(phenyloxy)phenyl]methyl}-2-({[({4-[(trifluoromethyl)oxy]phenyl}oxy)acetyl]amino}methyl)-1,3-thiazole-4-carboxamide | B |
| 164 | N-(2-thienylmethyl)-2-({[({4-[(trifluoromethyl)oxy]phenyl}oxy)acetyl]amino}methyl)-1,3-thiazole-4-carboxamide | B |
| 165 | N-[(1R)-1,2,3,4-tetrahydronaphthalen-1-yl]-2-({[({4-[(trifluoromethyl)oxy]phenyl}oxy)acetyl]amino}methyl)-1,3-thiazole-4-carboxamide | B |
| 166 | N-[(2,4-dichloro-6-methylphenyl)methyl]-2-({[({4-[(trifluoromethyl)oxy]phenyl}oxy)acetyl]amino}methyl)-1,3-thiazole-4-carboxamide | B |
| 167 | N-(diphenylmethyl)-2-({[({4-[(trifluoromethyl)oxy]phenyl}oxy)acetyl]amino}methyl)-1,3-thiazole-4-carboxamide | B |
| 168 | N-[2-(3-chlorophenyl)ethyl]-2-[({[(4-methylphenyl)amino]carbonyl}amino)methyl]-1,3-thiazole-4-carboxamide | B |
| 169 | N-[2-(2-fluorophenyl)ethyl]-2-{[(naphthalen-2-ylacetyl)amino]methyl}-1,3-thiazole-4-carboxamide | B |
| 170 | N-[(4-methylphenyl)methyl]-2-({[({4-[(trifluoromethyl)oxy]phenyl}oxy)acetyl]amino}methyl)-1,3-thiazole-4-carboxamide | B |
| 171 | N-(1-ethylpropyl)-2-({[({4-[(trifluoromethyl)oxy]phenyl}oxy)acetyl]amino}methyl)-1,3-thiazole-4-carboxamide | B |
| 172 | N-(cyclohexylmethyl)-2-({[({4-[(trifluoromethyl)oxy]phenyl}oxy)acetyl]amino}methyl)-1,3-thiazole-4-carboxamide | B |
| 173 | N-[2-(3-chlorophenyl)ethyl]-2-{[({[4-(methylthio)phenyl]amino}carbonyl)amino]methyl}-1,3-thiazole-4-carboxamide | B |
| 174 | N-{[4-fluoro-3-(trifluoromethyl)phenyl]methyl}-2-({[({4-[(trifluoromethyl)oxy]phenyl}oxy)acetyl]amino}methyl)-1,3-thiazole-4-carboxamide | B |
| 175 | N-(3,3-dimethylbutyl)-2-({[({4-[(trifluoromethyl)oxy]phenyl}oxy)acetyl]amino}methyl)-1,3-thiazole-4-carboxamide | B |
| 176 | N-(2-cyclohex-1-en-1-ylethyl)-2-({[({4-[(trifluoromethyl)oxy]phenyl}oxy)acetyl]amino}methyl)-1,3-oxazole-4-carboxamide | B |
| 177 | N-butyl-2-({[({4-[(trifluoromethyl)oxy]phenyl}oxy)acetyl]amino}methyl)-1,3-thiazole-4-carboxamide | B |
| 178 | N-{[4-(methyloxy)phenyl]methyl}-2-({[({4-[(trifluoromethyl)oxy]phenyl}oxy)acetyl]amino}methyl)-1,3-thiazole-4-carboxamide | B |
| 179 | N-(1-methylhexyl)-2-({[({4-[(trifluoromethyl)oxy]phenyl}oxy)acetyl]amino}methyl)-1,3-thiazole-4-carboxamide | B |
| 180 | N-(1-ethynylcyclohexyl)-2-({[({4-[(trifluoromethyl)oxy]phenyl}oxy)acetyl]amino}methyl)-1,3-thiazole-4-carboxamide | B |
| 181 | 2-({[({4-[(trifluoromethyl)oxy]phenyl}oxy)acetyl]amino}methyl)-N-{2-[3-(trifluoromethyl)phenyl]ethyl}-1,3-oxazole-4-carboxamide | B |
| 182 | N-(2,3-dihydro-1H-inden-1-yl)-2-({[({4-[(trifluoromethyl)oxy]phenyl}oxy)acetyl]amino}methyl)-1,3-thiazole-4-carboxamide | B |
| 183 | N-{(1S)-1-[4-(methyloxy)phenyl]ethyl}-2-({[({4-[(trifluoromethyl)oxy]phenyl}oxy)acetyl]amino}methyl)-1,3-thiazole-4-carboxamide | B |
| 184 | N-[2-(3-chlorophenyl)ethyl]-2-{[({[4-(ethyloxy)phenyl]amino}carbonyl)amino]methyl}-1,3-thiazole-4-carboxamide | B |
| 185 | N-[(3,4-difluorophenyl)methyl]-2-({[({4-[(trifluoromethyl)oxy]phenyl}oxy)acetyl]amino}methyl)-1,3-thiazole-4-carboxamide | B |
| 186 | N-{[2-(methylthio)phenyl]methyl}-2-({[({4-[(trifluoromethyl)oxy]phenyl}oxy)acetyl]amino}methyl)-1,3-oxazole-4-carboxamide | B |

TABLE 2-continued

| Entry | Name | ALK IC$_{50}$ |
|---|---|---|
| 187 | N-{[3,4-bis(methyloxy)phenyl]methyl}-2-({[({4-[(trifluoromethyl)oxy]phenyl}oxy)acetyl]amino}methyl)-1,3-thiazole-4-carboxamide | B |
| 188 | Nalpha-{[2-({[({4-[(trifluoromethyl)oxy]phenyl}oxy)acetyl]amino}methyl)-1,3-thiazol-4-yl]carbonyl}-L-phenylalaninamide | B |
| 189 | N-(7-methyloctyl)-2-({[({4-[(trifluoromethyl)oxy]phenyl}oxy)acetyl]amino}methyl)-1,3-thiazole-4-carboxamide | B |
| 190 | N-(pyridin-2-ylmethyl)-2-({[({4-[(trifluoromethyl)oxy]phenyl}oxy)acetyl]amino}methyl)-1,3-thiazole-4-carboxamide | B |
| 191 | N-[(3-chloro-4-fluorophenyl)methyl]-2-({[({4-[(trifluoromethyl)oxy]phenyl}oxy)acetyl]amino}methyl)-1,3-thiazole-4-carboxamide | B |
| 192 | 2-[({[4-(1-methylethyl)phenyl]acetyl}amino)methyl]-N-{[2-(methyloxy)phenyl]methyl}-1,3-thiazole-4-carboxamide | B |
| 193 | N-hexyl-N-methyl-2-({[({4-[(trifluoromethyl)oxy]phenyl}oxy)acetyl]amino}methyl)-1,3-thiazole-4-carboxamide | B |
| 194 | N-(phenylmethyl)-2-({[({4-[(trifluoromethyl)oxy]phenyl}oxy)acetyl]amino}methyl)-1,3-thiazole-4-carboxamide | B |
| 195 | N-[2-(methylthio)ethyl]-2-({[({4-[(trifluoromethyl)oxy]phenyl}oxy)acetyl]amino}methyl)-1,3-thiazole-4-carboxamide | B |
| 196 | N-(1,1,3,3-tetramethylbutyl)-2-({[({4-[(trifluoromethyl)oxy]phenyl}oxy)acetyl]amino}methyl)-1,3-thiazole-4-carboxamide | B |
| 197 | N-(1,2-dimethylpropyl)-2-({[({4-[(trifluoromethyl)oxy]phenyl}oxy)acetyl]amino}methyl)-1,3-thiazole-4-carboxamide | B |
| 198 | 2-[(4-chlorophenyl)oxy]-N-({4-[({[2-(methyloxy)phenyl]methyl}amino)carbonyl]-1,3-thiazol-2-yl}methyl)pyridine-3-carboxamide | B |
| 199 | N-(1,2,3,4-tetrahydronaphthalen-1-yl)-2-({[({4-[(trifluoromethyl)oxy]phenyl}oxy)acetyl]amino}methyl)-1,3-thiazole-4-carboxamide | B |
| 200 | N-(2-ethylhexyl)-2-({[({4-[(trifluoromethyl)oxy]phenyl}oxy)acetyl]amino}methyl)-1,3-thiazole-4-carboxamide | B |
| 201 | N-[2-(4-fluorophenyl)ethyl]-2-({[({4-[(trifluoromethyl)oxy]phenyl}oxy)acetyl]amino}methyl)-1,3-oxazole-4-carboxamide | B |
| 202 | N~2~-{[2-({[({4-[(trifluoromethyl)oxy]phenyl}oxy)acetyl]amino}methyl)-1,3-thiazol-4-yl]carbonyl}-D-leucinamide | B |
| 203 | N-{[2-(methyloxy)phenyl]methyl}-2-({[({4-[(trifluoromethyl)oxy]phenyl}oxy)acetyl]amino}methyl)-1,3-oxazole-4-carboxamide | B |
| 204 | N-[1-(4-bromophenyl)ethyl]-2-({[({4-[(trifluoromethyl)oxy]phenyl}oxy)acetyl]amino}methyl)-1,3-thiazole-4-carboxamide | B |
| 205 | N-(2-morpholin-4-ylethyl)-2-({[({4-[(trifluoromethyl)oxy]phenyl}oxy)acetyl]amino}methyl)-1,3-thiazole-4-carboxamide | B |
| 206 | N-[(4-fluorophenyl)methyl]-2-({[({4-[(trifluoromethyl)oxy]phenyl}oxy)acetyl]amino}methyl)-1,3-thiazole-4-carboxamide | B |
| 207 | N-{2-[3,5-bis(methyloxy)phenyl]ethyl}-2-({[({4-[(trifluoromethyl)oxy]phenyl}oxy)acetyl]amino}methyl)-1,3-oxazole-4-carboxamide | B |
| 208 | N-[2-(3-chlorophenyl)ethyl]-2-({[[(3E)-4-phenylbut-3-enoyl]amino}methyl)-1,3-thiazole-4-carboxamide | B |
| 209 | N-cyclohexyl-2-({[({4-[(trifluoromethyl)oxy]phenyl}oxy)acetyl]amino}methyl)-1,3-thiazole-4-carboxamide | B |
| 210 | N-(2-methylbutyl)-2-({[({4-[(trifluoromethyl)oxy]phenyl}oxy)acetyl]amino}methyl)-1,3-thiazole-4-carboxamide | B |
| 211 | N-[2-(3,4-dimethylphenyl)ethyl]-2-({[({4-[(trifluoromethyl)oxy]phenyl}oxy)acetyl]amino}methyl)-1,3-oxazole-4-carboxamide | B |
| 212 | N-(1,5-dimethylhexyl)-2-({[({4-[(trifluoromethyl)oxy]phenyl}oxy)acetyl]amino}methyl)-1,3-thiazole-4-carboxamide | B |

TABLE 2-continued

| Entry | Name | ALK IC$_{50}$ |
|---|---|---|
| 213 | N-{2-[2-(phenyloxy)phenyl]ethyl}-2-({[({4-[(trifluoromethyl)oxy]phenyl}oxy)acetyl]amino}methyl)-1,3-thiazole-4-carboxamide | B |
| 214 | 2-{[({[4-(butyloxy)phenyl]amino}carbonyl)amino]methyl}-N-{2-(methyloxy)phenyl]methyl}-1,3-thiazole-4-carboxamide | B |
| 215 | 2-[({[(4-chlorophenyl)oxy]acetyl}amino)methyl]-N-[2-(2-fluorophenyl)ethyl]-1,3-thiazole-4-carboxamide | B |
| 216 | N-(cyclopropylmethyl)-2-({[({4-[(trifluoromethyl)oxy]phenyl}oxy)acetyl]amino}methyl)-1,3-thiazole-4-carboxamide | B |
| 217 | N-[2-(3-chlorophenyl)ethyl]-2-{[({[(1R,2S)-2-phenylcyclopropyl]amino}carbonyl)amino]methyl}-1,3-thiazole-4-carboxamide | B |
| 218 | N-{(1R,2R)-2-[(phenylmethyl)oxy]cyclopentyl}-2-({[({4-[(trifluoromethyl)oxy]phenyl}oxy)acetyl]amino}methyl)-1,3-thiazole-4-carboxamide | B |
| 219 | N-(2-pyridin-4-ylethyl)-2-({[({4-[(trifluoromethyl)oxy]phenyl}oxy)acetyl]amino}methyl)-1,3-oxazole-4-carboxamide | C |
| 220 | N-(1-methylheptyl)-2-({[({4-[(trifluoromethyl)oxy]phenyl}oxy)acetyl]amino}methyl)-1,3-thiazole-4-carboxamide | C |
| 221 | N-{[4-({[2-(3-chlorophenyl)ethyl]amino}carbonyl)-1,3-thiazol-2-yl]methyl}-N~2~-(phenylcarbonyl)methioninamide | C |
| 222 | N-(1,2-diphenylethyl)-2-({[({4-[(trifluoromethyl)oxy]phenyl}oxy)acetyl]amino}methyl)-1,3-thiazole-4-carboxamide | C |
| 223 | N-{[2,3-bis(methyloxy)phenyl]methyl}-2-({[({4-[(trifluoromethyl)oxy]phenyl}oxy)acetyl]amino}methyl)-1,3-oxazole-4-carboxamide | C |
| 224 | N-{2-[4-(methyloxy)phenyl]ethyl}-2-({[({4-[(trifluoromethyl)oxy]phenyl}oxy)acetyl]amino}methyl)-1,3-oxazole-4-carboxamide | C |
| 225 | N-[2-(4-methylphenyl)ethyl]-2-({[({4-[(trifluoromethyl)oxy]phenyl}oxy)acetyl]amino}methyl)-1,3-oxazole-4-carboxamide | C |
| 226 | N-(2,2-diphenylethyl)-2-({[({4-[(trifluoromethyl)oxy]phenyl}oxy)acetyl]amino}methyl)-1,3-oxazole-4-carboxamide | C |
| 227 | N-[(4-chlorophenyl)methyl]-2-({[({4-[(trifluoromethyl)oxy]phenyl}oxy)acetyl]amino}methyl)-1,3-thiazole-4-carboxamide | C |
| 228 | N-cyclopentyl-2-({[({4-[(trifluoromethyl)oxy]phenyl}oxy)acetyl]amino}methyl)-1,3-thiazole-4-carboxamide | C |
| 229 | N-{[2-(methyloxy)phenyl]methyl}-2-{[(naphthalen-2-ylacetyl)amino]methyl}-1,3-thiazole-4-carboxamide | C |
| 230 | N-{2-[3-(ethyloxy)phenyl]ethyl}-2-({[({4-[(trifluoromethyl)oxy]phenyl}oxy)acetyl]amino}methyl)-1,3-oxazole-4-carboxamide | C |
| 231 | N-[2-(4-bromophenyl)ethyl]-2-({[({4-[(trifluoromethyl)oxy]phenyl}oxy)acetyl]amino}methyl)-1,3-oxazole-4-carboxamide | C |
| 232 | N-[2-(3-chlorophenyl)ethyl]-2-[({[4-(methylthio)phenyl]acetyl}amino)methyl]-1,3-thiazole-4-carboxamide | C |
| 233 | 2-({[({4-[(trifluoromethyl)oxy]phenyl}oxy)acetyl]amino}methyl)-N-[(1R)-1,2,2-trimethylpropyl]-1,3-thiazole-4-carboxamide | C |
| 234 | N-{2-[3-(methyloxy)phenyl]ethyl}-2-({[({4-[(trifluoromethyl)oxy]phenyl}oxy)acetyl]amino}methyl)-1,3-oxazole-4-carboxamide | C |
| 235 | N-{[2-(ethyloxy)phenyl]methyl}-2-({[({4-[(trifluoromethyl)oxy]phenyl}oxy)acetyl]amino}methyl)-1,3-oxazole-4-carboxamide | C |
| 236 | 2-[({[1-(4-chlorophenyl)cyclopropyl]carbonyl}amino)methyl]-N-[2-(3-chlorophenyl)ethyl]-1,3-thiazole-4-carboxamide | C |
| 237 | N-{[4-(dimethylamino)phenyl]methyl}-2-({[({4-[(trifluoromethyl)oxy]phenyl}oxy)acetyl]amino}methyl)-1,3-thiazole-4-carboxamide | C |
| 238 | N-(2-cyanoethyl)-N-hexyl-2-({[({4-[(trifluoromethyl)oxy]phenyl}oxy)acetyl]amino}methyl)-1,3-thiazole-4-carboxamide | C |
| 239 | 2-[({[(4-bromophenyl)oxy]acetyl}amino)methyl]-N-[2-(2-fluorophenyl)ethyl]-1,3-thiazole-4-carboxamide | C |
| 240 | N-[(2S)-2-phenylpropyl]-2-({[({4-[(trifluoromethyl)oxy]phenyl}oxy)acetyl]amino}methyl)-1,3-oxazole-4-carboxamide | C |

TABLE 2-continued

| Entry | Name | ALK IC$_{50}$ |
|---|---|---|
| 241 | N-(pyridin-3-ylmethyl)-2-({[({4-[(trifluoromethyl)oxy]phenyl}oxy)acetyl]amino}methyl)-1,3-thiazole-4-carboxamide | C |
| 242 | N-(2-phenylethyl)-2-({[({4-[(trifluoromethyl)oxy]phenyl}oxy)acetyl]amino}methyl)-1,3-oxazole-4-carboxamide | C |
| 243 | N-[(4-{[3-methyl-4-(4-methylphenyl)piperazin-1-yl]carbonyl}-1,3-thiazol-2-yl)methyl]-2-({4-[(trifluoromethyl)oxy]phenyl}oxy)acetamide | C |
| 244 | N-{[4-fluoro-2-(trifluoromethyl)phenyl]methyl}-2-({[({4-[(trifluoromethyl)oxy]phenyl}oxy)acetyl]amino}methyl)-1,3-thiazole-4-carboxamide | C |
| 245 | N-({4-[(4-propylpiperidin-1-yl)carbonyl]-1,3-thiazol-2-yl}methyl)-2-({4-[(trifluoromethyl)oxy]phenyl}oxy)acetamide | C |
| 246 | N-[2-(4-chlorophenyl)ethyl]-2-({[({4-[(trifluoromethyl)oxy]phenyl}oxy)acetyl]amino}methyl)-1,3-oxazole-4-carboxamide | C |
| 247 | N-[2-(1-methylpyrrolidin-2-yl)ethyl]-2-({[({4-[(trifluoromethyl)oxy]phenyl}oxy)acetyl]amino}methyl)-1,3-thiazole-4-carboxamide | C |
| 248 | N-{[2,3-bis(methyloxy)phenyl]methyl}-2-{[({[4-(butyloxy)phenyl]amino}carbonyl)amino]methyl}-1,3-thiazole-4-carboxamide | C |
| 249 | N-(furan-2-ylmethyl)-2-({[({4-[(trifluoromethyl)oxy]phenyl}oxy)acetyl]amino}methyl)-1,3-thiazole-4-carboxamide | C |
| 250 | N-{2-[3-(ethyloxy)-4-(methyloxy)phenyl]ethyl}-2-({[({4-[(trifluoromethyl)oxy]phenyl}oxy)acetyl]amino}methyl)-1,3-oxazole-4-carboxamide | C |
| 251 | N-[2-(1H-indol-3-yl)ethyl]-2-({[({4-[(trifluoromethyl)oxy]phenyl}oxy)acetyl]amino}methyl)-1,3-oxazole-4-carboxamide | C |
| 252 | N-{[4-(octahydroquinolin-1(2H)-ylcarbonyl)-1,3-thiazol-2-yl]methyl}-2-({4-[(trifluoromethyl)oxy]phenyl}oxy)acetamide | C |
| 253 | N-({4-[(3-methyl-4-phenylpiperazin-1-yl)carbonyl]-1,3-thiazol-2-yl}methyl)-2-({4-[(trifluoromethyl)oxy]phenyl}oxy)acetamide | C |
| 254 | 1,1-dimethylethyl(1-{[2-({[({4-[(trifluoromethyl)oxy]phenyl}oxy)acetyl]amino}methyl)-1,3-thiazol-4-yl]carbonyl}piperidin-4-yl)carbamate | C |
| 255 | N-[(4-{[(2R,6S)-2,6-dimethylmorpholin-4-yl]carbonyl}-1,3-thiazol-2-yl)methyl]-2-({4-[(trifluoromethyl)oxy]phenyl}oxy)acetamide | C |
| 256 | N-{[2,3-bis(methyloxy)phenyl]methyl}-2-{[(naphthalen-2-ylacetyl)amino]methyl}-1,3-thiazole-4-carboxamide | C |
| 257 | N-(2-methylcyclohexyl)-2-({[({4-[(trifluoromethyl)oxy]phenyl}oxy)acetyl]amino}methyl)-1,3-oxazole-4-carboxamide | C |
| 258 | N-[(2,4-difluorophenyl)methyl]-2-({[({4-[(trifluoromethyl)oxy]phenyl}oxy)acetyl]amino}methyl)-1,3-thiazole-4-carboxamide | C |
| 259 | N-(2-phenylpropyl)-2-({[({4-[(trifluoromethyl)oxy]phenyl}oxy)acetyl]amino}methyl)-1,3-oxazole-4-carboxamide | C |
| 260 | N-(3,3-diphenylpropyl)-2-({[({4-[(trifluoromethyl)oxy]phenyl}oxy)acetyl]amino}methyl)-1,3-thiazole-4-carboxamide | C |
| 261 | N-[(2-chlorophenyl)methyl]-2-({[({4-[(trifluoromethyl)oxy]phenyl}oxy)acetyl]amino}methyl)-1,3-oxazole-4-carboxamide | C |
| 262 | N-(1,4-dimethylpentyl)-2-({[({4-[(trifluoromethyl)oxy]phenyl}oxy)acetyl]amino}methyl)-1,3-thiazole-4-carboxamide | C |
| 263 | 2-[({[(4-chlorophenyl)oxy]acetyl}amino)methyl]-N-{[2-(methyloxy)phenyl]methyl}-1,3-thiazole-4-carboxamide | C |
| 264 | N-[(1S)-1-cyclohexylethyl]-2-({[({4-[(trifluoromethyl)oxy]phenyl}oxy)acetyl]amino}methyl)-1,3-oxazole-4-carboxamide | C |
| 265 | N-(tetrahydrofuran-2-ylmethyl)-2-({[({4-[(trifluoromethyl)oxy]phenyl}oxy)acetyl]amino}methyl)-1,3-thiazole-4-carboxamide | C |
| 266 | N-({4-[(4aR,8aS)-octahydroisoquinolin-2(1H)-ylcarbonyl]-1,3-thiazol-2-yl}methyl)-2-({4-[(trifluoromethyl)oxy]phenyl}oxy)acetamide | C |
| 267 | N-(3-morpholin-4-ylpropyl)-2-({[({4-[(trifluoromethyl)oxy]phenyl}oxy)acetyl]amino}methyl)-1,3-thiazole-4-carboxamide | C |
| 268 | N-[1-methyl-2-(methyloxy)ethyl]-2-({[({4-[(trifluoromethyl)oxy]phenyl}oxy)acetyl]amino}methyl)-1,3-thiazole-4-carboxamide | C |

TABLE 2-continued

| Entry | Name | ALK IC$_{50}$ |
|---|---|---|
| 269 | N-[3-(methyloxy)propyl]-2-({[({4-[(trifluoromethyl)oxy]phenyl}oxy)acetyl]amino}methyl)-1,3-thiazole-4-carboxamide | C |
| 270 | N,N-diethyl-1-{[2-({[({4-[(trifluoromethyl)oxy]phenyl}oxy)acetyl]amino}methyl)-1,3-thiazol-4-yl]carbonyl}piperidine-3-carboxamide | C |
| 271 | N-({4-[(4aS,8aS)-octahydroisoquinolin-2(1H)-ylcarbonyl]-1,3-thiazol-2-yl}methyl)-2-({4-[(trifluoromethyl)oxy]phenyl}oxy)acetamide | C |
| 272 | 1-{[2-({[({4-[(trifluoromethyl)oxy]phenyl}oxy)acetyl]amino}methyl)-1,3-thiazol-4-yl]carbonyl}piperidine-4-carboxamide | C |
| 273 | N-[2-(2-chlorophenyl)ethyl]-2-({[({4-[(trifluoromethyl)oxy]phenyl}oxy)acetyl]amino}methyl)-1,3-oxazole-4-carboxamide | C |
| 274 | N-(2-pyrrolidin-1-ylethyl)-2-({[({4-[(trifluoromethyl)oxy]phenyl}oxy)acetyl]amino}methyl)-1,3-thiazole-4-carboxamide | C |
| 275 | N-[(1-ethylpyrrolidin-2-yl)methyl]-2-({[({4-[(trifluoromethyl)oxy]phenyl}oxy)acetyl]amino}methyl)-1,3-thiazole-4-carboxamide | C |
| 276 | N-[2-(2-fluorophenyl)ethyl]-2-({[(3E)-4-phenylbut-3-enoyl]amino}methyl)-1,3-thiazole-4-carboxamide | C |
| 277 | 2-[({[(4-bromophenyl)oxy]acetyl}amino)methyl]-N-{[2-(methyloxy)phenyl]methyl}-1,3-thiazole-4-carboxamide | C |
| 278 | 1,1-dimethylethyl (1-{[2-({[({4-[(trifluoromethyl)oxy]phenyl}oxy)acetyl]amino}methyl)-1,3-thiazol-4-yl]carbonyl}pyrrolidin-3-yl)carbamate | C |
| 279 | N-({4-[(4-pyridin-2-ylpiperazin-1-yl)carbonyl]-1,3-thiazol-2-yl}methyl)-2-({4-[(trifluoromethyl)oxy]phenyl}oxy)acetamide | C |
| 280 | N-(2,2,2-trifluoroethyl)-2-({[({4-[(trifluoromethyl)oxy]phenyl}oxy)acetyl]amino}methyl)-1,3-thiazole-4-carboxamide | C |
| 281 | N-[2-(acetylamino)ethyl]-2-({[({4-[(trifluoromethyl)oxy]phenyl}oxy)acetyl]amino}methyl)-1,3-thiazole-4-carboxamide | C |
| 282 | N-({4-[(3,5-dimethylpiperidin-1-yl)carbonyl]-1,3-thiazol-2-yl}methyl)-2-({4-[(trifluoromethyl)oxy]phenyl}oxy)acetamide | C |
| 283 | ethyl 4-({[2-({[({4-[(trifluoromethyl)oxy]phenyl}oxy)acetyl]amino}methyl)-1,3-thiazol-4-yl]carbonyl}amino)piperidine-1-carboxylate | C |
| 284 | N-{[2-(methyloxy)phenyl]methyl}-2-({[(3E)-4-phenylbut-3-enoyl]amino}methyl)-1,3-thiazole-4-carboxamide | C |
| 285 | N-(pyridin-4-ylmethyl)-2-({[({4-[(trifluoromethyl)oxy]phenyl}oxy)acetyl]amino}methyl)-1,3-thiazole-4-carboxamide | C |
| 286 | N-[3-(2-oxopyrrolidin-1-yl)propyl]-2-({[({4-[(trifluoromethyl)oxy]phenyl}oxy)acetyl]amino}methyl)-1,3-thiazole-4-carboxamide | C |
| 287 | N-[2-(methyloxy)ethyl]-2-({[({4-[(trifluoromethyl)oxy]phenyl}oxy)acetyl]amino}methyl)-1,3-thiazole-4-carboxamide | C |
| 288 | N-[(2-methylphenyl)methyl]-2-({[({4-[(trifluoromethyl)oxy]phenyl}oxy)acetyl]amino}methyl)-1,3-oxazole-4-carboxamide | C |
| 289 | N-({4-[(3-methylpiperidin-1-yl)carbonyl]-1,3-thiazol-2-yl}methyl)-2-({4-[(trifluoromethyl)oxy]phenyl}oxy)acetamide | C |
| 290 | N-(2-piperidin-1-ylethyl)-2-({[({4-[(trifluoromethyl)oxy]phenyl}oxy)acetyl]amino}methyl)-1,3-thiazole-4-carboxamide | C |
| 291 | N-[(3,4-dichlorophenyl)methyl]-2-({[({4-[(trifluoromethyl)oxy]phenyl}oxy)acetyl]amino}methyl)-1,3-oxazole-4-carboxamide | C |
| 292 | N-[(4-fluorophenyl)methyl]-2-({[({4-[(trifluoromethyl)oxy]phenyl}oxy)acetyl]amino}methyl)-1,3-oxazole-4-carboxamide | C |
| 293 | N-(1,2,3,4-tetrahydronaphthalen-1-yl)-2-({[({4-[(trifluoromethyl)oxy]phenyl}oxy)acetyl]amino}methyl)-1,3-oxazole-4-carboxamide | C |
| 294 | N-{[4-(octahydroisoquinolin-2(1H)-ylcarbonyl)-1,3-thiazol-2-yl]methyl}-2-({4-[(trifluoromethyl)oxy]phenyl}oxy)acetamide | C |
| 295 | 1,1-dimethylethyl methyl(1-{[2-({[({4-[(trifluoromethyl)oxy]phenyl}oxy)acetyl]amino}methyl)-1,3-thiazol-4-yl]carbonyl}pyrrolidin-3-yl)carbamate | C |
| 296 | N-(2-pyridin-2-ylethyl)-2-({[({4-[(trifluoromethyl)oxy]phenyl}oxy)acetyl]amino}methyl)-1,3-oxazole-4-carboxamide | C |

TABLE 2-continued

| Entry | Name | ALK IC$_{50}$ |
|---|---|---|
| 297 | N-(phenylmethyl)-2-({[({4-[(trifluoromethyl)oxy]phenyl}oxy)acetyl]amino}methyl)-1,3-oxazole-4-carboxamide | C |
| 298 | {4-[(trifluoromethyl)oxy]phenyl}methyl {4-({[2-(3-chlorophenyl)ethyl]amino}carbonyl)-1,3-thiazol-2-yl]methyl}carbamate | C |
| 299 | N-[2-(3-chlorophenyl)ethyl]-5-({[({4-[(trifluoromethyl)oxy]phenyl}oxy)acetyl]amino}methyl)isoxazole-3-carboxamide | D |
| 300 | 2-(aminomethyl)-N-[2-(3-chlorophenyl)ethyl]-1,3-thiazole-4-carboxamide | D |
| 301 | (4E,6Z,8S,9S,10E,12S,13R,14R,16S,17R)-4,10,12,16-tetramethyl-8,13,14,17-tetrakis(methyloxy)-3,20,22-trioxo-2-azabicyclo[16.3.1]docosa-1(21),4,6,10,18-pentaen-9-yl carbamate | D |
| 302 | 2-({[({4-[(trifluoromethyl)oxy]phenyl}oxy)acetyl]amino}methyl)-1,3-thiazole-4-carboxylic acid | D |
| 303 | 2-(aminomethyl)-N-{[2,3-bis(methyloxy)phenyl]methyl}-1,3-thiazole-4-carboxamide | D |
| 304 | 2-(aminomethyl)-N-{[2-(methyloxy)phenyl]methyl}-1,3-thiazole-4-carboxamide | D |
| 305 | 2-(aminomethyl)-N-[2-(2-fluorophenyl)ethyl]-1,3-thiazole-4-carboxamide | D |
| 306 | N-[2-(3-chlorophenyl)ethyl]-2-({[({4-[(trifluoromethyl)oxy]phenyl}oxy)acetyl]amino}methyl)-1H-imidazole-4-carboxamide | D |
| 307 | 2-(aminomethyl)-N-[2-(3-chlorophenyl)ethyl]-1,3-oxazole-4-carboxamide | D |
| 308 | 2-({[({4-[(trifluoromethyl)oxy]phenyl}oxy)acetyl]amino}methyl)-1,3-oxazole-4-carboxylic acid | D |
| 309 | N-[2-(3-chlorophenyl)ethyl]-2-{[({4-[(trifluoromethyl)oxy]phenyl}methyl)amino]methyl}-1,3-thiazole-4-carboxamide | D |
| 310 | N-[(4-{[4-ethyl-2-methyl-2-(3-methylbutyl)-1,3-oxazolidin-3-yl]carbonyl}-1,3-thiazol-2-yl)methyl]-2-({4-[(trifluoromethyl)oxy]phenyl}oxy)acetamide | D |
| 311 | N-[(4-{[3-(diethylamino)pyrrolidin-1-yl]carbonyl}-1,3-thiazol-2-yl)methyl]-2-({4-[(trifluoromethyl)oxy]phenyl}oxy)acetamide | D |

As discussed above, the names of the compounds are generated using the nomenclature engine published by ACD/Labs of Toronto Canada. In order to further describe the compounds of the present invention, a representative number of compounds set forth in Table 1 are provided below in Table 3, wherein the structure of the compound is provided as well as the name generated by the nomenclature engine. These examples are provided to further clarify the compounds of the present invention.

TABLE 3

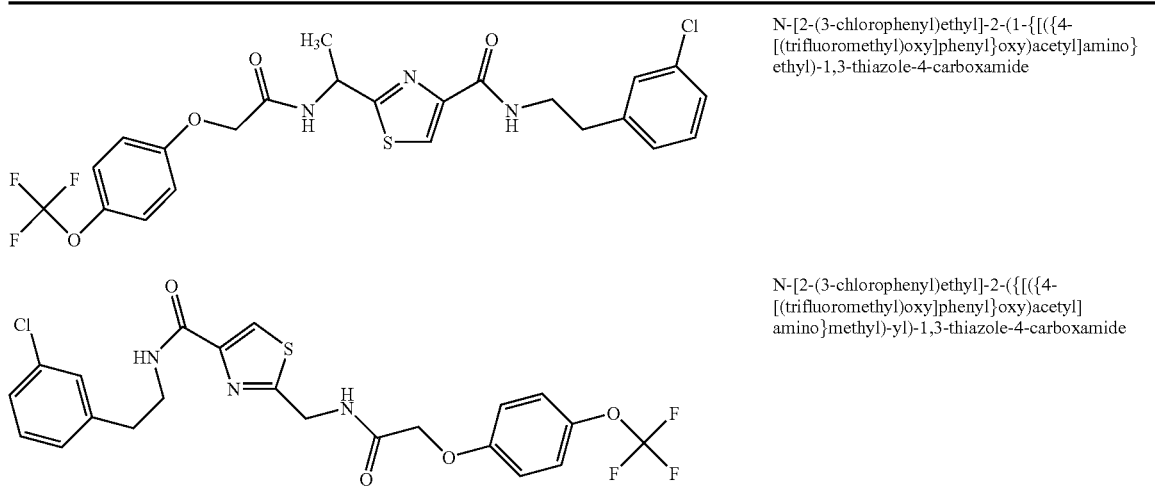

N-[2-(3-chlorophenyl)ethyl]-2-(1-{[({4-[(trifluoromethyl)oxy]phenyl}oxy)acetyl]amino}ethyl)-1,3-thiazole-4-carboxamide N-[2-(3-chlorophenyl)ethyl]-2-({[({4-[(trifluoromethyl)oxy]phenyl}oxy)acetyl]amino}methyl)-yl)-1,3-thiazole-4-carboxamide TABLE 3-continued

| | |
|---|---|
| 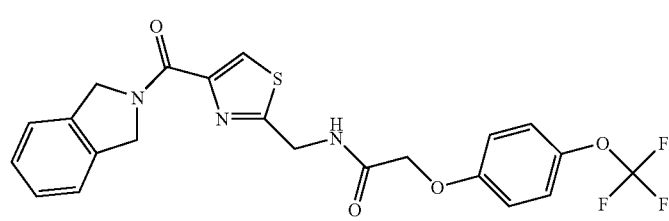 | N-{[4-(1,3-dihydro-2H-isoindol-2-ylcarbonyl)-1,3-thiazol-2-yl]methyl}-2-({4-[(trifluoromethyl)oxy]phenyl}oxy)acetamide |
| 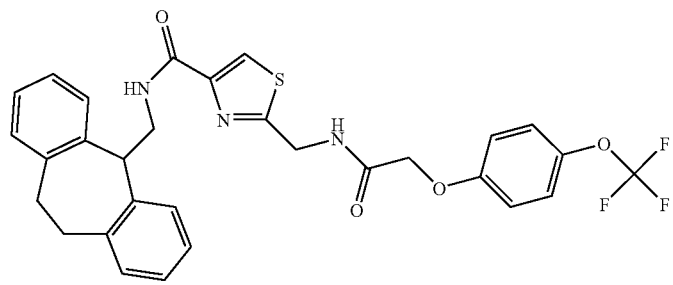 | N-(10,11-dihydro-5H-dibenzo[a,d]cyclohepten-5-ylmethyl)-2-({[({4-[(trifluoromethyl)oxy]phenyl}oxy)acetyl]amino}methyl)-1,3-thiazole-4-carboxamide |
| 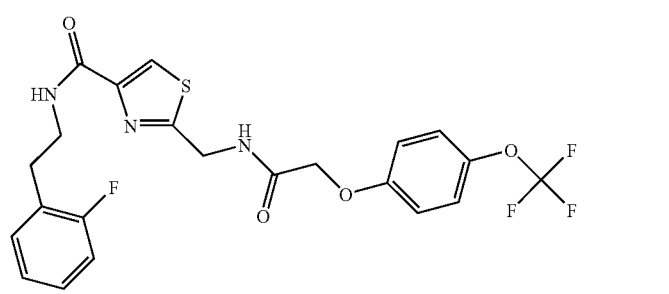 | N-[2-(2-fluorophenyl)ethyl]-2-({[({4-[(trifluoromethyl)oxy]phenyl}oxy)acetyl]amino}methyl-1,3-thiazole-4-carboxamide |
| 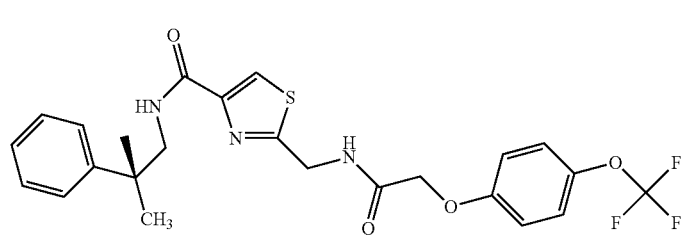 Chiral | N-[(2R)-2-phenylpropyl]-2-({[({4-[(trifluoromethyl)oxy]phenyl}oxy)acetyl]amino}methyl)-1,3-thiazole-4-carboxamide |
| 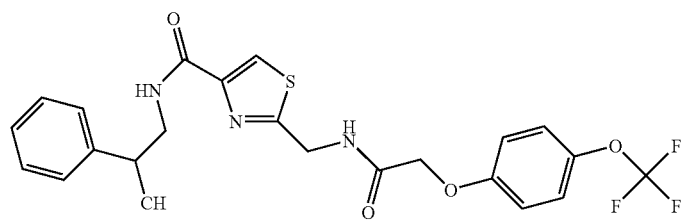 | N-(2-phenylpropyl)-2-({[({4-[(trifluoromethyl)oxy]phenyl}oxy)acetyl]amino}methyl)-1,3-thiazole-4-carboxamide |
| 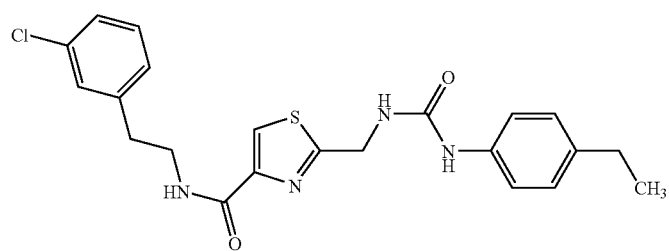 | N-[2-(3-chlorophenyl)ethyl]-2-[({[(4-ethylphenyl)amino]carbonyl}amino)methyl]-1,3-thiazole-4-carboxamide |

TABLE 3-continued

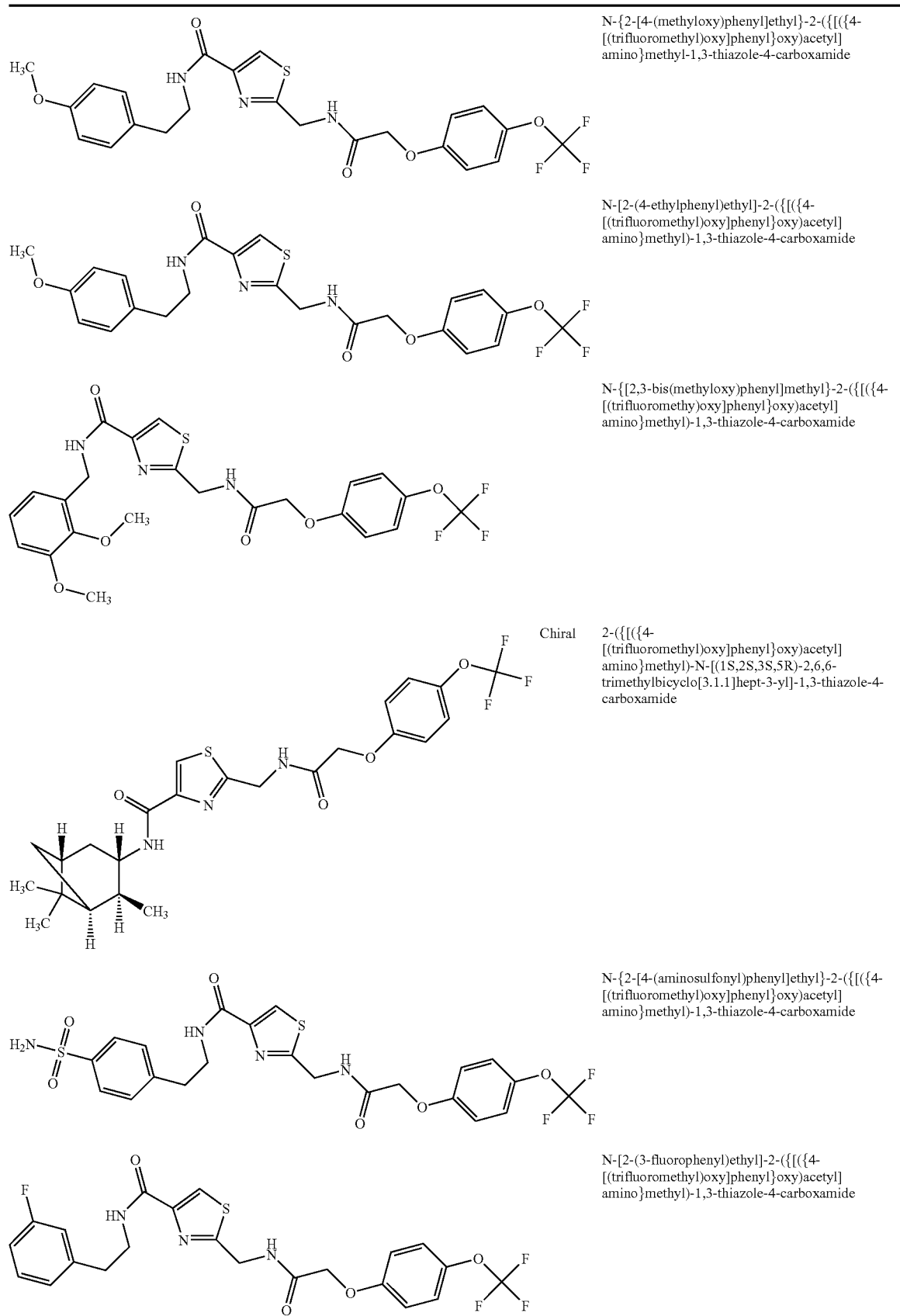

N-{2-[4-(methyloxy)phenyl]ethyl}-2-({[({4-[(trifluoromethyl)oxy]phenyl}oxy)acetyl]amino}methyl-1,3-thiazole-4-carboxamide N-[2-(4-ethylphenyl)ethyl]-2-({[({4-[(trifluoromethyl)oxy]phenyl}oxy)acetyl]amino}methyl)-1,3-thiazole-4-carboxamide N-{[2,3-bis(methyloxy)phenyl]methyl}-2-({[({4-[(trifluoromethy)oxy]phenyl}oxy)acetyl]amino}methyl)-1,3-thiazole-4-carboxamide Chiral 2-({[({4-[(trifluoromethyl)oxy]phenyl}oxy)acetyl]amino}methyl)-N-[(1S,2S,3S,5R)-2,6,6-trimethylbicyclo[3.1.1]hept-3-yl]-1,3-thiazole-4-carboxamide N-{2-[4-(aminosulfonyl)phenyl]ethyl}-2-({[({4-[(trifluoromethyl)oxy]phenyl}oxy)acetyl]amino}methyl)-1,3-thiazole-4-carboxamide N-[2-(3-fluorophenyl)ethyl]-2-({[({4-[(trifluoromethyl)oxy]phenyl}oxy)acetyl]amino}methyl)-1,3-thiazole-4-carboxamide TABLE 3-continued

| 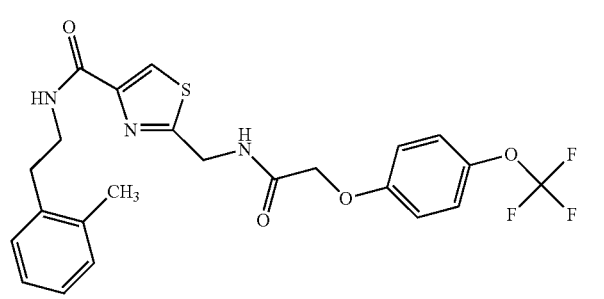 | N-[2-(2-methylphenyl)ethyl]-2-({[({4-[(trifluoromethyl)oxy]phenyl}oxy)acetyl]amino}methyl)-1,3-thiazole-4-carboxamide |
| 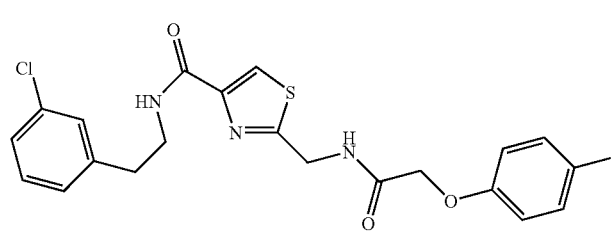 | N-[2-(3-chlorophenyl)ethyl]-2-[({[(4-iodophenyl)oxy]acetyl}amino)methyl]-1,3-thiazole-4-carboxamide |
| 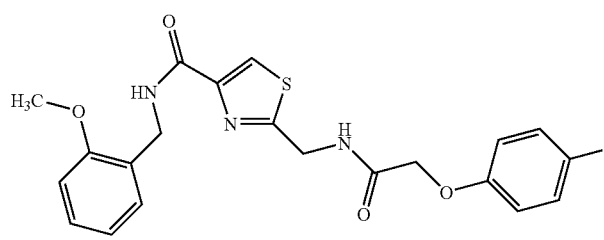 | N-{[2-(methyloxy)phenyl]methyl}-2-({[({4-[(trifluoromethyl)oxy]phenyl}oxy)acetyl]amino}methyl)-1,3-thiazole-4-carboxamide |
| 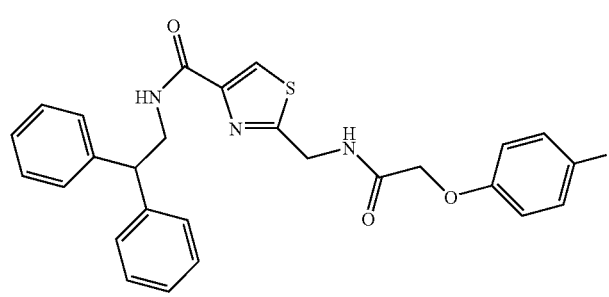 | N-(2,2-diphenylethyl)-2-({[({4-[(trifluoromethy)oxy]phenyl}oxy)acetyl]amino}methyl)-1,3-thiazole-4-carboxamide |
| 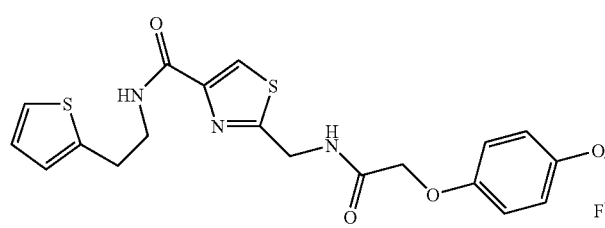 | N-[2-(2-thienyl)ethyl-2-({[({4-[(trifluoromethyl)oxy]phenyl}oxy)acetyl]amino}methy)-1,3-thiazole-4-carboxamide |
| 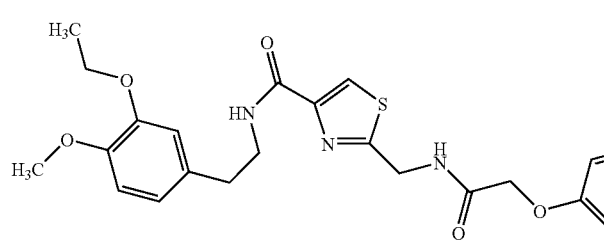 | N-{2-[3-(ethyloxy)-4-(methyloxy)phenyl]ethyl}-2-({[({4-[(trifluoromethyl)oxy]phenyl}oxy)acetyl]amino}methyl)-1,3-thiazole-4-carboxamide |

TABLE 3-continued

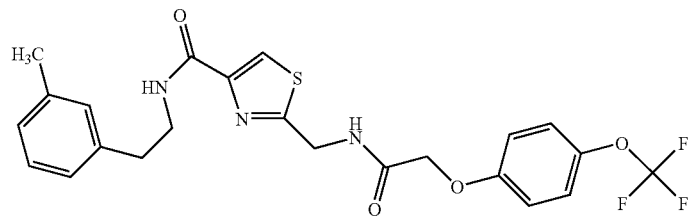

N-[2-(3-methylphenyl)ethyl]-2-({[({4-[(trifluoromethyl)oxy]phenyl}oxy)acetyl]amino}methyl)-1,3-thiazole-4-carboxamide

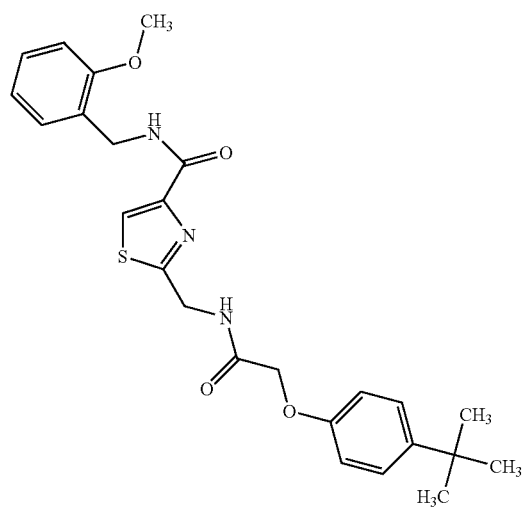

2-{[({[4-(1,1-dimethylethyl)phenyl]oxy}acetyl)amino]methyl}-N-{[2-(methyloxy)phenyl]methyl}-1,3-thiazole-4-carboxamide

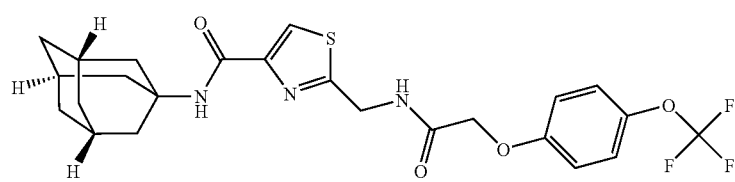

N-tricyclo[3.3.1.1~3,7]dec-1-yl-2-({[({4-[(trifluoromethyl)oxy]phenyl}oxy)acetyl]amino}methyl)-1,3-thiazole-4-carboxamide

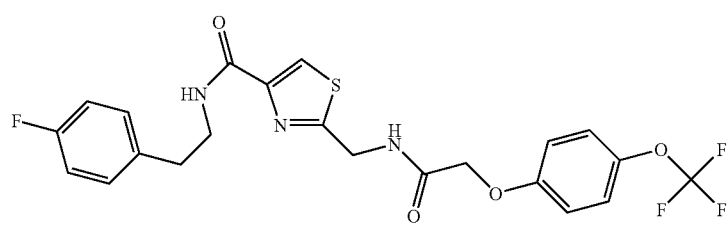

N-[2-(4-fluorophenyl)ethyl]-2-({[({4-[(trifluoromethyl)oxy]phenyl}oxy)acetyl]amino}methyl-1,3-thiazole-4-carboxamide

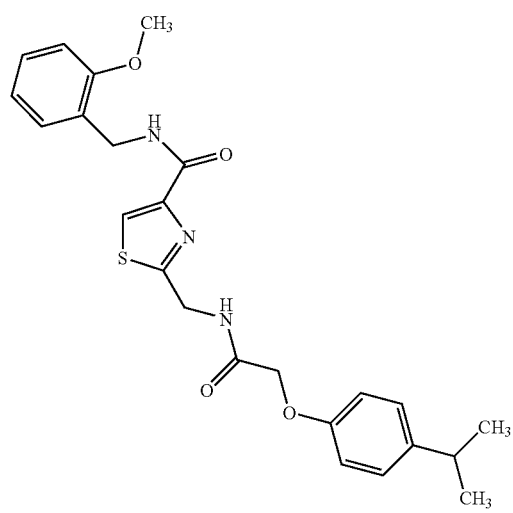

2-{[({[4-(1-methylethyl)phenyl]oxy}acetyl)amino]methyl}-N-{[2-(methyloxy)phenyl]methyl}-1,3-thiazole-4-carboxamide TABLE 3-continued
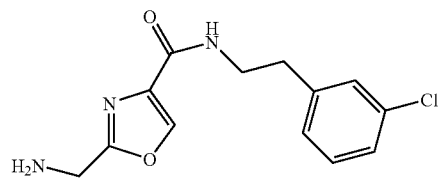
2-(aminomethyl)-N-[2-(3-chlorophenyl)ethyl]-1,3-oxazole-4-carboxamide
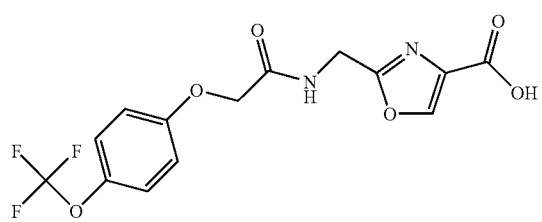
2-({[({4-[(trifluoromethyl)oxy]phenyl}oxy)acetyl]amino}methyl 1,3-oxazole-4-carboxylic acid
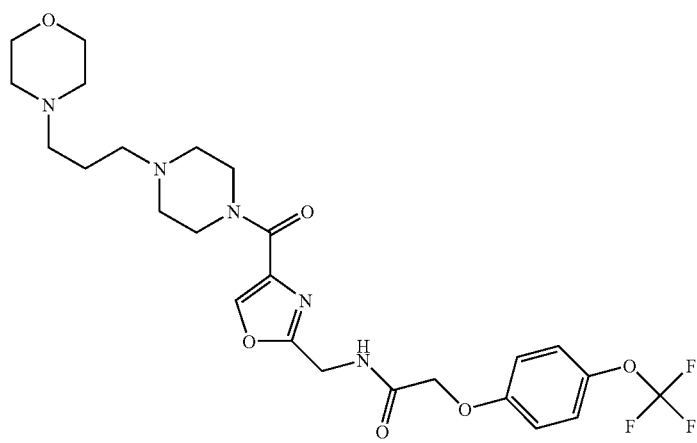
N-[(4-{[4-(3-morpholin-4-ylpropyl)piperazin-1-yl]carbonyl}-1,3-oxazol-2-yl)methyl]-2-({4-[(trifluoromethyl)oxy]phenyl}oxy)acetamide
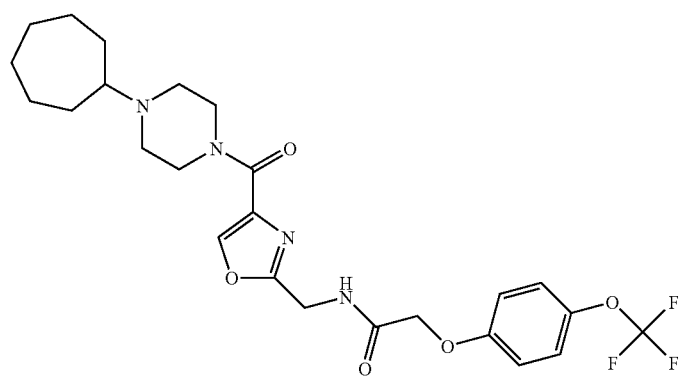
N-({4-[(4-cycloheptylpiperazin-1-yl)carbonyl]-1,3-oxazol-2-yl}methyl)-2-({4-[(trifluoromethyl)oxy]phenyl}oxy)acetamide

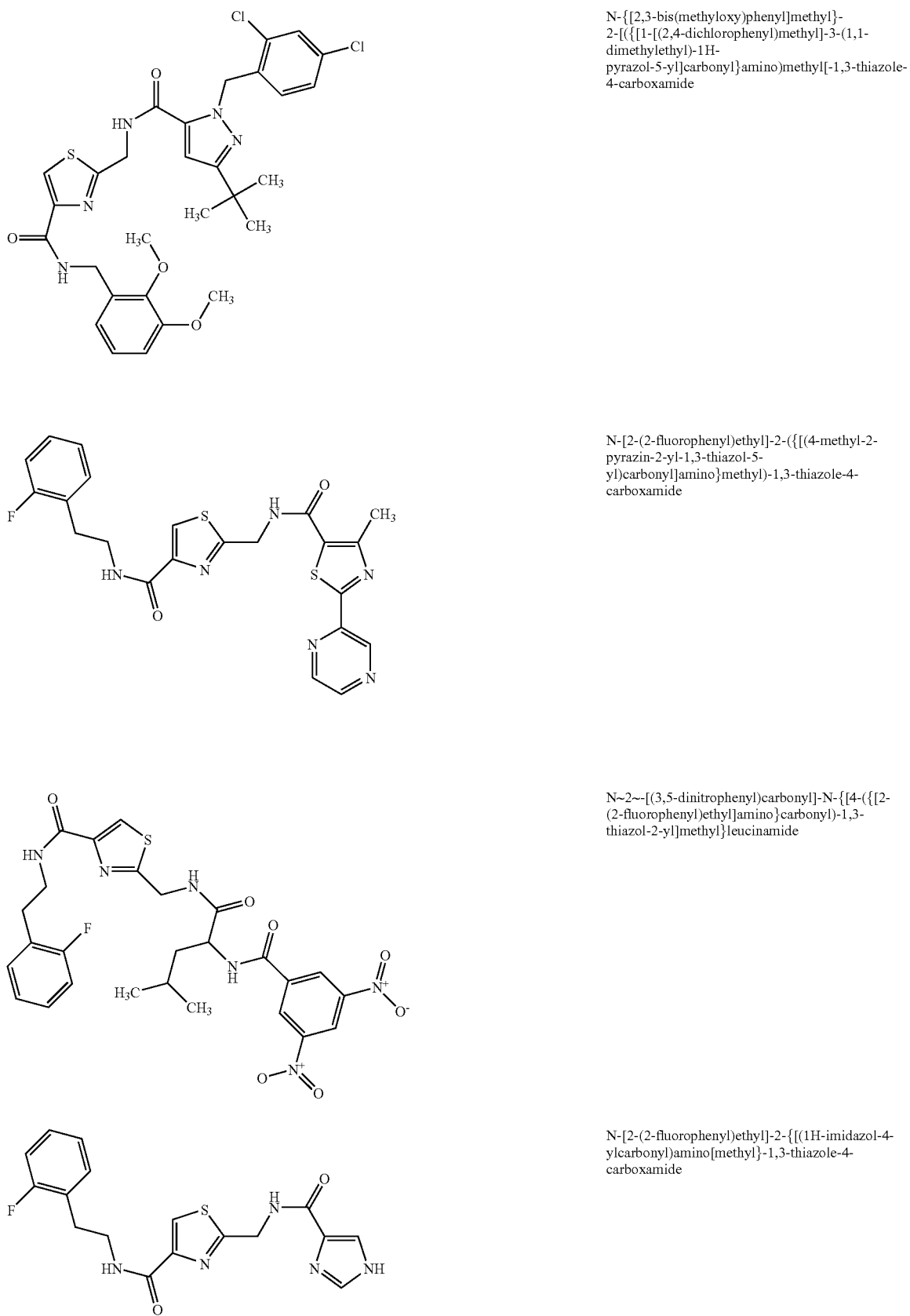

N-{[2,3-bis(methyloxy)phenyl]methyl}-2-[({[1-[(2,4-dichlorophenyl)methyl]-3-(1,1-dimethylethyl)-1H-pyrazol-5-yl]carbonyl}amino)methyl[-1,3-thiazole-4-carboxamide N-[2-(2-fluorophenyl)ethyl]-2-({[(4-methyl-2-pyrazin-2-yl-1,3-thiazol-5-yl)carbonyl]amino}methyl)-1,3-thiazole-4-carboxamide N~2~-[(3,5-dinitrophenyl)carbonyl]-N-{[4-({[2-(2-fluorophenyl)ethyl]amino}carbonyl)-1,3-thiazol-2-yl]methyl}leucinamide N-[2-(2-fluorophenyl)ethyl]-2-{[(1H-imidazol-4-ylcarbonyl)amino[methyl}-1,3-thiazole-4-carboxamide TABLE 3-continued

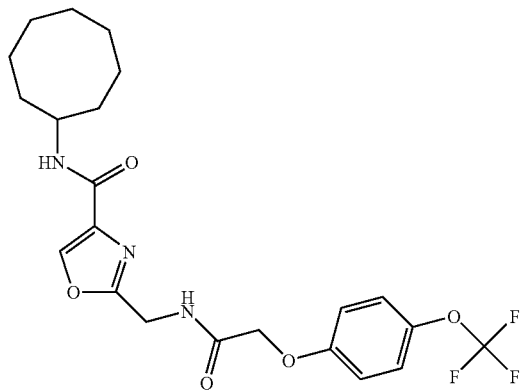

N-cyclooctyl-2-({[({4-[(trifluoromethyl)oxy]phenyl}oxy)acetyl]amino}methyl)-1,3-oxazole-4-carboxamide

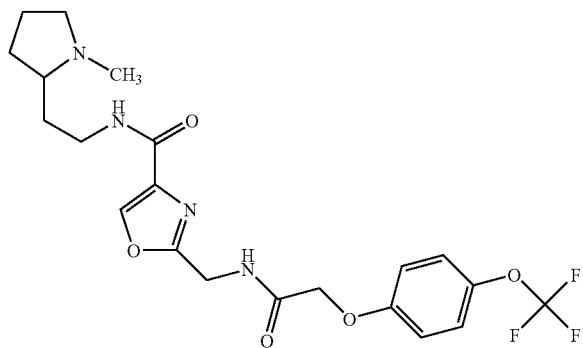

[2-(1-methylpyrrolidin-2-yl)ethyl]-2-({[({4-[(trifluoromethyl)oxy]phenyl}oxy)acetyl]amino}methyl)-1,3-oxazole-4-carboxamide

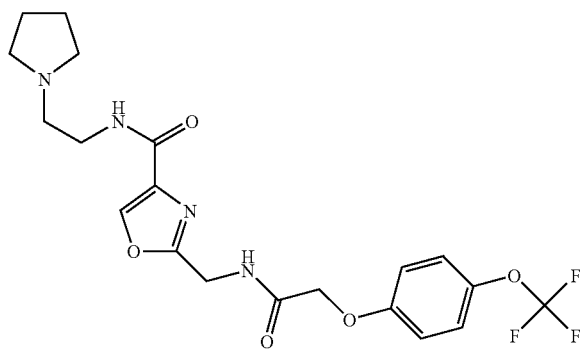

N-(2-pyrrolidin-1-ylethyl)-2-({[({4-[(trifluoromethyl)oxy]phenyl}oxy)acetyl]amino}methyl)-1,3-oxazole-4-carboxamide

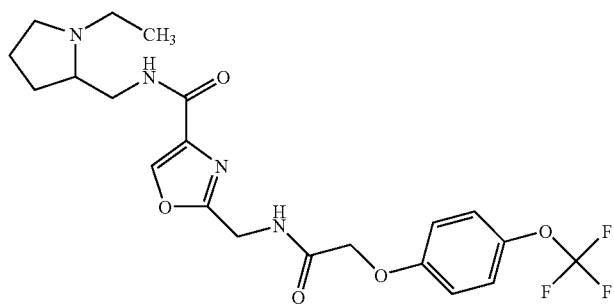

N-[(1-ethylpyrrolidin-2-yl)methyl]-2-({[({4-[(trifluoromethyl)oxy]phenyl}oxy)acetyl]amino}methyl)-1,3-oxazole-4-carboxamide TABLE 3-continued

| Structure | Name |
|---|---|
| (structure) | N-[2-(3-chlorophenyl)ethyl]-2-({[(4-ethylphenyl)sulfonyl]amino}methyl)-1,3-thiazole-4-carboxamide |
| (structure) | N-[2-(3-chlorophenyl)ethyl]-2-({[(pentamethylphenyl)sulfonyl]amino}methyl)-1,3-thiazole-4-carboxamide |
| (structure) | N-[2-(3-chlorophenyl)ethyl]-2-({[(4-ethylphenyl)sulfonyl]amino}methyl)-1,3-thiazole-4-carboxamide |
| (structure) | N-[2-(3-chlorophenyl)ethyl]-2-({[(pentamethylphenyl)sulfonyl]amino}methyl)-1,3-thiazole-4-carboxamide |

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

LENGTHY TABLES

The patent contains a lengthy table section. A copy of the table is available in electronic form from the USPTO web site (http://seqdata.uspto.gov/?pageRequest=docDetail&DocID=US07973061B2). An electronic copy of the table will also be available from the USPTO upon request and payment of the fee set forth in 37 CFR 1.19(b)(3).

What is claimed is:

1. A compound according to Formula I,

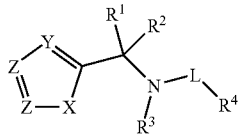

or a pharmaceutically acceptable salt, or hydrate thereof, wherein, each of $R^1$ and $R^2$ is independently selected from —H, halogen, trihalomethyl, —CN, —$NO_2$, —$NH_2$, —$NR^7R^8$, —$S(O)_{0-2}R^7$, —$SO_2NR^7R^7$, —$CO_2R^7$, —$C(O)NR^7R^7$, —$N(R^7)SO_2R^7$, —$N(R^7)C(O)R^7$, —$N(R^7)CO_2R^7$, —$C(O)R^7$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl; or combined, $R^1$ and $R^2$ are oxo;

$R^3$ is selected from —H, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

$R^4$ is —$CH_2$—O-Ph, where Ph is an optionally substituted phenyl;

X is selected from —O—, —$N(R^a)$—, and —$S(O)_{0-2}$—;
Y is =$C(R^b)$— or =N—;
one of Z is =C(C(=O)W)—, while the other Z is =$C(R^c)$— or =N—;
W is —$N(R^5)R^6$;
L is selected from —C(=O)—;
$R^5$ is —H or $R^6$;
$R^6$ is optionally substituted aryl $C_{1-6}$alkyl or optionally substituted heterocyclyl $C_{1-6}$alkyl;
$R^7$ is —H or $R^8$;
$R^8$ is selected from optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$ alkyl;
$R^7$ and $R^8$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P; and
each of $R^a$, $R^b$, and $R^c$ is independently selected from —H, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl.

2. A compound according to claim 1, wherein one of Z is —C(=O)W, while the other Z is =$C(R^c)$—.
3. A compound according to claim 2, wherein X is —$S(O)_{0-2}$— or —O—.
4. A compound according to claim 3, wherein X is —S— or —O—.
5. A compound according to claim 4, wherein Y is =N—.
6. A compound according to claim 5, wherein $R^1$ is —H.
7. A compound according to claim 6, wherein $R^2$ is —H.
8. A compound according to claim 7, wherein $R^3$ is —H.
9. A compound according to claim 5, wherein $R^5$ is —H.
10. A compound according to claim 4, wherein $R^6$ is optionally substituted aryl $C_{1-6}$alkyl.

11. A compound according to claim 4, wherein $R^6$ is optionally substituted heterocyclyl $C_{1-6}$alkyl.
12. A compound according to claim 2, wherein $R^c$ is —H.
13. A compound according to Formula II,

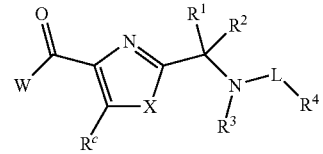

or a pharmaceutically acceptable salt, or hydrate thereof, wherein, each of $R^1$ and $R^2$ is independently selected from —H, halogen, trihalomethyl, —CN, —$NO_2$, —$NH_2$, —$NR^7R^8$, —$S(O)_{0-2}R^7$, —$SO_2NR^7R^7$, —$N(R^7)SO_2R^7$, —$N(R^7)C(O)R^7$, —$N(R^7)CO_2R^7$, —$C(O)R^7$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl; or combined, $R^1$ and $R^2$ are oxo;

$R^3$ is selected from —H, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

$R^4$ is —$CH_2$—O-Ph, where Ph is optionally substituted phenyl;

X is selected from —O—, —$N(R^a)$—, and —$S(O)_{0-2}$—;
W is —$N(R^5)R^6$;
L is selected from —C(=O)—;
$R^5$ is —H or $R^6$;
$R^6$ is optionally substituted aryl $C_{1-6}$alkyl or optionally substituted heterocyclyl $R^7$ is —H or $R^8$;
$R^8$ is selected from optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;
$R^7$ and $R^8$, when taken together with a common nitrogen to which they are attached, form an optionally substituted five- to seven-membered heterocyclyl, said optionally substituted five- to seven-membered heterocyclyl optionally containing at least one additional annular heteroatom selected from N, O, S, and P; and
each of $R^a$ and $R^c$ is independently selected from —H, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl.

14. A compound according to claim 13, wherein X is —$S(O)_{0-2}$- or —O—.
15. A compound according to claim 14, wherein X is —S— or —O—.
16. A compound according to claim 15, wherein $R^1$ is —H.
17. A compound according to claim 16, wherein $R^2$ is —H.
18. A compound according to claim 17, wherein $R^3$ is —H.
19. A compound according to claim 13, wherein $R^5$ is —H.
20. A compound according to claim 13, wherein $R^6$ is optionally substituted $C_{1-6}$alkyl.
21. A compound according to claim 13, wherein $R^6$ is optionally substituted aryl $C_{1-6}$alkyl.
22. A compound according to claim 13, wherein $R^6$ is optionally substituted heterocyclyl $C_{1-6}$alkyl.
23. A compound according to claim 13, wherein $R^c$ is —H.

24. A compound selected from:

---

N-[2-(3-chlorophenyl)ethyl]-2-(1-{[({4-[(trifluoromethyl)oxy]phenyl}oxy)acetyl]amino}ethyl)-1,3-thiazole-4-carboxamide N-[2-(3-chlorophenyl)ethyl]-2-({[({4-[(trifluoromethyl)oxy]phenyl}oxy)acetyl]amino}methyl)-1,3-thiazole-4-carboxamide N-{[4-(1,3-dihydro-2H-isoindol-2-ylcarbonyl)-1,3-thiazol-2-yl]methyl}-2-({4-[(trifluoromethyl)oxy]phenyl}oxy)acetamide N-(10,11-dihydro-5H-dibenzo[a,d]cyclohepten-5-ylmethyl)-2-({[({4-[(trifluoromethyl)oxy]phenyl}oxy)acetyl]amino}methyl)-1,3-thiazole-4-carboxamide N-[2-(2-fluorophenyl)ethyl]-2-({[({4-[(trifluoromethyl)oxy]phenyl}oxy)acetyl]amino}methyl)-1,3-thiazole-4-carboxamide N-[(2R)-2-phenylpropyl]-2-({[({4-[(trifluoromethyl)oxy]phenyl}oxy)acetyl]amino}methyl)-1,3-thiazole-4-carboxamide N-(2-phenylpropyl)-2-({[({4-[(trifluoromethyl)oxy]phenyl}oxy)acetyl]amino}methyl)-1,3-thiazole-4-carboxamide N-[2-(3-chlorophenyl)ethyl]-2-[({[(4-ethylphenyl)amino]carbonyl}amino)methyl]-1,3-thiazole-4-carboxamide N-{2-[4-(methyloxy)phenyl]ethyl}-2-({[({4-[(trifluoromethyl)oxy]phenyl}oxy)acetyl]amino}methyl)-1,3-thiazole-4-carboxamide N-[2-(4-ethylphenyl)ethyl]-2-({[({4-[(trifluoromethyl)oxy]phenyl}oxy)acetyl]amino}methyl)-1,3-thiazole-4-carboxamide N-{[2,3-bis(methyloxy)phenyl]methyl}-2-({[({4-[(trifluoromethyl)oxy]phenyl}oxy)acetyl]amino}methyl)-1,3-thiazole-4-carboxamide 2-({[({4-[(trifluoromethyl)oxy]phenyl}oxy)acetyl]amino}methyl)-N-[(1S,2S,3S,5R)-2,6,6-trimethylbicyclo[3.1.1]hept-3-yl]-1,3-thiazole-4-carboxamide N-{2-[4-(aminosulfonyl)phenyl]ethyl}-2-({[({4-[(trifluoromethyl)oxy]phenyl}oxy)acetyl]amino}methyl)-1,3-thiazole-4-carboxamide N-[2-(3-fluorophenyl)ethyl]-2-({[({4-[(trifluoromethyl)oxy]phenyl}oxy)acetyl]amino}methyl)-1,3-thiazole-4-carboxamide N-[2-(2-methylphenyl)ethyl]-2-({[({4-[(trifluoromethyl)oxy]phenyl}oxy)acetyl]amino}methyl)-1,3-thiazole-4-carboxamide N-[2-(3-chlorophenyl)ethyl]-2-[({[(4-iodophenyl)oxy]acetyl}amino)methyl]-1,3-thiazole-4-carboxamide N-{[2-(methyloxy)phenyl]methyl}-2-({[({4-[(trifluoromethyl)oxy]phenyl}oxy)acetyl]amino}methyl)-1,3-thiazole-4-carboxamide N-(2,2-diphenylethyl)-2-({[({4-[(trifluoromethyl)oxy]phenyl}oxy)acetyl]amino}methyl)-1,3-thiazole-4-carboxamide N-[2-(2-thienyl)ethyl]-2-({[({4-[(trifluoromethyl)oxy]phenyl}oxy)acetyl]amino}methyl)-1,3-thiazole-4-carboxamide N-{2-[3-(ethyloxy)-4-(methyloxy)phenyl]ethyl}-2-({[({4-[(trifluoromethyl)oxy]phenyl}oxy)acetyl]amino}methyl)-1,3-thiazole-4-carboxamide N-[2-(3-methylphenyl)ethyl]-2-({[({4-[(trifluoromethyl)oxy]phenyl}oxy)acetyl]amino}methyl)-1,3-thiazole-4-carboxamide 2-{[({[4-(1,1-dimethylethyl)phenyl]oxy}acetyl)amino]methyl}-N-{[2-(methyloxy)phenyl]methyl}-1,3-thiazole-4-carboxamide N-tricyclo[3.3.1.1~3,7~]dec-1-yl-2-({[({4-[(trifluoromethyl)oxy]phenyl}oxy)acetyl]amino}methyl)-1,3-thiazole-4-carboxamide N-[2-(4-fluorophenyl)ethyl]-2-({[({4-[(trifluoromethyl)oxy]phenyl}oxy)acetyl]amino}methyl)-1,3-thiazole-4-carboxamide N-[2-(3-chlorophenyl)ethyl]-2-{[({[4-(1-methylethyl)phenyl]amino}carbonyl)amino]methyl}-1,3-thiazole-4-carboxamide N-[(2S)-2-phenylpropyl]-2-({[({4-[(trifluoromethyl)oxy]phenyl}oxy)acetyl]amino}methyl)-1,3-thiazole-4-carboxamide N-[2-(2-fluorophenyl)ethyl]-2-{[({[4-(1-methylethyl)phenyl]amino}carbonyl)amino]methyl}-1,3-thiazole-4-carboxamide N-{2-[3-(ethyloxy)phenyl]ethyl}-2-({[({4-[(trifluoromethyl)oxy]phenyl}oxy)acetyl]amino}methyl)-1,3-thiazole-4-carboxamide 2-{[({[4-(1-methylethyl)phenyl]amino}carbonyl)amino]methyl}-N-{[2-(methyloxy)phenyl]methyl}-1,3-thiazole-4-carboxamide N-{2-[3,5-bis(methyloxy)phenyl]ethyl}-2-({[({4-[(trifluoromethyl)oxy]phenyl}oxy)acetyl]amino}methyl)-1,3-thiazole-4-carboxamide N-[2-(3-chlorophenyl)ethyl]-2-({[({4-[(trifluoromethyl)oxy]phenyl}oxy)acetyl]amino}methyl)-1,3-oxazole-4-carboxamide N-[(2-chlorophenyl)methyl]-2-({[({4-[(trifluoromethyl)oxy]phenyl}oxy)acetyl]amino}methyl)-1,3-thiazole-4-carboxamide N-[2-(2,5-dimethylphenyl)ethyl]-2-({[({4-[(trifluoromethyl)oxy]phenyl}oxy)acetyl]amino}methyl)-1,3-thiazole-4-carboxamide N-({2-[(difluoromethyl)oxy]phenyl}methyl)-2-({[({4-[(trifluoromethyl)oxy]phenyl}oxy)acetyl]amino}methyl)-1,3-thiazole-4-carboxamide N-(2-cyclohex-1-en-1-ylethyl)-2-({[({4-[(trifluoromethyl)oxy]phenyl}oxy)acetyl]amino}methyl)-1,3-thiazole-4-carboxamide N-[2-(4-methylphenyl)ethyl]-2-({[({4-[(trifluoromethyl)oxy]phenyl}oxy)acetyl]amino}methyl)-1,3-thiazole-4-carboxamide N-[3-(butyloxy)propyl]-2-({[({4-[(trifluoromethyl)oxy]phenyl}oxy)acetyl]amino}methyl)-1,3-thiazole-4-carboxamide N-(10,11-dihydro-5H-dibenzo[a,d]cyclohepten-5-ylmethyl)-2-({[({4-[(trifluoromethyl)oxy]phenyl}oxy)acetyl]amino}methyl)-1,3-oxazole-4-carboxamide N-[(5-chloro-2-methylphenyl)methyl]-2-({[({4-[(trifluoromethyl)oxy]phenyl}oxy)acetyl]amino}methyl)-1,3-thiazole-4-carboxamide N-{2-[3-(methyloxy)phenyl]ethyl}-2-({[({4-
[(trifluoromethyl)oxy]phenyl}oxy)acetyl]amino}methyl)-1,3-thiazole-4-carboxamide
N-{[2-(methylthio)phenyl]methyl}-2-({[({4-
[(trifluoromethyl)oxy]phenyl}oxy)acetyl]amino}methyl)-1,3-thiazole-4-carboxamide
N-{2-[3,4-bis(methyloxy)phenyl]ethyl}-2-({[({4-
[(trifluoromethyl)oxy]phenyl}oxy)acetyl]amino}methyl)-1,3-thiazole-4-carboxamide
N-{2-[4-(ethyloxy)-3-(methyloxy)phenyl]ethyl}-2-({[({4-
[(trifluoromethyl)oxy]phenyl}oxy)acetyl]amino}methyl)-1,3-thiazole-4-carboxamide
N-[2-(3,4-dichlorophenyl)ethyl]-2-({[({4-
[(trifluoromethyl)oxy]phenyl}oxy)acetyl]amino}methyl)-1,3-thiazole-4-carboxamide
N-[2-(1H-indol-3-yl)ethyl]-2-({[({4-[(trifluoromethyl)oxy]phenyl}oxy)acetyl]amino}methyl)-
1,3-thiazole-4-carboxamide
N-[(2,3-dimethylphenyl)methyl]-2-({[({4-
[(trifluoromethyl)oxy]phenyl}oxy)acetyl]amino}methyl)-1,3-thiazole-4-carboxamide
N-[(5-fluoro-2-methylphenyl)methyl]-2-({[({4-
[(trifluoromethyl)oxy]phenyl}oxy)acetyl]amino}methyl)-1,3-thiazole-4-carboxamide
N-(2-pyridin-4-ylethyl)-2-({[({4-[(trifluoromethyl)oxy]phenyl}oxy)acetyl]amino}methyl)-1,3-
thiazole-4-carboxamide
N-[2-(2,4-dimethylphenyl)ethyl]-2-({[({4-
[(trifluoromethyl)oxy]phenyl}oxy)acetyl]amino}methyl)-1,3-thiazole-4-carboxamide
N-[2-(3-chlorophenyl)ethyl]-2-[({[4-(1-methylethyl)phenyl]acetyl}amino)methyl]-1,3-
thiazole-4-carboxamide
N-(2-pyridin-3-ylethyl)-2-({[({4-[(trifluoromethyl)oxy]phenyl}oxy)acetyl]amino}methyl)-1,3-
thiazole-4-carboxamide
2-({[({4-[(trifluoromethyl)oxy]phenyl}oxy)acetyl]amino}methyl)-N-{2-[3-
(trifluoromethyl)phenyl]ethyl}-1,3-thiazole-4-carboxamide
N-{2-[2,3-bis(methyloxy)phenyl]ethyl}-2-({[({4-
[(trifluoromethyl)oxy]phenyl}oxy)acetyl]amino}methyl)-1,3-thiazole-4-carboxamide
N-(2-amino-2-oxo-1-phenylethyl)-2-({[({4-
[(trifluoromethyl)oxy]phenyl}oxy)acetyl]amino}methyl)-1,3-thiazole-4-carboxamide
N-[2-(2-fluorophenyl)ethyl]-2-{[({[4-(1-methylethyl)phenyl]oxy}acetyl)amino]methyl}-1,3-
thiazole-4-carboxamide
N-[2-(3,4-dimethylphenyl)ethyl]-2-({[({4-
[(trifluoromethyl)oxy]phenyl}oxy)acetyl]amino}methyl)-1,3-thiazole-4-carboxamide
N-({2-[(trifluoromethyl)oxy]phenyl}methyl)-2-({[({4-
[(trifluoromethyl)oxy]phenyl}oxy)acetyl]amino}methyl)-1,3-thiazole-4-carboxamide
N-{[2-(ethyloxy)phenyl]methyl}-2-({[({4-
[(trifluoromethyl)oxy]phenyl}oxy)acetyl]amino}methyl)-1,3-thiazole-4-carboxamide
N-[2-(2-fluorophenyl)ethyl]-2-[({[({4-iodophenyl)oxy]acetyl}amino)methyl]-1,3-thiazole-4-
carboxamide
N-{2-[2-(ethyloxy)phenyl]ethyl}-2-({[({4-
[(trifluoromethyl)oxy]phenyl}oxy)acetyl]amino}methyl)-1,3-thiazole-4-carboxamide
N-[(2,5-difluorophenyl)methyl]-2-({[({4-
[(trifluoromethyl)oxy]phenyl}oxy)acetyl]amino}methyl)-1,3-thiazole-4-carboxamide
N-{[4-({[2-(3-chlorophenyl)ethyl]amino}carbonyl)-1,3-thiazol-2-yl]methyl}-2-[(4-
chlorophenyl)oxy]pyridine-3-carboxamide
2-({[({4-[(trifluoromethyl)oxy]phenyl}oxy)acetyl]amino}methyl)-N-{[2-
(trifluoromethyl)phenyl]methyl}-1,3-thiazole-4-carboxamide
N-[(2,4-dichlorophenyl)methyl]-2-({[({4-
[(trifluoromethyl)oxy]phenyl}oxy)acetyl]amino}methyl)-1,3-thiazole-4-carboxamide
N-(1-phenylpropyl)-2-({[({4-[(trifluoromethyl)oxy]phenyl}oxy)acetyl]amino}methyl)-1,3-
thiazole-4-carboxamide
N-[(4-{[4-(3,5-dichloropyridin-4-yl)piperazin-1-yl]carbonyl}-1,3-thiazol-2-yl)methyl]-2-({4-
[(trifluoromethyl)oxy]phenyl}oxy)acetamide
N-[2-(3-chlorophenyl)ethyl]-2-{[({[4-(1,1-dimethylethyl)phenyl]oxy}acetyl)amino]methyl}-
1,3-thiazole-4-carboxamide
N-{2-[4-(ethyloxy)phenyl]ethyl}-2-({[({4-
[(trifluoromethyl)oxy]phenyl}oxy)acetyl]amino}methyl)-1,3-thiazole-4-carboxamide
N-[(3,5-dichlorophenyl)methyl]-2-({[({4-
[(trifluoromethyl)oxy]phenyl}oxy)acetyl]amino}methyl)-1,3-thiazole-4-carboxamide
Nalpha-{[2-({[({4-[(trifluoromethyl)oxy]phenyl}oxy)acetyl]amino}methyl)-1,3-thiazol-4-
yl]carbonyl}-D-phenylalaninamide
N-{2-[(furan-2-ylmethyl)thio]ethyl}-2-({[({4-
[(trifluoromethyl)oxy]phenyl}oxy)acetyl]amino}methyl)-1,3-thiazole-4-carboxamide
N-[2-(3-chlorophenyl)ethyl]-2-{[({[4-(1-methylethyl)phenyl]oxy}acetyl)amino]methyl}-1,3-
thiazole-4-carboxamide
N-{[4-chloro-3-(trifluoromethyl)phenyl]methyl}-2-({[({4-
[(trifluoromethyl)oxy]phenyl}oxy)acetyl]amino}methyl)-1,3-thiazole-4-carboxamide
N-[3-(propyloxy)propyl]-2-({[({4-[(trifluoromethyl)oxy]phenyl}oxy)acetyl]amino}methyl)-1,3-
thiazole-4-carboxamide
N-[(3,4-dichlorophenyl)methyl]-2-({[({4-
[(trifluoromethyl)oxy]phenyl}oxy)acetyl]amino}methyl)-1,3-thiazole-4-carboxamide
N-cyclooctyl-2-({[({4-[(trifluoromethyl)oxy]phenyl}oxy)acetyl]amino}methyl)-1,3-thiazole-4-
carboxamide
N-(2-pyridin-2-ylethyl)-2-({[({4-[(trifluoromethyl)oxy]phenyl}oxy)acetyl]amino}methyl)-1,3-
thiazole-4-carboxamide
N-{[2,3-bis(methyloxy)phenyl]methyl}-2-{[({[4-(1-
methylethyl)phenyl]amino}carbonyl)amino]methyl}-1,3-thiazole-4-carboxamide
N-[(1S)-1,2,3,4-tetrahydronaphthalen-1-yl]-2-({[({4-
[(trifluoromethyl)oxy]phenyl}oxy)acetyl]amino}methyl)-1,3-thiazole-4-carboxamide N-{2-[2-(methyloxy)phenyl]ethyl}-2-({[({4-[(trifluoromethyl)oxy]phenyl}oxy)acetyl]amino}methyl)-1,3-thiazole-4-carboxamide
N-(2-{[4-(methyloxy)phenyl]oxy}ethyl)-2-({[({4-[(trifluoromethyl)oxy]phenyl}oxy)acetyl]amino}methyl)-1,3-thiazole-4-carboxamide
2-[({[(4-iodophenyl)oxy]acetyl}amino)methyl]-N-{[2-(methyloxy)phenyl]methyl}-1,3-thiazole-4-carboxamide
N-[2-(4-chlorophenyl)ethyl]-2-({[({4-[(trifluoromethyl)oxy]phenyl}oxy)acetyl]amino}methyl)-1,3-thiazole-4-carboxamide
N-[1-(phenylmethyl)piperidin-4-yl]-2-({[({4-[(trifluoromethyl)oxy]phenyl}oxy)acetyl]amino}methyl)-1,3-thiazole-4-carboxamide
N-(1-naphthalen-1-ylethyl)-2-({[({4-[(trifluoromethyl)oxy]phenyl}oxy)acetyl]amino}methyl)-1,3-thiazole-4-carboxamide
N-[1-(4-fluorophenyl)ethyl]-2-({[({4-[(trifluoromethyl)oxy]phenyl}oxy)acetyl]amino}methyl)-1,3-thiazole-4-carboxamide
N-(2-methylcyclohexyl)-2-({[({4-[(trifluoromethyl)oxy]phenyl}oxy)acetyl]amino}methyl)-1,3-thiazole-4-carboxamide
2-({[({4-[(trifluoromethyl)oxy]phenyl}oxy)acetyl]amino}methyl)-N-[(1R,2R,3R,5S)-2,6,6-trimethylbicyclo[3.1.1]hept-3-yl]-1,3-thiazole-4-carboxamide
2-({[({4-[(trifluoromethyl)oxy]phenyl}oxy)acetyl]amino}methyl)-N-[(1S,2S,3S,5R)-2,6,6-trimethylbicyclo[3.1.1]hept-3-yl]-1,3-oxazole-4-carboxamide
N-[2-(4-bromophenyl)ethyl]-2-({[({4-[(trifluoromethyl)oxy]phenyl}oxy)acetyl]amino}methyl)-1,3-thiazole-4-carboxamide
N-[(1S)-2-oxo-1-(phenylmethyl)-2-pyrrolidin-1-ylethyl]-2-({[({4-[(trifluoromethl)oxy]phenyl}oxy)acetyl]amino}methyl-1,3-thiazole-4-carboxamide
N-{2-[4-(aminosulfonyl)phenyl]ethyl}-2-({[({4-[(trifluoromethyl)oxy]phenyl}oxy)acetyl]amino}methyl)-1,3-oxazole-4-carboxamide
N-(2-{[(2,6-dichlorophenyl)methyl]thio}ethyl)-2-({[({4-[(trifluoromethyl)oxy]phenyl}oxy)acetyl]amino}methyl)-1,3-thiazole-4-carboxamide
N-(2-methylpropyl)-2-({[({4-[(trifluoromethyl)oxy]phenyl}oxy)acetyl]amino}methyl)-1,3-thiazole-4-carboxamide
N-[(1S)-1-cyclohexylethyl]-2-({[({4-[(trifluoromethyl)oxy]phenyl}oxy)acetyl]amino}methyl)-1,3-thiazole-4-carboxamide
N-{[4-(1,3,4,9-tetrahydro-2H-beta-carbolin-2-ylcarbonyl)-1,3-thiazol-2-yl]methyl}-2-({4-[(trifluoromethyl)oxy]phenyl}oxy)acetamide
N-{[2-chloro-5-(trifluoromethyl)phenyl]methyl}-2-({[({4-[(trifluoromethyl)oxy]phenyl}oxy)acetyl]amino}methyl)-1,3-thiazole-4-carboxamide
N-[(2-methylphenyl)methyl]-2-({[({4-[(trifluoromethyl)oxy]phenyl}oxy)acetyl]amino}methyl)-1,3-thiazole-4-carboxamide
N-(1-naphthalen-1-ylethyl)-2-({[({4-[(trifluoromethyl)oxy]phenyl}oxy)acetyl]amino}methyl)-1,3-oxazole-4-carboxamide
N-{3-[(2-ethylhexyl)oxy]propyl}-2-({[({4-[(trifluoromethyl)oxy]phenyl}oxy)acetyl]amino}methyl)-1,3-thiazole-4-carboxamide
2-[({[(4-ethylphenyl)amino]carbonyl}amino)methyl]-N-[2-(2-fluorophenyl)ethyl]-1,3-thiazole-4-carboxamide
2-({[({4-[(trifluoromethyl)oxy]phenyl}oxy)acetyl]amino}methyl)-N-[(1S)-1,2,2-trimethylpropyl]-1,3-thiazole-4-carboxamide
N-{(1S,2S)-2-[(phenylmethyl)oxy]cyclopentyl}-2-({[({4-[(trifluoromethyl)oxy]phenyl}oxy)acetyl]amino}methyl)-1,3-thiazole-4-carboxamide
N-[2-(2-chlorophenyl)ethyl]-2-({[({4-[(trifluoromethyl)oxy]phenyl}oxy)acetyl]amino}methyl)-1,3-thiazole-4-carboxamide
N-[(1R,2R,4S)-bicyolo[2.2.1]hept-2-yl]-2-({[({4-[(trifluoromethyl)oxy]phenyl}oxy)acetyl]amino}methyl)-1,3-thiazole-4-carboxamide
N-{[2,6-bis(methyloxy)phenyl]methyl}-2-({[({4-[(trifluoromethyl)oxy]phenyl}oxy)acetyl]amino}methyl)-1,3-thiazole-4-carboxamide
N-{3-[methyl(phenyl)amino]propyl}-2-({[({4-[(trifluoromethyl)oxy]phenyl}oxy)acetyl]amino}methyl)-1,3-thiazole-4-carboxamide
N-(1-phenylethyl)-2-({[({4-[(trifluoromethyl)oxy]phenyl}oxy)acetyl]amino}methyl)-1,3-thiazole-4-carboxamide
2-[({[(4-bromophenyl)oxy]acetyl}amino)methyl]-N-[2-(3-chlorophenly)ethyl]-1,3-thiazole-4-carboxamide
2-[({[(4-ethylphenyl)amino]carbonyl}amino)methyl]-N-{[2-(methyloxy)phenly]methyl}-1,3-thiazole-4-carboxamide
N-[2-(3-chlorophenyl)ethyl]-2-[({[(4-ethylphenyl)oxy]acetyl}amino)methyl]-1,3-thiazole-4-carboxamide
N-{[2,5-bis(methyloxy)phenyl]methyl}-2-({[({4-[(trifluoromethyl)oxy]phenyl}oxy)acetyl]amino}methyl)-1,3-thiazole-4-carboxamide
N-hexyl-2-({[({4-[(trifluoromethyl)oxy]phenyl}oxy)acetyl]amino}methyl)-1,3-thiazole-4-carboxamide
N-[2-(2-fluorophenyl)ethyl]-2-[({[4-(1-methylethyl)phenyl]acetyl}amino)methyl]-1,3-thiazole-4-carboxamide
N-[(2,6-difluorophenyl)methyl]-2-({[({4-[(trifluoromethyl)oxy]phenyl}oxy)acetyl]amino}methyl)-1,3-thiazole-4-carboxamide
N-[(2,3-difluorophenyl)methyl]-2-({[({4-[(trifluoromethyl)oxy]phenyl}oxy)acetyl]amino}methyl)-1,3-thiazole-4-carboxamide
N-[2-(3-chlorophenyl)ethyl]-2-{[(naphthalen-2-ylacetyl)amino]methyl}-1,3-thiazole-4-carboxamide
2-{[({[4-(1-methylethyl)phenyl]oxy}acetyl)amino]methyl}-N-{[2-(methyloxy)phenyl]methyl}-1,3-thiazole-4-carboxamide
N-[(3-chlorophenyl)methyl]-2-({[({4-[(trifluoromethyl)oxy]phenyl}oxy)acetyl]amino}methyl)-1,3-thiazole-4-carboxamide -continued N-{[2,4-bis(methyloxy)phenyl]methyl}-2-({[({4-[(trifluoromethyl)oxy]phenyl}oxy)acetyl]amino}methyl)-1,3-thiazole-4-carboxamide
N-{[3,5-bis(methyloxy)phenyl]methyl}-2-({[({4-[(trifluoromethyl)oxy]phenyl}oxy)acetyl]amino}methyl)-1,3-thiazole-4-carboxamide
N-[2-(phenyloxy)ethyl]-2-({[({4-[(trifluoromethyl)oxy]phenyl}oxy)acetyl]amino}methyl)-1,3-thiazole-4-carboxamide
1,1-dimethylethyl [5-({[2-({[({4-[(trifluoromethyl)oxy]phenyl}oxy)acetyl]amino}methyl)-1,3-thiazol-4-yl]carbonyl}amino)pentyl]carbamate
N-{2-[ethyl(3-methylphenyl)amino]ethyl}-2-({[({4-[(trifluoromethyl)oxy]phenyl}oxy)acetyl]amino}methyl)-1,3-thiazole-4-carboxamide
N-{[2,3-bis(methyloxy)phenyl]methyl}-2-{[({[4-(1-methylethyl)phenyl]oxy}acetyl)amino]methyl}-1,3-thiazole-4-carboxamide
N-[(3,5-difluorophenyl)methyl]-2-({[({4-[(trifluoromethyl)oxy]phenyl}oxy)acetyl]amino}methyl)-1,3-thiazole-4-carboxamide
N-[(3-fluorophenyl)methyl]-2-({[({4-[(trifluoromethyl)oxy]phenyl}oxy)acetyl]amino}methyl)-1,3-thiazole-4-carboxamide
N-[(2R)-2-phenylpropyl]-2-({[({4-[(trifluoromethyl)oxy]phenyl}oxy)acetyl]amino}methyl)-1,3-oxazole-4-carboxamide
2-[(4-chlorophenyl)oxy]-N-{[4-({[2-(2-fluorophenyl)ethyl]amino}carbonyl)-1,3-thiazol-2-yl]methyl}pyridine-3-carboxamide
N-{2-[({5-[(dimethylamino)methyl]furan-2-yl}methyl)thio]ethyl}-2-({[({4-[(trifluoromethyl)oxy]phenyl}oxy)acetyl]amino}methyl)-1,3-thiazole-4-carboxamide
N-[2-(3-chlorophenyl)ethyl]-2-(2-phenyl-1-{[({4-[(trifluoromethyl)oxy]phenyl}oxy)acetyl]amino}ethyl)-1,3-thiazole-4-carboxamide
N-(2-ethylbutyl)-2-({[({4-[(trifluoromethyl)oxy]phenyl}oxy)acetyl]amino}methyl)-1,3-thiazole-4-carboxamide
N-[(3-methyl-2-thienyl)methyl]-2-({[({4-[(trifluoromethyl)oxy]phenyl}oxy)acetyl]amino}methyl)-1,3-thiazole-4-carboxamide
N-{[2,3-bis(methyloxy)phenyl]methyl}-2-[({[(4-ethylphenyl)amino]carbonyl}amino)methyl]-1,3-thiazole-4-carboxamide
N-[(5-methyl-3-phenylisoxazol-4-yl)methyl]-2-({[({4-[(trifluoromethyl)oxy]phenyl}oxy)acetyl]amino}methyl)-1,3-thiazole-4-carboxamide
N-[2-(3-chlorophenyl)ethyl]-2-[({N-[(4-nitrophenyl)carbonyl]glycyl}amino)methyl]-1,3-thiazole-4-carboxamide
N-{2-[2,5-bis(methyloxy)phenyl]ethyl}-2-({[({4-[(trifluoromethyl)oxy]phenyl}oxy)acetyl]amino}methyl)-1,3-thiazole-4-carboxamide
N-(3-methylbutyl)-2-({[({4-[(trifluoromethyl)oxy]phenyl}oxy)acetyl]amino}methyl)-1,3-thiazole-4-carboxamide
N-{[4-(3,4-dihydroisoquinolin-2(1H)-ylcarbonyl)-1,3-thiazol-2-yl]methyl}-2-({4-[(trifluoromethyl)oxy]phenyl}oxy)acetamide
N-(4-methylcyclohexyl)-2-({[({4-[(trifluoromethyl)oxy]phenyl}oxy)acetyl]amino}methyl)-1,3-thiazole-4-carboxamide
N-{[4-({[2-(3-chlorophenyl)ethyl]amino}carbonyl)-1,3-thiazol-2-yl]methyl}-2-[(4-fluorophenyl)oxy]pyridine-3-carboxamide
2-hydroxy-4-({[2-({[({4-[(trifluoromethyl)oxy]phenyl}oxy)acetyl]amino}methyl)-1,3-thiazol-4-yl]carbonyl}amino)benzoic acid
N-[2-(2-fluorophenyl)ethyl]-2-({[({4-[(trifluoromethyl)oxy]phenyl}oxy)acetyl]amino}methyl)-1,3-oxazole-4-carboxamide
N-({4-[({[2,3-bis(methyloxy)phenyl]methyl}amino)carbonyl]-1,3-thiazol-2-yl}methyl)-2-[(4-chlorophenyl)oxy]pyridine-3-carboxamide
N-(2-phenylethyl)-2-({[({4-[(trifluoromethyl)oxy]phenyl}oxy)acetyl]amino}methyl)-1,3-thiazole-4-carboxamide
N-[2-(ethylthio)ethyl]-2-({[({4-[(trifluoromethyl)oxy]phenyl}oxy)acetyl]amino}methyl)-1,3-thiazole-4-carboxamide
N-(1,1-diethylprop-2-yn-1-yl)-2-({[({4-[(trifluoromethyl)oxy]phenyl}oxy)acetyl]amino}methyl)-1,3-thiazole-4-carboxamide
N-[2-(3-fluorophenyl)ethyl]-2-({[({4-[(trifluoromethyl)oxy]phenyl}oxy)acetyl]amino}methyl)-1,3-oxazole-4-carboxamide
N-[3-(methylthio)propyl]-2-({[({4-[(trifluoromethyl)oxy]phenyl}oxy)acetyl]amino}methyl)-1,3-thiazole-4-carboxamide
N-[(4-chloro-2-methylphenyl)methyl]-2-({[({4-[(trifluoromethyl)oxy]phenyl}oxy)acetyl]amino}methyl)-1,3-thiazole-4-carboxamide
N-[2-(3-methylphenyl)ethyl]-2-({[({4-[(trifluoromethyl)oxy]phenyl}oxy)acetyl]amino}methyl)-1,3-oxazole-4-carboxamide
N-(1-methyl-3-phenylpropyl)-2-({[({4-[(trifluoromethyl)oxy]phenyl}oxy)acetyl]amino}methyl)-1,3-thiazole-4-carboxamide
N-[(1S)-1,2-dimethylpropyl]-2-({[({4-[(trifluoromethyl)oxy]phenyl}oxy)acetyl]amino}methyl)-1,3-thiazole-4-carboxamide
N-{[3-(methyloxy)phenyl]methyl}-2-({[({4-[(trifluoromethyl)oxy]phenyl}oxy)acetyl]amino}methyl)-1,3-thiazole-4-carboxamide
N-{2-[3,4-bis(methyloxy)phenyl]ethyl}-2-({[({4-[(trifluoromethyl)oxy]phenyl}oxy)acetyl]amino}methyl)-1,3-oxazole-4-carboxamide
2-({[({4-[(trifluoromethyl)oxy]phenyl}oxy)acetyl]amino}methyl)-N-{[3-(trifluoromethyl)phenyl]methyl}-1,3-thiazole-4-carboxamide
N-[(3-iodophenyl)methyl]-2-({[({4-[(trifluoromethyl)oxy]phenyl}oxy)acetyl]amino}methyl)-1,3-thiazole-4-carboxamide
N-{[2-fluoro-3-(trifluoromethyl)phenyl]methyl}-2-({[({4-[(trifluoromethyl)oxy]phenyl}oxy)acetyl]amino}methyl)-1,3-thiazole-4-carboxamide
N-[2-(2-thienyl)ethyl]-2-({[({4-[(trifluoromethyl)oxy]phenyl}oxy)acetyl]amino}methyl)-1,3-oxazole-4-carboxamide -continued N-[2-(2,4-dichlorophenyl)ethyl]-2-({[({4-[(trifluoromethyl)oxy]phenyl}oxy)acetyl]amino}methyl)-1,3-thiazole-4-carboxamide
N-[2-(3-chlorophenyl)ethyl]-2-[({[(3-chlorophenyl)oxy]acetyl}amino)methyl]-1,3-thiazole-4-carboxamide
N-[(1S)-1-(4-methylphenyl)ethyl]-2-({[({4-[(trifluoromethyl)oxy]phenyl}oxy)acetyl]amino}methyl)-1,3-thiazole-4-carboxamide
N-{[2-chloro-6-(phenyloxy)phenyl]methyl}-2-({[({4-[(trifluoromethyl)oxy]phenyl}oxy)acetyl]amino}methyl)-1,3-thiazole-4-carboxamide
N-(2-thienylmethyl)-2-({[({4-[(trifluoromethyl)oxy]phenyl}oxy)acetyl]amino}methyl)-1,3-thiazole-4-carboxamide
N-[(1R)-1,2,3,4-tetrahydronaphthalen-1-yl]-2-({[({4-[(trifluoromethyl)oxy]phenyl}oxy)acetyl]amino}methyl)-1,3-thiazole-4-carboxamide
N-[(2,4-dichloro-6-methylphenyl)methyl]-2-({[({4-[(trifluoromethyl)oxy]phenyl}oxy)acetyl]amino}methyl)-1,3-thiazole-4-carboxamide
N-(diphenylmethyl)-2-({[({4-[(trifluoromethyl)oxy]phenyl}oxy)acetyl]amino}methyl)-1,3-thiazole-4-carboxamide
N-[2-(3-chlorophenyl)ethyl]-2-[({[({4-methylphenyl)amino]carbonyl}amino)methyl]-1,3-thiazole-4-carboxamide
N-[2-(2-fluorophenyl)ethyl]-2-{[(naphthalen-2-ylacetyl)amino]methyl}-1,3-thiazole-4-carboxamide
N-[(4-methylphenyl)methyl]-2-({[({4-[(trifluoromethyl)oxy]phenyl}oxy)acetyl]amino}methyl)-1,3-thiazole-4-carboxamide
N-(1-ethylpropyl)-2-({[({4-[(trifluoromethyl)oxy]phenyl}oxy)acetyl]amino}methyl)-1,3-thiazole-4-carboxamide
N-(cyclohexylmethyl)-2-({[({4-[(trifluoromethyl)oxy]phenyl}oxy)acetyl]amino}methyl)-1,3-thiazole-4-carboxamide
N-[2-(3-chlorophenyl)ethyl]-2-{[({[4-(methylthio)phenyl]amino}carbonyl)amino]methyl}-1,3-thiazole-4-carboxamide
N-{[4-fluoro-3-(trifluoromethyl)phenyl]methyl}-2-({[({4-[(trifluoromethyl)oxy]phenyl}oxy)acetyl]amino}methyl)-1,3-thiazole-4-carboxamide
N-(3,3-dimethylbutyl)-2-({[({4-[(trifluoromethyl)oxy]phenyl}oxy)acetyl]amino}methyl)-1,3-thiazole-4-carboxamide
N-(2-cyclohex-1-en-1-ylethyl)-2-({[({4-[(trifluoromethyl)oxy]phenyl}oxy)acetyl]amino}methyl)-1,3-oxazole-4-carboxamide
N-butyl-2-({[({4-[(trifluoromethyl)oxy]phenyl}oxy)acetyl]amino}methyl)-1,3-thiazole-4-carboxamide
N-{[4-(methyloxy)phenyl]methyl}-2-({[({4-[(trifluoromethyl)oxy]phenyl}oxy)acetyl]amino}methyl)-1,3-thiazole-4-carboxamide
N-(1-methylhexyl)-2-({[({4-[(trifluoromethyl)oxy]phenyl}oxy)acetyl]amino}methyl)-1,3-thiazole-4-carboxamide
N-(1-ethynylcyclohexyl)-2-({[({4-[(trifluoromethyl)oxy]phenyl}oxy)acetyl]amino}methyl)-1,3-thiazole-4-carboxamide
2-({[({4-[(trifluoromethyl)oxy]phenyl}oxy)acetyl]amino}methyl)-N-{2-[3-(trifluoromethyl)phenyl]ethyl}-1,3-oxazole-4-carboxamide
N-(2,3-dihydro-1H-inden-1-yl)-2-({[({4-[(trifluoromethyl)oxy]phenyl}oxy)acetyl]amino}methyl)-1,3-thiazole-4-carboxamide
N-{(1S)-1-[4-(methyloxy)phenyl]ethyl}-2-({[({4-[(trifluoromethyl)oxy]phenyl}oxy)acetyl]amino}methyl)-1,3-thiazole-4-carboxamide
N-[2-(3-chlorophenyl)ethyl]-2-{[({[4-(ethyloxy)phenyl]amino}carbonyl)amino]methyl}-1,3-thiazole-4-carboxamide
N-[(3,4-difluorophenyl)methyl]-2-({[({4-[(trifluoromethyl)oxy]phenyl}oxy)acetyl]amino}methyl)-1,3-thiazole-4-carboxamide
N-{[2-(methylthio)phenyl]methyl}-2-({[({4-[(trifluoromethyl)oxy]phenyl}oxy)acetyl]amino}methyl)-1,3-oxazole-4-carboxamide
N-{[3,4-bis(methyloxy)phenyl]methyl}-2-({[({4-[(trifluoromethyl)oxy]phenyl}oxy)acetyl]amino}methyl)-1,3-thiazole-4-carboxamide
Nalpha-{[2-({[({4-[(trifluoromethyl)oxy]phenyl}oxy)acetyl]amino}methyl)-1,3-thiazol-4-yl]carbonyl}-L-phenylalaninamide
N-(7-methyloctyl)-2-({[({4-[(trifluoromethyl)oxy]phenyl}oxy)acetyl]amino}methyl)-1,3-thiazole-4-carboxamide
N-(pyridin-2-ylmethyl)-2-({[({4-[(trifluoromethyl)oxy]phenyl}oxy)acetyl]amino}methyl)-1,3-thiazole-4-carboxamide
N-[(3-chloro-4-fluorophenyl)methyl]-2-({[({4-[(trifluoromethyl)oxy]phenyl}oxy)acetyl]amino}methyl)-1,3-thiazole-4-carboxamide
2-[({[4-(1-methylethyl)phenyl]acetyl}amino)methyl]-N-{[2-(methyloxy)phenyl]methyl}1,3-thiazole-4-carboxamide
N-hexyl-N-methyl-2-({[({4-[(trifluoromethyl)oxy]phenyl}oxy)acetyl]amino}methyl)-1,3-thiazole-4-carboxamide
N-(phenylmethyl)-2-({[({4-[(trifluoromethyl)oxy]phenyl}oxy)acetyl]amino}methyl)-1,3-thiazole-4-carboxamide
N-[2-(methylthio)ethyl]-2-({[({4-[(trifluoromethyl)oxy]phenyl}oxy)acetyl]amino}methyl)-1,3-thiazole-4-carboxamide
N-(1,1,3,3-tetramethylbutyl)-2-({[({4-[(trifluoromethyl)oxy]phenyl}oxy)acetyl]amino}methyl)-1,3-thiazole-4-carboxamide
N-(1,2-dimethylpropyl)-2-({[({4-[(trifluoromethyl)oxy]phenyl}oxy)acetyl]amino}methyl)-1,3-thiazole-4-carboxamide
2-[(4-chlorophenyl)oxy]-N-({4-[({[2-(methyloxy)phenyl]methyl}amino)carbonyl]-1,3-thiazol-2-yl}methyl)pyridine-3-carboxamide
N-(1,2,3,4-tetrahydronaphthalen-1-yl)-2-({[({4-[(trifluoromethyl)oxy]phenyl}oxy)acetyl]amino}methyl)-1,3-thiazole-4-carboxamide -continued N-(2-ethylhexyl)-2-({[({4-[(trifluoromethyl)oxy]phenyl}oxy)acetyl]amino}methyl)-1,3-thiazole-4-carboxamide
N-[2-(4-fluorophenyl)ethyl]-2-({[({4-[(trifluoromethyl)oxy]phenyl}oxy)acetyl]amino}methyl)-1,3-oxazole-4-carboxamide
N~2~-{[2-({[({4-[(trifluoromethyl)oxy]phenyl}oxy)acetyl]amino}methyl)-1,3-thiazol-4-yl]carbonyl}-D-leucinamide
N-{[2-(methyloxy)phenyl]methyl}-2-({[({4-[(trifluoromethyl)oxy]phenyl}oxy)acetyl]amino}methyl)-1,3-oxazole-4-carboxamide
N-[1-(4-bromophenyl)ethyl]-2-({[({4-[(trifluoromethyl)oxy]phenyl}oxy)acetyl]amino}methyl)-1,3-thiazole-4-carboxamide
N-(2-morpholin-4-ylethyl)-2-({[({4-[(trifluoromethyl)oxy]phenyl}oxy)acetyl]amino}methyl)-1,3-thiazole-4-carboxamide
N-[(4-fluorophenyl)methyl]-2-({[({4-[(trifluoromethyl)oxy]phenyl}oxy)acetyl]amino}methyl)-1,3-thiazole-4-carboxamide
N-{2-[3,5-bis(methyloxy)phenyl]ethyl}-2-({[({4-[(trifluoromethyl)oxy]phenyl}oxy)acetyl]amino}methyl)-1,3-oxazole-4-carboxamide
N-[2-(3-chlorophenyl)ethyl]-2-({[(3E)-4-phenylbut-3-enoyl]amino}methyl)-1,3-thiazole-4-carboxamide
N-cyclohexyl-2-({[({4-[(trifluoromethyl)oxy]phenyl}oxy)acetyl]amino}methyl)-1,3-thiazole-4-carboxamide
N-(2-methylbutyl)-2-({[({4-[(trifluoromethyl)oxy]phenyl}oxy)acetyl]amino}methyl)-1,3-thiazole-4-carboxamide
N-[2-(3,4-dimethylphenyl)ethyl]-2-({[({4-[(trifluoromethyl)oxy]phenyl}oxy)acetyl]amino}methyl)-1,3-oxazole-4-carboxamide
N-(1,5-dimethylhexyl)-2-({[({4-[(trifluoromethyl)oxy]phenyl}oxy)acetyl]amino}methyl)-1,3-thiazole-4-carboxamide
N-{2-[2-(phenyloxy)phenyl]ethyl}-2-({[({4-[(trifluoromethyl)oxy]phenyl}oxy)acetyl]amino}methyl)-1,3-thiazole-4-carboxamide
2-[[({[4-(butyloxy)phenyl]amino}carbonyl)amino]methyl}-N-{[2-(methyloxy)phenyl]methyl}-1,3-thiazole-4-carboxamide
2-[({[(4-chlorophenyl)oxy]acetyl}amino)methyl]-N-[2-(2-fluorophenyl)ethyl]-1,3-thiazole-4-carboxamide
N-(cyclopropylmethyl)-2-({[({4-[(trifluoromethyl)oxy]phenyl}oxy)acetyl]amino}methyl)-1,3-thiazole-4-carboxamide
N-[2-(3-chlorophenyl)ethyl]-2-{[({[(1R,2S)-2-phenylcyclopropyl]amino}carbonyl)amino]methyl}-1,3-thiazole-4-carboxamide
N-{(1R,2R)-2-[(phenylmethyl)oxy]cyclopentyl}-2-({[({4-[(trifluoromethyl)oxy]phenyl}oxy)acetyl]amino}methyl)-1,3-thiazole-4-carboxamide
N-(2-pyridin-4-ylethyl)-2-({[({4-[(trifluoromethyl)oxy]phenyl}oxy)acetyl]amino}methyl)-1,3-oxazole-4-carboxamide
N-(1-methylheptyl)-2-({[({4-[(trifluoromethyl)oxy]phenyl}oxy)acetyl]amino}methyl)-1,3-thiazole-4-carboxamide
N-{[4-({[2-(3-chlorophenyl)ethyl]amino}carbonyl)-1,3-thiazol-2-yl]methyl}-N~2~-(phenylcarbonyl)methioninamide
N-(1,2-diphenylethyl)-2-({[({4-[(trifluoromethyl)oxy]phenyl}oxy)acetyl]amino}methyl)-1,3-thiazole-4-carboxamide
N-{[2,3-bis(methyloxy)phenyl]methyl}-2-({[({4-[(trifluoromethyl)oxy]phenyl}oxy)acetyl]amino}methyl)-1,3-oxazole-4-carboxamide
N-{2-[4-(methyloxy)phenyl]ethyl}-2-({[({4-[(trifluoromethyl)oxy]phenyl}oxy)acetyl]amino}methyl)-1,3-oxazole-4-carboxamide
N-[2-(4-methylphenyl)ethyl]-2-({[({4-[(trifluoromethyl)oxy]phenyl}oxy)acetyl]amino}methyl)-1,3-oxazole-4-carboxamide
N-(2,2-diphenylethyl)-2-({[({4-[(trifluoromethyl)oxy]phenyl}oxy)acetyl]amino}methyl)-1,3-oxazole-4-carboxamide
N-[(4-chlorophenyl)methyl]-2-({[({4-[(trifluoromethyl)oxy]phenyl}oxy)acetyl]amino}methyl)-1,3-thiazole-4-carboxamide
N-cyclopentyl-2-({[({4-[(trifluoromethyl)oxy]phenyl}oxy)acetyl]amino}methyl)-1,3-thiazole-4-carboxamide
N-{[2-(methyloxy)phenyl]methyl}-2-{[(naphthalen-2-ylacetyl)amino]methyl}-1,3-thiazole-4-carboxamide
N-{2-[3-(ethyloxy)phenyl]ethyl}-2-({[({4-[(trifluoromethyl)oxy]phenyl}oxy)acetyl]amino}methyl)-1,3-oxazole-4-carboxamide
N-[2-(4-bromophenyl)ethyl]-2-({[({4-[(trifluoromethyl)oxy]phenyl}oxy)acetyl]amino}methyl)-1,3-oxazole-4-carboxamide
N-[2-(3-chlorophenyl)ethyl]-2-[({[4-(methylthio)phenyl]acetyl}amino)methyl]-1,3-thiazole-4-carboxamide
2-({[({4-[(trifluoromethyl)oxy]phenyl}oxy)acetyl]amino}methyl)-N-[(1R)-1,2,2-trimethylpropyl]-1,3-thiazole-4-carboxamide
N-{2-[3-(methyloxy)phenyl]ethyl}-2-({[({4-[(trifluoromethyl)oxy]phenyl}oxy)acetyl]amino}methyl)-1,3-oxazole-4-carboxamide
N-{[2-(ethyloxy)phenyl]methyl}-2-({[({4-[(trifluoromethyl)oxy]phenyl}oxy)acetyl]amino}methyl)-1,3-oxazole-4-carboxamide
2-[({[1-(4-chlorophenyl)cyclopropyl]carbonyl}amino)methyl]-N-[2-(3-chlorophenyl)ethyl]-1,3-thiazole-4-carboxamide
N-{[4-(dimethylamino)phenyl]methyl}-2-({[({4-[(trifluoromethyl)oxy]phenyl}oxy)acetyl]amino}methyl)-1,3-thiazole-4-carboxamide
N-(2-cyanoethyl)-N-hexyl-2-({[({4-[(trifluoromethyl)oxy]phenyl}oxy)acetyl]amino}methyl)-1,3-thiazole-4-carboxamide
2-[({[(4-bromophenyl)oxy]acetyl}amino)methyl]-N-[2-(2-fluorophenyl)ethyl]-1,3-thiazole-4-carboxamide N-[(2S)-2-phenylpropyl]-2-({[({4-[(trifluoromethyl)oxy]phenyl}oxy)acetyl]amino}methyl)-1,3-oxazole-4-carboxamide
N-(pyridin-3-ylmethyl)-2-({[({4-[(trifluoromethyl)oxy]phenyl}oxy)acetyl]amino}methyl)-1,3-thiazole-4-carboxamide
N-(2-phenylethyl)-2-({[({4-[(trifluoromethyl)oxy]phenyl}oxy)acetyl]amino}methyl)-1,3-oxazole-4-carboxamide
N-[(4-{[3-methyl-4-(4-methylphenyl)piperazin-1-yl]carbonyl}-1,3-thiazol-2-yl)methyl]-2-({4-[(trifluoromethyl)oxy]phenyl}oxy)acetamide
N-{[4-fluoro-2-(trifluoromethyl)phenyl]methyl}-2-({[({4-[(trifluoromethyl)oxy]phenyl}oxy)acetyl]amino}methyl)-1,3-thiazole-4-carboxamide
N-({4-[(4-propylpiperidin-1-yl)carbonyl]-1,3-thiazol-2-yl}methyl)-2-({4-[(trifluoromethyl)oxy]phenyl}oxy)acetamide
N-[2-(4-chlorophenyl)ethyl]-2-({[({4-[(trifluoromethyl)oxy]phenyl}oxy)acetyl]amino}methyl)-1,3-oxazole-4-carboxamide
N-[2-(1-methylpyrrolidin-2-yl)ethyl]-2-({[({4-[(trifluoromethyl)oxy]phenyl}oxy)acetyl]amino}methyl)-1,3-thiazole-4-carboxamide
N-{[2,3-bis(methyloxy)phenyl]methyl}-2-{[({[4-(butyloxy)phenyl]amino}carbonyl)amino]methyl}-1,3-thiazole-4-carboxamide
N-(furan-2-ylmethyl)-2-({[({4-[(trifluoromethyl)oxy]phenyl}oxy)acetyl]amino}methyl)-1,3-thiazole-4-carboxamide
N-{2-[3-(ethyloxy)-4-(methyloxy)phenyl]ethyl}-2-({[({4-[(trifluoromethyl)oxy]phenyl}oxy)acetyl]amino}methyl)-1,3-oxazole-4-carboxamide
N-[2-(1H-indol-3-yl)ethyl]-2-({[({4-[(trifluoromethyl)oxy]phenyl}oxy)acetyl]amino}methyl)-1,3-oxazole-4-carboxamide
N-{[4-(octahydroquinolin-1(2H)-ylcarbonyl)-1,3-thiazol-2-yl]methyl}-2-({4-[(trifluoromethyl)oxy]phenyl}oxy)acetamide
N-({4-[(3-methyl-4-phenylpiperazin-1-yl)carbonyl]-1,3-thiazol-2-yl}methyl)-2-({4-[(trifluoromethyl)oxy]phenyl}oxy)acetamide
1,1-dimethylethyl (1-{[2-({[({4-[(trifluoromethyl)oxy]phenyl}oxy)acetyl]amino}methyl)-1,3-thiazol-4-yl]carbonyl}piperidin-4-yl)carbamate
N-[(4-{[2R,6S]-2,6-dimethylmorpholin-4-yl]carbonyl}-1,3-thiazol-2-yl)methyl]-2-({4-[(trifluoromethyl)oxy]phenyl}oxy)acetamide
N-{[2,3-bis(methyloxy)phenyl]methyl}-2-{[(naphthalen-2-ylacetyl)amino]methyl}-1,3-thiazole-4-carboxamide
N-(2-methylcyclohexyl)-2-({[({4-[(trifluoromethyl)oxy]phenyl}oxy)acetyl]amino}methyl)-1,3-oxazole-4-carboxamide
N-[(2,4-difluorophenyl)methyl]-2-({[({4-[(trifluoromethyl)oxy]phenyl}oxy)acetyl]amino}methyl)-1,3-thiazole-4-carboxamide
N-(2-phenylpropyl)-2-({[({4-[(trifluoromethyl)oxy]phenyl}oxy)acetyl]amino}methyl)-1,3-oxazole-4-carboxamide
N-(3,3-diphenylpropyl)-2-({[({4-[(trifluoromethyl)oxy]phenyl}oxy)acetyl]amino}methyl)-1,3-thiazole-4-carboxamide
N-[(2-chlorophenyl)methyl]-2-({[({4-[(trifluoromethyl)oxy]phenyl}oxy)acetyl]amino}methyl)-1,3-oxazole-4-carboxamide
N-(1,4-dimethylpentyl)-2-({[({4-[(trifluoromethyl)oxy]phenyl}oxy)acetyl]amino}methyl)-1,3-thiazole-4-carboxamide
2-[({[(4-chlorophenyl)oxy]acetyl}amino)methyl]-N-{[2-(methyloxy)phenyl]methyl}-1,3-thiazole-4-carboxamide
N-[(1S)-1-cyclohexylethyl]-2-({[({4-[(trifluoromethyl)oxy]phenyl}oxy)acetyl]amino}methyl)-1,3-oxazole-4-carboxamide
N-(tetrahydrofuran-2-ylmethyl)-2-({[({4-[(trifluoromethyl)oxy]phenyl}oxy)acetyl]amino}methyl)-1,3-thiazole-4-carboxamide
N-({4-[(4aR,8aS)-octahydroisoquinolin-2(1H)-ylcarbonyl]-1,3-thiazol-2-yl}methyl)-2-({4-[(trifluoromethyl)oxy]phenyl}oxy)acetamide
N-(3-morpholin-4-ylpropyl)-2-({[({4-[(trifluoromethyl)oxy]phenyl}oxy)acetyl]amino}methyl)-1,3-thiazole-4-carboxamide
N-[1-methyl-2-(methyloxy)ethyl]-2-({[({4-[(trifluoromethyl)oxy]phenyl}oxy)acetyl]amino}methyl)-1,3-thiazole-4-carboxamide
N-[3-(methyloxy)propyl]-2-({[({4-[(trifluoromethyl)oxy]phenyl}oxy)acetyl]amino}methyl)-1,3-thiazole-4-carboxamide
N,N-diethyl-1-{[2-({[({4-[(trifluoromethyl)oxy]phenyl}oxy)acetyl]amino}methyl)-1,3-thiazol-4-yl]carbonyl}piperidine-3-carboxamide
N-({4-[(4aS,8aS)-octahydroisoquinolin-2(1H)-ylcarbonyl]-1,3-thiazol-2-yl}methyl)-2-({4-[(trifluoromethyl)oxy]phenyl}oxy)acetamide
1-{[2-({[({4-[(trifluoromethyl)oxy]phenyl}oxy)acetyl]amino}methyl)-1,3-thiazol-4-yl]carbonyl}piperidine-4-carboxamide
N-[2-(2-chlorophenyl)ethyl]-2-({[({4-[(trifluoromethyl)oxy]phenyl}oxy)acetyl]amino}methyl)-1,3-oxazole-4-carboxamide
N-(2-pyrrolidin-1-ylethyl)-2-({[({4-[(trifluoromethyl)oxy]phenyl}oxy)acetyl]amino}methyl)-1,3-thiazole-4-carboxamide
N-[(1-ethylpyrrolidin-2-yl)methyl]-2-({[({4-[(trifluoromethyl)oxy]phenyl}oxy)acetyl]amino}methyl)-1,3-thiazole-4-carboxamide
N-[2-(2-fluorophenyl)ethyl]-2-({[(3E)-4-phenylbut-3-enoyl]amino}methyl)-1,3-thiazole-4-carboxamide -continued 2-[({[(4-bromophenyl)oxy]acetyl}amino)methyl]-N-{[2-(methyloxy)phenyl]methyl}-1,3-thiazole-4-carboxamide
1,1-dimethylethyl (1-{[2-({[({4-[(trifluoromethyl)oxy]phenyl}oxy)acetyl]amino}methyl)-1,3-thiazol-4-yl]carbonyl}pyrrolidin-3-yl)carbamate
N-({4-[(4-pyridin-2-ylpiperazin-1-yl)carbonyl]-1,3-thiazol-2-yl}methyl)-2-({4-[(trifluoromethyl)oxy]phenyl}oxy)acetamide
N-(2,2,2-trifluoroethyl)-2-({[({4-[(trifluoromethyl)oxy]phenyl}oxy)acetyl]amino}methyl)-1,3-thiazole-4-carboxamide
N-[2-(acetylamino)ethyl]-2-({[({4-[(trifluoromethyl)oxy]phenyl}oxy)acetyl]amino}methyl)-1,3-thiazole-4-carboxamide
N-({4-[(3,5-dimethylpiperidin-1-yl)carbonyl]-1,3-thiazol-2-yl}methyl)-2-({4-[(trifluoromethyl)oxy]phenyl}oxy)acetamide
ethyl 4-({[2-({[({4-[(trifluoromethyl)oxy]phenyl}oxy)acetyl]amino}methyl)-1,3-thiazol-4-yl]carbonyl}amino)piperidine-1-carboxylate
N-{[2-(methyloxy)phenyl]methyl}-2-({[(3E)-4-phenylbut-3-enoyl]amino}methyl)-1,3-thiazole-4-carboxamide
N-(pyridin-4-ylmethyl)-2-({[({4-[(trifluoromethyl)oxy]phenyl}oxy)acetyl]amino}methyl)-1,3-thiazole-4-carboxamide
N-[3-(2-oxopyrrolidin-1-yl)propyl]-2-({[({4-[(trifluoromethyl)oxy]phenyl}oxy)acetyl]amino}methyl)-1,3-thiazole-4-carboxamide
N-[2-(methyloxy)ethyl]-2-({[({4-[(trifluoromethyl)oxy]phenyl}oxy)acetyl]amino}methyl)-1,3-thiazole-4-carboxamide
N-[(2-methylphenyl)methyl]-2-({[({4-[(trifluoromethyl)oxy]phenyl}oxy)acetyl]amino}methyl)-1,3-oxazole-4-carboxamide
N-({4-[(3-methylpiperidin-1-yl)carbonyl]-1,3-thiazol-2-yl}methyl)-2-({4-[(trifluoromethyl)oxy]phenyl}oxy)acetamide
N-(2-piperidin-1-ylethyl)-2-({[({4-[(trifluoromethyl)oxy]phenyl}oxy)acetyl]amino}methyl)-1,3-thiazole-4-carboxamide
N-[(3,4-dichlorophenyl)methyl]-2-({[({4-[(trifluoromethyl)oxy]phenyl}oxy)acetyl]amino}methyl)-1,3-oxazole-4-carboxamide
N-[(4-fluorophenyl)methyl]-2-({[({4-[(trifluoromethyl)oxy]phenyl}oxy)acetyl]amino}methyl)-1,3-oxazole-4-carboxamide
N-(1,2,3,4-tetrahydronaphthalen-1-yl)-2-({[({4-[(trifluoromethyl)oxy]phenyl}oxy)acetyl]amino}methyl)-1,3-oxazole-4-carboxamide
N-{[4-(octahydroisoquinolin-2(1H)-ylcarbonyl)-1,3-thiazol-2-yl]methyl}-2-({4-[(trifluoromethyl)oxy]phenyl}oxy)acetamide
1,1-dimethylethyl methyl(1-{[2-({[({4-[(trifluoromethyl)oxy]phenyl}oxy)acetyl]amino}methyl)-1,3-thiazol-4-yl]carbonyl}pyrrolidin-3-yl)carbamate
N-(2-pyridin-2-ylethyl)-2-({[({4-[(trifluoromethyl)oxy]phenyl}oxy)acetyl]amino}methyl)-1,3-oxazole-4-carboxamide
N-(phenylmethyl)-2-({[({4-[(trifluoromethyl)oxy]phenyl}oxy)acetyl]amino}methyl)-1,3-oxazole-4-carboxamide
{4-[(trifluoromethyl)oxy]phenyl}methyl {[4-({[2-(3-chlorophenyl)ethyl]amino}carbonyl)-1,3-thiazol-2-yl]methyl}carbamate
N-[2-(3-chlorophenyl)ethyl]-5-({[({4-[(trifluoromethyl)oxy]phenyl}oxy)acetyl]amino}methyl)isoxazole-3-carboxamide
2-(aminomethyl)-N-[2-(3-chlorophenyl)ethyl]-1,3-thiazole-4-carboxamide
(4E,6Z,8S,9S,10E,12S,13R,14R,16S,17R)-4,10,12,16-tetramethyl-8,13,14,17-tetrakis(methyloxy)-3,20,22-trioxo-2-azabicyclo[16.3.1]docosa-1(21),4,6,10,18-pentaen-9-yl carbamate
2-({[({4-[(trifluoromethyl)oxy]phenyl}oxy)acetyl]amino}methyl)-1,3-thiazole-4-carboxylic acid
2-(aminomethyl)-N-{[2,3-bis(methyloxy)phenyl]methyl}-1,3-thiazole-4-carboxamide
2-(aminomethyl)-N-{[2-(methyloxy)phenyl]methyl}-1,3-thiazole-4-carboxamide
2-(aminomethyl)-N-[2-(2-fluorophenyl)ethyl]-1,3-thiazole-4-carboxamide
N-[2-(3-chlorophenyl)ethyl]-2-({[({4-[(trifluoromethyl)oxy]phenyl}oxy)acetyl]amino}methyl)-1H-imidazole-4-carboxamide
2-(aminomethyl)-N-[2-(3-chlorophenyl)ethyl]-1,3-oxazole-4-carboxamide
2-({[({4-[(trifluoromethyl)oxy]phenyl}oxy)acetyl]amino}methyl)-1,3-oxazole-4-carboxylic acid
N-[2-(3-chlorophenyl)ethyl]-2-{[({4-[(trifluoromethyl)oxy]phenyl}methyl)amino]methyl}-1,3-thiazole-4-carboxamide
N-[(4-{[4-ethyl-2-methyl-2-(3-methylbutyl)-1,3-oxazolidin-3-yl]carbonyl}-1,3-thiazol-2-yl)methyl]-2-({4-[(trifluoromethyl)oxy]phenyl}oxy)acetamide; or
N-[(4-{[3-(diethylamino)pyrrolidin-1-yl]carbonyl}-1,3-thiazol-2-yl)methyl]-2-({4-[(trifluoromethyl)oxy]phenyl}oxy)acetamide.

25. A pharmaceutical composition comprising a compound according to claim 1 and a pharmaceutically acceptable excipient or carrier.

26. The compound of claim 1, wherein alkyl, aryl, and heterocyclyl, are substituted, one or more hydrogen atoms are replaced by a substituent independently selected from alkyl, aryl, arylalkyl, heterocyclylalkyl, heterocyclyl, alkoxy, alkylenedioxy, amino, alkylamino, dialkylamino, amidino, aryloxy, arylalkyloxy, carboxy, acyloxy, carboxyalkyl, carboxamido, benzyloxycarbonylamino, cyano, acyl, halogen, hydroxy, nitro, —S-alkyl, —S-aryl, —S-heterocyclyl, —S(O)—H, —S(O)-alkyl, —S(O)-aryl, —S(O)-heterocyclyl, —S($O_2$)—H, —S($O_2$)-alkyl, —S($O_2$)-aryl, —S($O_2$)-heterocyclyl, —S($O_2$)-alkoxy, —S($O_2$)-aryloxy, —S($O_2$)-heterocyclyloxy, thiol, halogen, hydroxy, oxo, carbamyl, acylamino, and sulfonamido.

27. The compound of claim 1, wherein $R^4$ is —$CH_2$—O—Ph, wherein the phenyl is substituted with —$OCF_3$.

28. The compound of claim 1, wherein $R^4$ is

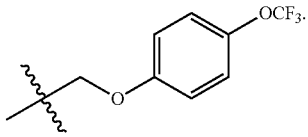

29. The compound of claim 13, wherein alkyl, aryl, and heterocyclyl, are substituted, one or more hydrogen atoms are replaced by a substituent independently selected from alkyl, aryl, arylalkyl, heterocyclylalkyl, heterocyclyl, alkoxy, alkylenedioxy, amino, alkylamino, dialkylamino, amidino, aryloxy, arylalkyloxy, carboxy, acyloxy, carboxyalkyl, carboxamido, benzyloxycarbonylamino, cyano, acyl, halogen, hydroxy, nitro, —S-alkyl, —S-aryl, —S-heterocyclyl, —S(O)—H, —S(O)-alkyl, —S(O)-aryl, —S(O)-heterocyclyl, —S(O$_2$)—H, —S(O$_2$)-alkyl, —S(O$_2$)-aryl, —S(O$_2$)-heterocyclyl, —S(O$_2$)-alkoxy, —S(O$_2$)-aryloxy, —S(O$_2$)-heterocyclyloxy, thiol, halogen, hydroxy, oxo, carbamyl, acylamino, and sulfonamido.

30. The compound of claim 13, wherein $R^4$ is —CH$_2$—O-Ph, wherein the phenyl is substituted with —OCF$_3$.

31. The compound of claim 1, wherein $R^4$ is

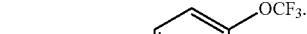

* * * * *